United States Patent
Bucala et al.

(10) Patent No.: US 6,645,493 B1
(45) Date of Patent: Nov. 11, 2003

(54) COMPOSITION CONTAINING ANTI-MIF ANTIBODY

(75) Inventors: Richard J. Bucala, New York, NY (US); Robert A. Mitchell, New York, NY (US); Jurgen Bernhagen, New York, NY (US); Thierry F. Calandra, New York, NY (US); Anthony Cerami, Shelter Island, NY (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 08/471,705

(22) Filed: Jun. 6, 1995

Related U.S. Application Data

(60) Division of application No. 08/462,350, filed on Jun. 5, 1995, now abandoned, which is a continuation-in-part of application No. 08/243,342, filed on May 16, 1994, now abandoned, which is a continuation-in-part of application No. 08/063,399, filed on May 17, 1993, now abandoned.

(51) Int. Cl.$^7$ ................... A61K 39/00; A61K 39/395; C07K 16/00; C12P 21/00

(52) U.S. Cl. ................... 424/145.1; 424/133.1; 424/141.1; 424/130.1; 424/158.1; 530/387.1; 530/387.3; 530/387.9; 530/388.1; 530/388.15; 530/389.1

(58) Field of Search ................... 424/145.1, 158.1, 424/85.1, 130.1, 133.1, 143.1, 141.1, 144.1, 152.1, 172.1, 184.1, 198.1; 514/2, 21; 530/388.23, 388.24, 389.1, 388.15, 350, 387.1, 387.3, 388.1, 387.9

(56) References Cited

U.S. PATENT DOCUMENTS

| | | | |
|---|---|---|---|
| 4,299,814 A | * 11/1981 | Brandt et al. ................... 424/1 |
| 4,683,202 A | 7/1987 | Mullis |
| 4,708,937 A | * 11/1987 | Remold ....................... 530/350 |
| 5,350,687 A | * 9/1994 | Odink et al. ............. 530/387.9 |
| 5,747,023 A | 5/1998 | Goeddel et al. ........... 424/85.1 |
| 5,785,054 A | 7/1998 | Kelly ......................... 128/842 |
| 5,786,168 A | 7/1998 | Ishizaka et al. ........... 435/69.1 |
| 5,945,096 A | 8/1999 | Ishizaka et al. ........... 424/85.1 |

FOREIGN PATENT DOCUMENTS

| | | | |
|---|---|---|---|
| DE | 230876 | * 12/1985 |
| WO | WO-90/11301 A1 | * 10/1990 |
| WO | WO-9107418 | * 5/1991 |

OTHER PUBLICATIONS

Sun et al, *Protein Engineering* 9(8) 1996, p631–35.*
Moore *Clin Chem* 35(9) 1989, p1849–53.*
The Cytokine FactBook ed, 1994 by Callard, pp 179–80.*
Gomez et al. *Cecta Dermatol Res* 1990, 282, 374–78.*
Neumann et al, *J Invest Dermatol* 85,1987, p 670–74.*
Waldmann et al, *J Reticuloendothelial Soc.* 23(5) 1978, p 335.*
Fahlbusch et al, *Biomed. Biochim Acta* 45(3) 1986, p371–84.*
Waser et al, *Cell Immunol* 90(1) 1985, p167–78.*
Onozoki et al. Cell Immunol 55(2) 1980, p465–75.*
Burmeister et al Immunology 171, 1986, p 461–74.*
Kawaguski et al, J Leukocyte Biol 39(2) 1986, p 223–32.*
Papageorgiou et al. Production and characterization of migration inhibitory factor(s) (MIF) of established lymphoid and non–lymphoid cell lines. J. Immunol. 108(2): 494–504, 1972.*
Yoshida et al. The production of anti–guinea pig lymphokine antibody. J. Immunol. 114(2): 688–691, 1975.*
Yoshida et al. Lymphokine–like factors produced by human lymphoid cell lines with B or T cell surface markers. J. Immunol. 117(2): 548–654, 1976.*
Possanza et al. Human macrophage migration inhibition factor: evidence for subunit structure. Science 205: 300–301, 1979.*
David et al., "Delayed Hypersensitivity in Vitro: Its Mediation By Cell Free Substances Formed by Lymphoid Cell–Antigen Interaction", Pathology 56:72–77 (1966).
Bennett and Bloom, "Mechanism of a Reaction in Vitro Associated with Delayed–Type Hypersensitivity", Science 153:80–82 (1966).
Nathan et al., "Alterations of Macrophage by Mediators From Lymphocytes", J Exp Medicine 133:1356–1376 (1971).
Nathan et al., "Characterization of a Lymphocyte Factor Which Alters Macrophage Functions", J Exp Medicine 137:275–288 (1973).
Kohler and Milstein, "Continuous Culture of Fused Cells Secreting Antibody of Predefined Speificity", Nature 256:495–497 (1975).
Weiser et al., "Studies of Human Migration Inhibitory Factor: Characterization of Three Molecular Species", J Immunol 126:1958–1962 (1981).
Kaiser and Kezdy, "Secondary Structures of Proteins and Peptides in Amphiphilic Environments (A Review)", Proc Natl Acad Sci USA 80:1137–1143 (1983).
Peck, "The ELISA Method for Quantitation of Macrophage Migration from Agarose Microdroplets", J Immunol Methods 64:179–187 (1983).

(List continued on next page.)

Primary Examiner—Elizabeth C. Kemmerer
Assistant Examiner—Bridget E. Bunner
(74) Attorney, Agent, or Firm—Piper Rudnick, LLP; Steven B. Kelber

(57) ABSTRACT

The present invention relates to compositions and methods for inhibiting the release and/or biological activity of migration inhibitory factor (MIF). In particular, the invention relates to the uses of such compositions and methods for the treatment of various conditions involving cytokine-mediated toxicity, which include, but are not limited to shock, inflammation, graft versus host disease, and/or autoimmune diseases.

9 Claims, 22 Drawing Sheets

OTHER PUBLICATIONS

Figure 1:
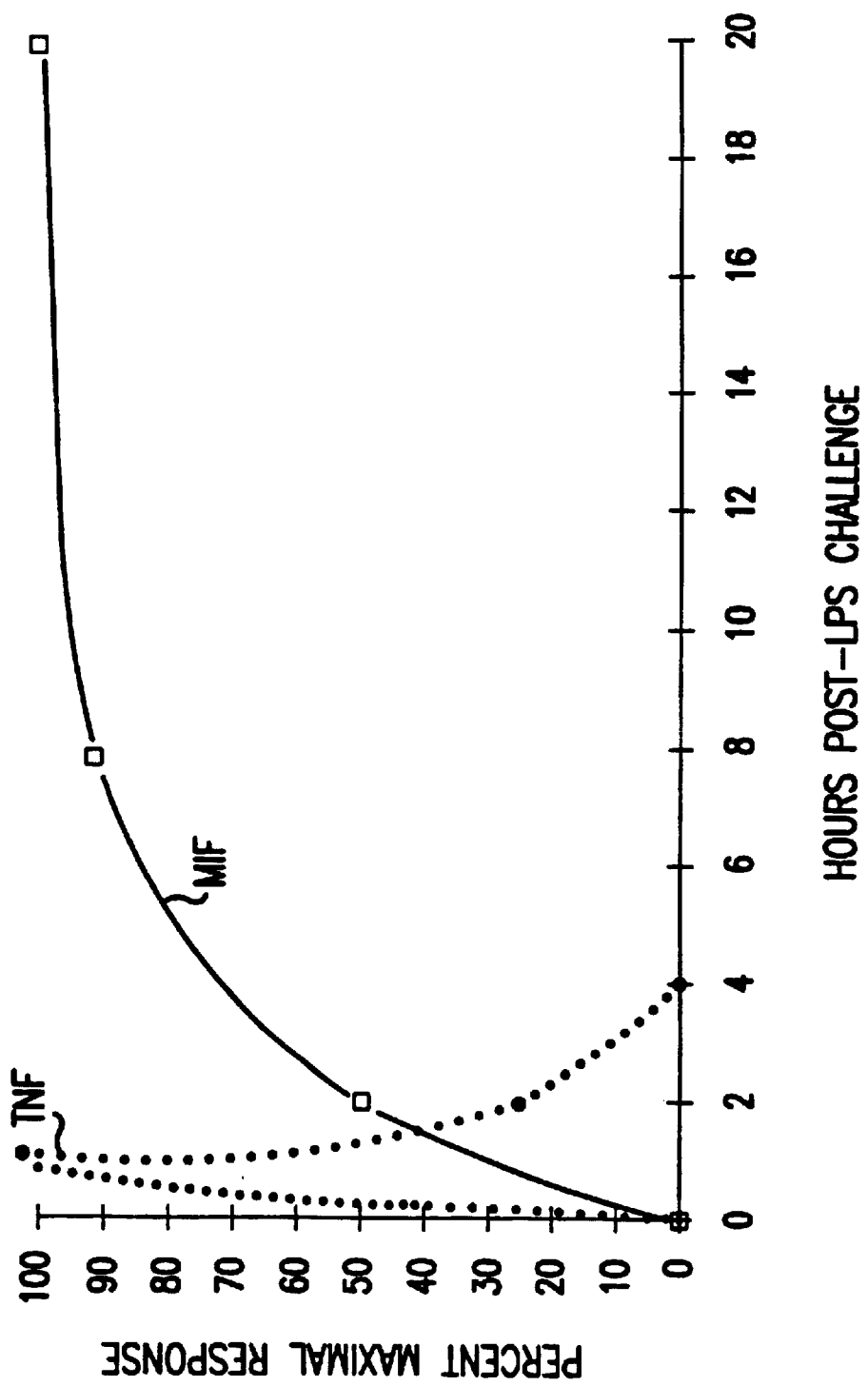

Morrison et al., "Chimeric Human Antibody Molecules: Mouse Antigen–Binding Domains with Human Constant Region Domains", Proc Natl Acad Sci 81:6851–6855 (1984).

Sprung et al., "The Effects of High Dose Corticosteroids in Patients with Septic Shock", New Eng Eng J Med 311:1137–1143 (1984).

Beutler et al., "Purification of Catechin, A Lipoprotein Lipase–Suppressing Hormone Secreted by Endotoxin–Induced Raw 264.7 Cells", J Exp Med 161:984–995 (1985).

Erne et al., "Preferred Confirmation, Orientation, and Accumulation of Dynorphin A–(1–13)–Tridecapeptides on the Surfaces of Neutral Lipid Membranes", Biochemistry 24:4263–4265 (1985).

Beutler et al., "Catechin/Tumor Necrosis Factor: Production, Distribution, and Metabolic Fate in Vivo", J Immunol 135:3972–3977 (1985).

Suzuki et al., "Pituitary–Dependent and –independent Secretion of CS Caused by Bacterial Endoxtin in Rats", Am J Physiol 250:E470–E474 (1986).

Liu and Todd, "A Monoclonal Antibody Specific for a Monocyte–Macrophage Membrane Component Blocks the Human Monocyte Response to Migration Inhibitory Factor", J Immuno 137:448–455 (1986).

Thomas and Cappechi, "Site–Directed Mutagen by Gene Targeting in Mouse Embryo–Derived Stem Cells", Cell 51:503–512 (1987).

Bone et al., "A Controlled Clinical Trial of High–Dose Methylprednisolone in the Treatment of Severe Sepsis and Septic Shock", New Eng J Med 311:1137–1141 (1987).

Ding et al., "Release of Reactive Nitrogen Intermediates and Reactive Oxygen Intermediates From Mouse Peritoneal Macrophages", J Immunol 141:2407–2413.

Smith, "Interleukin 2: Inception, Impact, and Implications", Science 240:1169–1176 (1988).

Michie et al., "Detection of Circulating Tumor Factor After Endotoxin Administration", New Eng J Med 318:1481–1486 (1988).

Wolpe et al., "Macrophages Secrete a Novel Heparin–Binding Protein With Imflammatory and Neutrophil Chemokinetic Properties", J Exp Medicine 167:570–581 (1988).

Huse et al., "Generation of a Large Combinatorial Library of the Immunoglobin Repertoire in Phage Lambda", Science 246:1275–1281 (1989).

Sternberg et al., "Inflammatory Mediator–Induced Hypothalamic–Pituitary–Adrenal Axis Activation is Defective in Streptococcal Cell Wall Arthritis–Susceptible Lewis Rats", Proc Natl Acad Sci USA 86:2374–2378 (1989).

Weiser et al., "Molecular Cloning of cDNA Encoding Human Macrophage Migration Inhibitory Factor", Proc Natl Acad Sci 86:7522–7526 (1989).

Zuckerman et al., "Differential Regulation of Lipopolysaccharide–Induced Interleukin 1 and Tumor Necrosis Factor Synthesis: Effects of Endogenous and Exogenous Glucocorticoids and the Role of the Pituitary–Adrenal Axis", Eur J Immunol 19:301–305 (1989).

Uhlmann and Peyman, "Antisense Oligonucleotides: A New Therapeutic Principle", Chem Rev 90:543–584 (1990).

Buhler et al., "Rabbit β–Casein Promoter Directs Secretion of Human Interleukin–2 into the Milk of Transgenic Rabbits", Biotechnology 8;140–143 (1990).

Edwards III et al., "Hypophysectomy Inhibits the Synthesis of Tumor Necrosis Factor α by Rat Macrophages: Partial Restoration by Exogenous Growth Hormone or Interferon γ", Endocrinol 128:989–986 (1991).

Dinarello, "The Proinflammatory Cytokines Interleukin–1 and Tumor Necrosis Factor and Treatment of the Septic Shock Syndrome", J Infect Dis 163:1177–1184 (1991).

Edwards III et al, "The Pituitary is Required for Protection Against Lethal Effects of Salmonella Typhimurium", Proc Natl Acad Sci USA 88:2274–2277 (1991).

Silverstien et al., "Hydrazine Sulfate Protects D–Galactosamine–Sensitized Mice Against Endotoxin and Tumor Necrosis Factor/Cachetin Lethality: Evidence of a Role for the Pituitary", J Exp Med 173:357–365 (1991).

Lam et al., "A New Type of Synthetic Peptide Library for Identifying Ligand Binding Activity", Nature 354:82–84 (1991).

Fung–Leung et al., "CD8 is Needed for the Development of Cytotoxic T–Cells but not Helper T–Cells", Cell 65:443–449 (1991).

Holmes et al., "Structure and Functional Expression of a Human Interleukin–8 Receptor", Science 253:1278–1280 (1991).

Weiser et al., "Human Recombinant Migration Inhibitory Factor Activates Human Macrophages to Kill Leishmania Donovani", J Immunol 147:2006–2011 (1991).

Pozzi et al., "Human Recombianant Migration Inhibitory Factor Activates Human Macrophages to Kill Tumor Cells", Cellular Immunol 145:372–379 (1992).

Fry et al., "Solution Structures of Cyclic and Dicyclic Anologues of Growth Hormones Releasing Factor as Determined by Two–Dimensional NMR and CD Spectroscopies and Constrained Molecular Dynamics", Biopolymer 32:649–666 (1992).

Sigal and Dumont, "Cyclosporin A, FK–506, and Rapamycin: Pharmacologic Probes of Lymphocyte Signal Transduction", Ann Rev Immunol 10:519–560 (1992).

Blocki et al., "Rat Liver Protein Linking Chemical and Immunological Detoxification Systems", Nature 360:269–270 (1992).

Vassalli, "The Pathophysiology of Tumor Necrosis Factors", Ann Rev Immunol 10:411–452 (1992).

Weiser et al., "Recombinant Human Migration Inhibitory Factor has Adjuvant Activity", Procl Natl Acad Sci USA 89:8049–8052 (1992).

Lanahan et al., "Growth Factor–Induced Delayed Early Resonse Genes", Mol Cell Biol 12:3919–3929 (1992).

Sherry et al., "Identification of Cyclophilin as a Proinflammatory Secretory Product of Lipopolycaccharide–Activated Macrophages", Proc Natl Acad Sci USA 89:3511–3515 (1992).

Bernhagen et al., "Identification of Macrophage Migration Inhibitory Factor (MIF) as an LPS–Induced Pituitary Protein in Vitro and in Vivo", J Cell Biochem. Supplement 17B, Abstract E306 (1993).

Wistow et al., "A Macrophage Migration Inhibitory Factor is Expressed in the Differentiating Cells of the Eye Lens", Proc Natl Acad Sci USA 90:1272–1275 (1993).

Bernhagen et al., "MIF is a Pituitary–Derived Cytokine that Potentiates Lethal Endotoxaemia", Nature 365:756–759 (1993).

Mikayama et al., "Molecular Cloning and Functional Expression of a cDNA Encoding Glycosylation Inhibiting Factor", Proc Natl Acad Sci USA 89:10056–10060 (1993).

Cunha et al., "Recombinant Migration Inhibitory Factor Induces Nitric Oxide Synthase in Murine Macrophages", J Immunol 150:1908–1912 (1993).

* cited by examiner

```
              10         20         30         40         50         60
mmif    ATGCCTATGTTCATCGTGAACACCAATGTTCCCCGCGCCTCCGTGCCAGAGGGGTTTCTG
        :::::  X:::::::::::  :::::::::  ::  ::::::::::::::  ::  ::::::  ::
>hmif.  ATGCCGATGTTCATCGTAAACACCAACGTGCCCCGCGCCTCCGTGCCGGACGGGTTCCTC
              10         20         30         40         50         60

70         80         90        100        110        120
mmif    TCGGAGCTCACCCAGCAGCTGGCGCAGGCCACCGGCAAGCCCGCACAGTACATCGCAGTG
        ::  ::::::::::::::::::::::::::::::::::::::::  :  :::::::::::  :::
>hmif.  TCCGAGCTCACCCAGCAGCTGGCGCAGGCCACCGGCAAGCCCCCCCAGTACATCGCGGTG
              70         80         90        100        110        120

130        140        150        160        170        180
mmif    CACGTGGTCCCGGACCAGCTCATGACTTTTAGCGGCACGAACGATCCCTGCGCCCTCTGC
        ::::::::::::::::::::::::::::::  :  ::   :::::  : :::  ::  :::::  :::::::
>hmif.  CACGTGGTCCCGGACCAGCTCATGGCCTTCGGCGGCTCCAGCGAGCCGTGCGCGCTCTGC
             130        140        150        160        170        180

190        200        210        220        230        240
mmif    AGCCTGCACAGCATCGGCAAGATCGGTGGTGCCCAGAACCGCAACTACAGTAAGCTGCTG
        :::::::::::::::::::::::::::::::  ::  ::  ::::::::::  ::::::  ::::::::::::
>hmif.  AGCCTGCACAGCATCGGCAAGATCGGCGGCGCGCAGAACCGCTCCTACAGCAAGCTGCTG
             190        200        210        220        230        240

250        260        270        280        290        300
mmif    TGTGGCCTGCTGTCCGATCGCCTGCACATCAGCCCGGACCGGGTCTACATCAACTATTAC
        ::  ::::::::::::  ::::  :::::::  :::::::::::::::  :::::::::::::::::::::
>hmif.  TGCGGCCTGCTGGCCGAGCGCCTGCGCATCAGCCCGGACAGGGTCTACATCAACTATTAC
             250        260        270        280        290        300

310        320        330        340
mmif    GACATGAACGCTGCCAACGTGGGCTGGAACGGTTCCACCTTCGCTTGA
        ::::::::::::  ::::  ::::::::::::::::  :::::::::X : :
>hmif.  GACATGAACGCGGCCAGTGTGGGCTGGAACAACTCCACCTTCGCCTAA
                  310        320        330        340
```

FIG.2 start
↓
CCATGCCTATGTTCATCGTGAACACCAATGTTCCCCGCGCC

TCCGTGCCAGAGGGGTTTCTGTCGGAGCTCACCCAGCAGCTGGCGCAGGCCACCGGCAAG

CCCGCACAGTACATCGCAGTGCACGTGGTCCCGGACCAGCTCATGACTTTTAGCGGCACG

AACGATCCCTGCGCCCTCTGCAGCCTGCACAGCATCGGCAAGATCGGTGGTGCCCAGAAC

CGCAACTACAGTAAGCTGCTGTGTGGCCTGCTGTCCGATCGCCTGCACATCAGCCCGGAC

CGCTCCTACAGCAAGCTGCTGTGCGGCCTGCTGGCCGAGCGCCTGCGCATCAGCCCGGAC

CGGGTCTACATCAACTATTACGACATGAACGCTGCCAACGTGGGCTGGAACGGTTCCACC

AGGGTCTACATCAACTATTACGACATGAACGCGGCCAGTGTGGGCTGGAACAACTCCACC

TTCGCTTGAGTCCTGGCCCCACTTACCTGCACCGCTGTTC
↓
stop

FIG.3

```
                     10                20                30                40                50                60
mu   MPMFIVNTNVPRASVPEGFLSELTQQLAQATGKPAQYIAVHVVPDQLMTFSGTNDPCALC
     :::::::::::::::  :::::::::::::::::::::  ::::::::::::      :::::
hu   MPMFIVNTNVPRASVPDGFLSELTQQLAQATGKPPQYIAVHVVPDQLMAFGGSSEPCALC 70                80                90               100               110
mu   SLHSIGKIGGAQNRNYSKLLCGLLLSDRLHISPDRVYINYYDMNAANVGWNGSTFA
     ::::::::::::::: ::::::::::::  :: :::::::::::::::::::  :::::
hu   SLHSIGKIGGAQNRSYSKLLCGLLAERLRISPDRVYINYYDMNAANVGWNNSTFA
```

FIG. 4

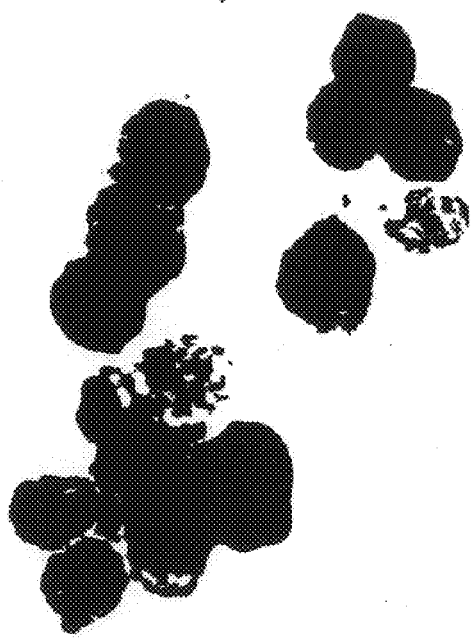 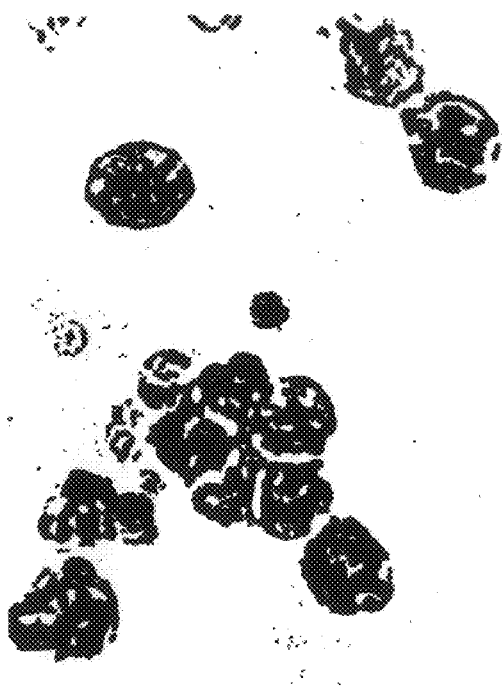
FIG.9A                    FIG.9B

COMPOSITION CONTAINING ANTI-MIF ANTIBODY

This is a divisional of application Ser. No. 08/462,350, filed Jun. 5, 1995, now abandoned, which is a continuation-in-part of application Ser. No. 08/243,342, filed May 16, 1994, now abandoned, which is a continuation-in-part of application Ser. No. 08/063,399, filed May 17, 1993, now abandoned.

1. INTRODUCTION

The present invention relates to compositions and methods for inhibiting the release and/or biological activity of migration inhibitory factor (MIF). In particular, the invention relates to the uses of such compositions and methods for the treatment of various conditions involving cytokine-mediated toxicity, which include, but are not limited to shock, inflammation, graft versus host disease, and/or autoimmune diseases.

2. BACKGROUND OF THE INVENTION

2.1. Cytokines in Septic Shock

Septic shock is a multifaceted pathological condition characterized most prominently by deleterious hemodynamic changes and coagulopathy leading to multiple organ failure and often to death. The altered physiological mechanisms underlying the septic shock syndrome, and the cellular means by which these changes are induced and controlled, are not yet known in precise detail. In broad outline, however, a consensus view of events culminating in septic shock has emerged over the last several years. In particular, it is now generally accepted that septic shock reflects the individual, combined and concerted effects of a large number of endogenous, host-derived mediator molecules. These mediators are produced in response to initiating stimuli that indicate the host has been invaded, and the class of peptide mediators that were generally first recognized as white blood cell products have come to be known as cytokines. As mediators of toxic effects and pathological alterations in host homeostasis, these endogenous factors represent potentially attractive therapeutic targets, and septic shock remains a potentially lethal cytokine-mediated clinical complication against which there is no generally effective therapeutic approach.

Although traditionally termed "septic" shock, infection by a variety of microorganisms including not only bacteria but also viruses, fungi, and parasites can induce septic shock. In fact, the shock syndrome is more properly associated with the host's response to invasion rather than just infection, as cancer and trauma, for instance, can also serve as initiators. In the case of infection by gram-negative bacteria, one of the best studied examples, it is believed that the appearance of bacterial endotoxins such as lipopolysaccharide (LPS) in the host bloodstream leads to the endogenous production of a variety of host factors that directly and indirectly mediate the toxicity of LPS, which itself is relatively innocuous for most cells. These host-derived mediators include many now well-recognized inflammatory cytokines and classical endocrine hormones in addition to a number of other endogenous factors such as leukotrienes and platelet activating factor. It is generally acknowledged, however, that the full cast of participants and each of their interrelated roles in the host response remains incompletely appreciated.

In general, those mediators that appear earlier in an invaded host are thought to trigger the release of later appearing factors. Also, many endogenous mediators not only exert direct effector functions at their target tissues, but also prime local and remote tissues for subsequent responses to other mediators. This interacting network of host factors has been termed the "cytokine cascade." This term is meant to indicate the rapid extension and amplification of the host response in such a way that only one or a few initiating stimuli trigger the eventual release and participation of scores of host mediators. Although a number of features of the host response are thought to assist in fighting off invasion, an overly robust or poorly modulated endogenous response can rapidly accelerate to rapidly produce such profound alterations in host homeostasis at the cellular, tissue, and systemic levels that death may ensue within hours.

Among the interacting factors that together comprise the cytokine cascade, the cytokine known as tumor necrosis factor-alpha (TNFα) is the most important identified to date. TNFα is the first cytokine to appear in the circulation after LPS challenge. The hemodynamic and metabolic alterations that result from the experimental administration of TNFα closely resemble those that have been observed in endotoxemia and septic shock. In animal models, TNFα is the only host factor which itself can initiate a lethal syndrome that mimics septic shock in detail. In this respect, TNFα can be considered a sufficient mediator of septic shock. Functionally neutralizing TNFα antagonists such as anti-TNFα antibodies are protective in otherwise lethal bacterial infections, and in this respect TNFα can be considered a necessary mediator of septic shock.

Other cytokines participate in the host response to LPS but appear later in the circulation. However, no other cytokine has been shown to be both necessary and sufficient to mediate septic shock. For example, certain interleukins (IL-1, IL-6 and IL-8) which appear in serum more than 2 hours after LPS challenge, and interferon γ (IFN-γ) which appears after 6 hours, are thought to play a significant role in septic shock, and can be shown to contribute to lethality in certain disease models or under experimental conditions of endotoxemia. Antagonism of the effects of specific interleukins and interferons has been shown to confer a significant protective effect under certain conditions. Nevertheless, none of these other factors can itself induce a full-blown septic shock-like effect in otherwise healthy individuals, and none of these other cytokines appears to play as central and critical role in septic shock as TNFα.

In view of the foregoing, TNFα stands as an ideal target for the treatment of septic shock. Unfortunately, temporal characteristics of the endogenous TNFα response suggest a significant practical limitation for this potential therapy. TNFα, one of the earliest elicited mediators to appear in acute disease, rapidly peaks after bolus endotoxin challenge (30–90 minutes), and diminishes just as promptly. It is presumed that most of the damaging effects of TNFα in septic shock are completed during this early period, hence TNFα antagonists such as anti-TNFα antibodies would ideally be present at this time. Since this therapeutic window is apparently so short and occurs so early, the timely delivery of anti-TNFα based therapeutics may be very difficult to achieve clinically.

Therefore, in order utilize cytokines as targets for the treatment of septic shock and other cytokine-mediated toxic reactions, there exists a desperate need to discover additional targets that are both necessary components of the cytokine cascade and occur at a time during the endogenous response that is accessible for therapeutic antagonism in the course of clinical treatment.

2.2. The Pituitary as a Source of Protective Cytokines

Recent studies suggest that the pituitary gland may produce factors that inhibit endotoxin-induced TNFα and IL-1 production, and thus may serve as a source for potentially protective factors that may be used to treat shock and/or other inflammatory responses. (Suzuki et al., 1986, Am. J. Physiol. 250: E470–E474; Sternberg et al., 1989, Proc. Natl. Acad. Sci. USA 86: 2374–2378; Zuckerman et al., 1989, Eur. J. Immunol. 19: 301–305; Edwards III et al., 1991a, Endocrinol. 128: 989–996; Edwards III et al., 1991b, Proc. Natl. Acad. Sci. USA 88: 2274–2277, Silverstein et al., 1991, J. Exp. Med. 173:357–365). In these studies, hypophysectomized mice (i.e., animals that have had their pituitary glands surgically removed) exhibited a marked increased sensitivity to LPS injection relative to sham-operated control mice. In fact, the LPS $LD_{100}$ for control mice was approximately 1–2 logs higher than that determined for the hypophysectomized mice, suggesting that the pituitary gland produces one or more factors that may act to increase the host animal's ability to resist endotoxin challenge. Some of these studies implicate the involvement of ACTH and adrenocorticosteroids (e.g., Edwards III et al., 1991a and 1991b, supra); however, other data suggest the existence of other protective factors derived from the pituitary.

Very recently, murine macrophage migration inhibitory factor (MIF) was identified as an LPS-induced pituitary protein (Bernhagen et al., 1993, J. Cell. Biochem. Supplement 17B, Abstract E306). While it may be hypothesized that MIF is one of such protective factors capable of counteracting the adverse effects of cytokines in endotoxaemias, its role in septic shock had not been investigated prior to the present invention.

2.3. MIF: Macrophage Migration Inhibitory Factor

Although MIF was first described over 25 years ago as a T cell product that inhibits the random migration of guinea pig macrophages (Bloom & Bennett, 1966, Science 158: 80–82; David, 1966, Proc. Natl. Acad. Sci. USA 65: 72–77), the precise role of MIF in either local or systemic inflammatory responses has remained largely undefined. MIF has been reported to be associated with delayed-type hypersensitivity reactions (Bloom & Bennett, 1966, supra; David, 1966, supra), to be produced by lectin-activated T-cells (Weiser et al., 1981, J. Immunol. 126: 1958–1962), and to enhance macrophage adherence, phagocytosis and tumoricidal activity (Nathan et al., 1973, J. Exp. Med. 137: 275–288; Nathan et al., 1971, J. Exp. Med. 133: 1356–1376; Churchill et al., 1975, J. Immunol. 115: 781–785). Unfortunately, many of these studies used mixed culture supernatants that were shown later to contain other cytokines such as IFN-γ and IL-4 that also have migration inhibitory activity (McInnes & Rennick, 1988, J. Exp. Med. 167: 598–611; Thurman et al., 1985, J. Immunol. 134: 305–309).

Recombinant human MIF was originally cloned from human T cells (Weiser et al., 1989, Proc. Natl. Acad. Sci. USA 86: 7522–7526), and has been shown to activate blood-derived macrophages to kill intracellular parasites and tumor cells in vitro, to stimulate IL-1β and TNFα expression, and to induce nitric oxide synthesis (Weiser et al., 1991, J. Immunol. 147: 2006–2011; Pozzi et al., 1992, Cellular Immunol. 145: 372–379; Weiser et al., 1992, Proc. Natl. Acad. Sci. USA 89:8049–8052; Cunha et al., 1993, J. Immunol. 150:1908–1912). Until very recently, however, the lack of a reliable source of purified MIF has continued to hamper investigation of the precise biological profile of this molecule.

3. SUMMARY OF THE INVENTION

The present invention relates to compositions and methods which inhibit the release and/or biological activity of migration inhibitory factor (MIF). The invention further relates to the uses of such compositions and methods for the treatment of conditions involving cytokine-mediated toxicity, which include, but are not limited to shock, inflammation, graft versus host disease, and/or autoimmune diseases.

The inhibition of MIF activity in accordance with the invention may be accomplished in a number of ways which include, but are not limited to, the use of MIF binding partners, i.e., factors that bind to MIF and neutralize its biological activity, such as neutralizing anti-MIF antibodies, soluble MIF receptors, MIF receptor fragments, and MIF receptor analogs; the use of MIF-receptor antagonists, such as anti-MIF-receptor antibodies, inactive MIF analogs that bind but do not activate the MIF-receptor, small molecules that inhibit MIF release, or alter the normal configuration of MIF, or inhibit productive MIF/MIF-receptor binding; or the use of nucleotide sequences derived from MIF gene and/or MIF receptor gene, including coding, non-coding, and/or regulatory sequences to prevent or reduce MIF expression by, for example, antisense, ribozyme, and/or triple helix approaches. Any of the foregoing methods may be utilized individually or in combination to inhibit MIF release and/or activity in the treatment of the relevant conditions. Further, such treatment(s) may be combined with other therapies that (a) inhibit or antagonize initiators of cytokine-mediated toxicity (e.g. anti-LPS antibody); (b) inhibit or antagonize toxic participants in the endogenous cytokine responses (e.g. anti-TNFα, anti-IL-1, anti-IFN-γ, or IL-1 RA); or (c) themselves inhibit or antagonize cytokine-mediated toxicity (e.g. steroids, glucocorticoids or IL-10).

The present invention is based, in part, on the surprising discoveries that, first, administration of MIF in vivo increases mortality of animals after challenge with endotoxin and, second, that inhibition of MIF activity in vivo results in enhanced or prolonged survival after either challenge with endotoxin or with TNFα, which challenge would otherwise result in death due to shock. Prior to the present invention, no role for MIF in the inflammation/shock response was appreciated. Moreover, the existing evidence and observations indicated, at best, that MIF might play a beneficial role in the treatment of endotoxin-induced shock. First, MIF was shown to enhance macrophage killing of intracellular parasites and tumor cells. Second, MIF is an endotoxin-induced protein expressed by the pituitary, an organ which had previously been suggested as a source of protective rather than exacerbative factors involved in the shock syndrome. In contrast to such expectations, the Applicants have discovered that MIF activity actually exacerbates endotoxin-induced shock, and that inhibition of MIF activity can be used to successfully treat otherwise lethal effects of cytokine-mediated toxicity.

The invention is also based, in part, on the Applicants' discovery of the role of MIF in humoral immune responses, which is demonstrated in animal models by way of a working example. In animals immunized with a test antigen in conjunction with the administration of an anti-MIF antibody, an inhibition of the development of a primary immune response to the test antigen was observed. These results indicate a means by which MIF activity modulates the primary immune response and therefore anti-MIF treatment could potentially be useful in substantially reducing an undesired immune response, such as autoimmunity and allergy. In contrast, this observation also indicates the involvement of MIF in a primary immune response. Thus, MIF may be administered as an adjuvant for an antigen during immunization of a naive individual to induce an enhanced immune response to the antigen.

The invention is illustrated by working examples which demonstrate that MIF exacerbates endotoxin-induced shock, and that anti-MIF prevents endotoxin-induced lethality in animal models. In addition, the working examples also describe the organ distribution of MIF and its receptor, the identification of a murine MIF receptor, the production of anti-MIF monoclonal antibodies, and the inhibition of immune responses by anti-MIF antibodies.

4. BRIEF DESCRIPTION OF THE FIGURES

FIG. 1: Graph depicting the schematic profile of TNFα and MIF responses involved in LPS-induced shock.

FIG. 2: Potential ribozyme cleavage sites of MIF.

Murine (mmif) and human (hmif) nucleotide sequences are compared. Underlined sequences indicate the potential ribozyme cleavage sites.

FIG. 3: Nucleotide sequence of cDNA encoding murine MIF.

FIG. 4: Predicted amino acid sequence homology between murine pituitary MIF and human Jurkat T-cell MIF. Potential N-linked glycosylation sites are underlined. mu: murine MIF; hu: human MIF.

Figure 5:
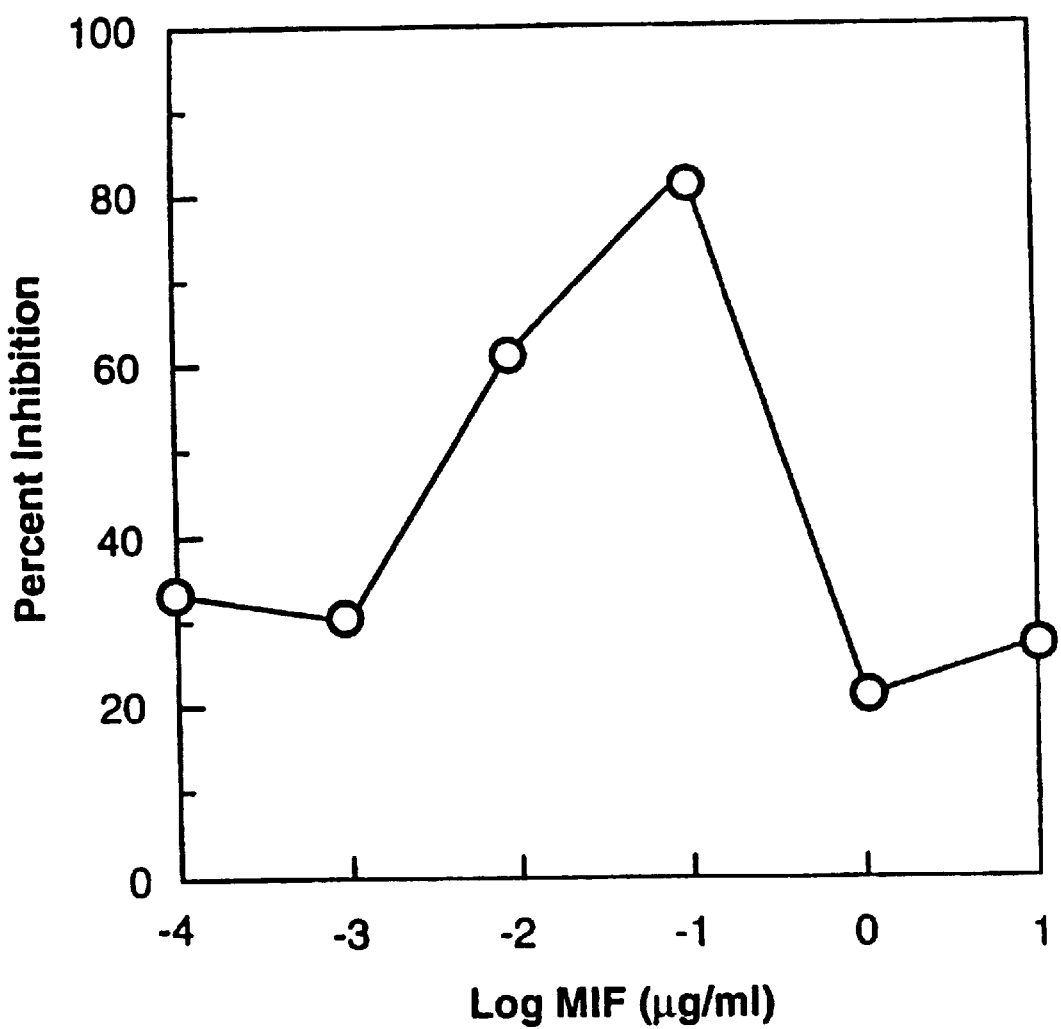

FIG. 5: Inhibition of monocyte migration by recombinant MIF. The effect of various concentrations (0.0001–10 μg/ml) of rmuMIF on peripheral human blood monocyte migration was quantitated in a modified Boyden chamber. The percent migration inhibition relative to buffer controls is plotted versus the logarithm of MIF concentration. Each point depicts the mean of independently performed duplicate determinations.

Figure 6A:
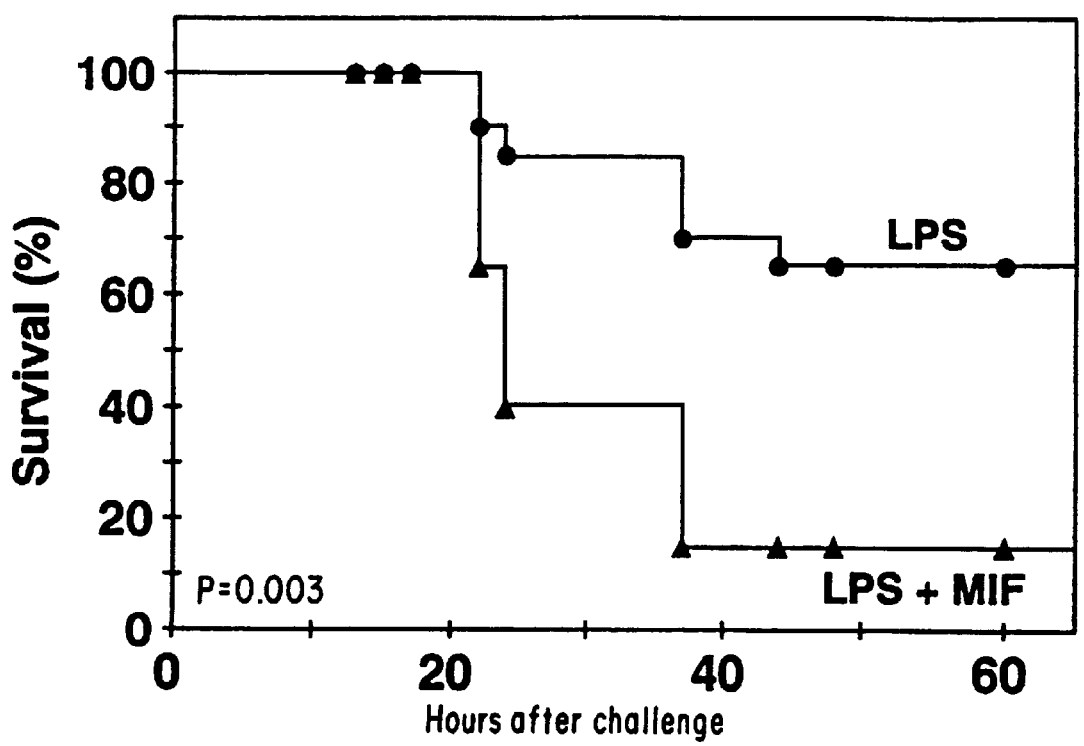

FIG. 6A: MIF potentiates LPS-induced lethality in BALB/c mice. Results represent the pooled data from two experiments.

Figure 6B:
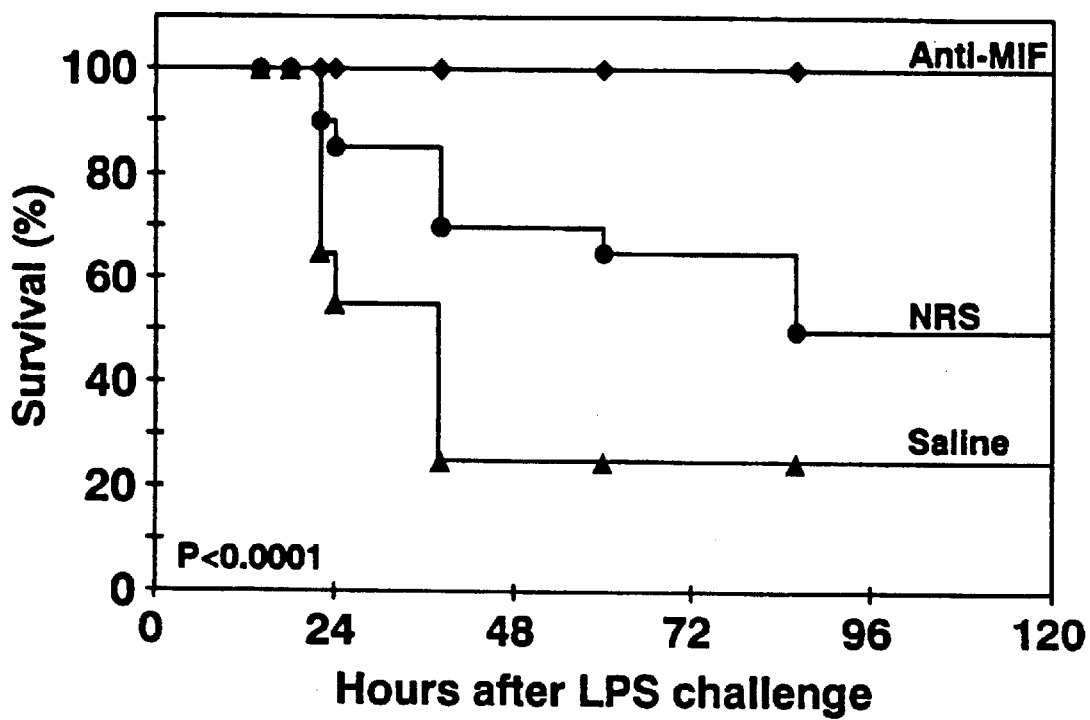

FIG. 6B: Anti-MIF antiserum protects against LPS challenge. Results represent the pooled data from two experiments.

Figure 7:
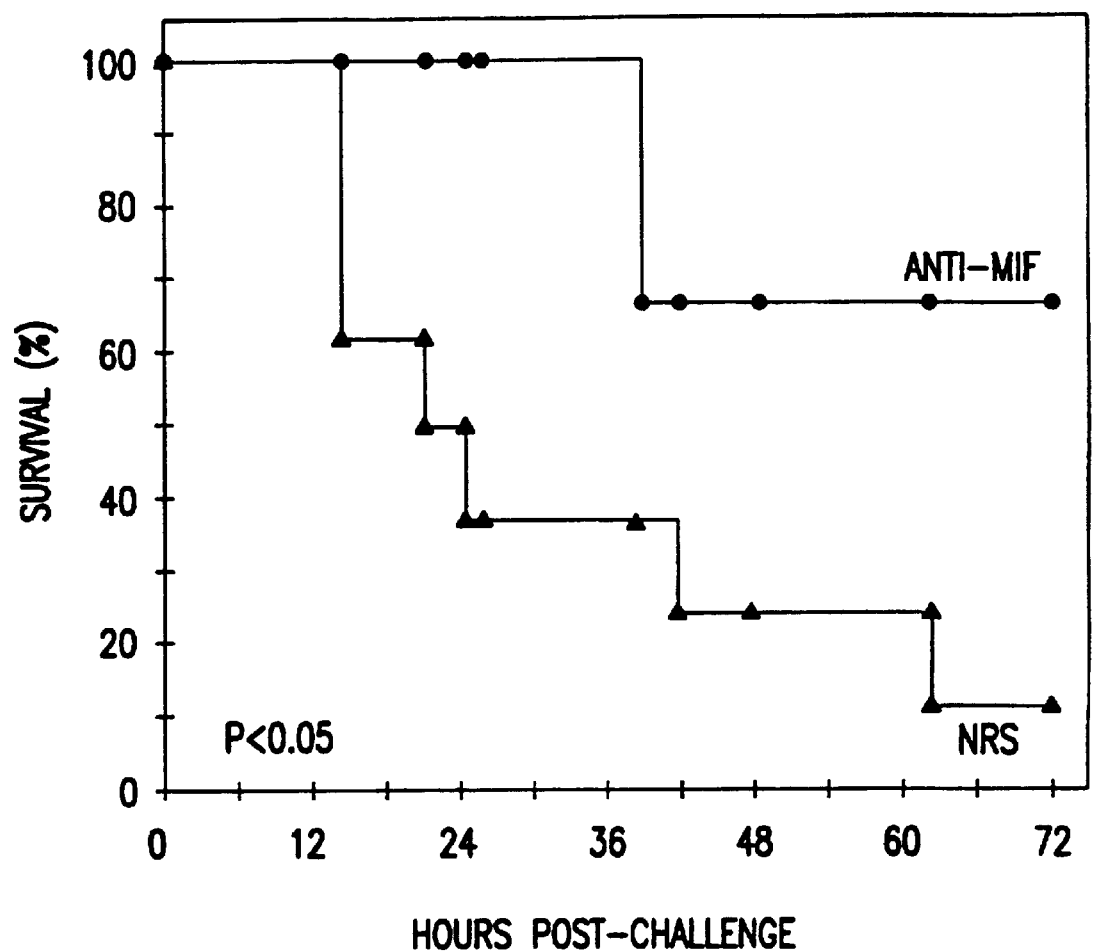

FIG. 7: Anti-MIF antiserum protects against Gram-positive staphylococcal exotoxin challenge.

Figure 8:
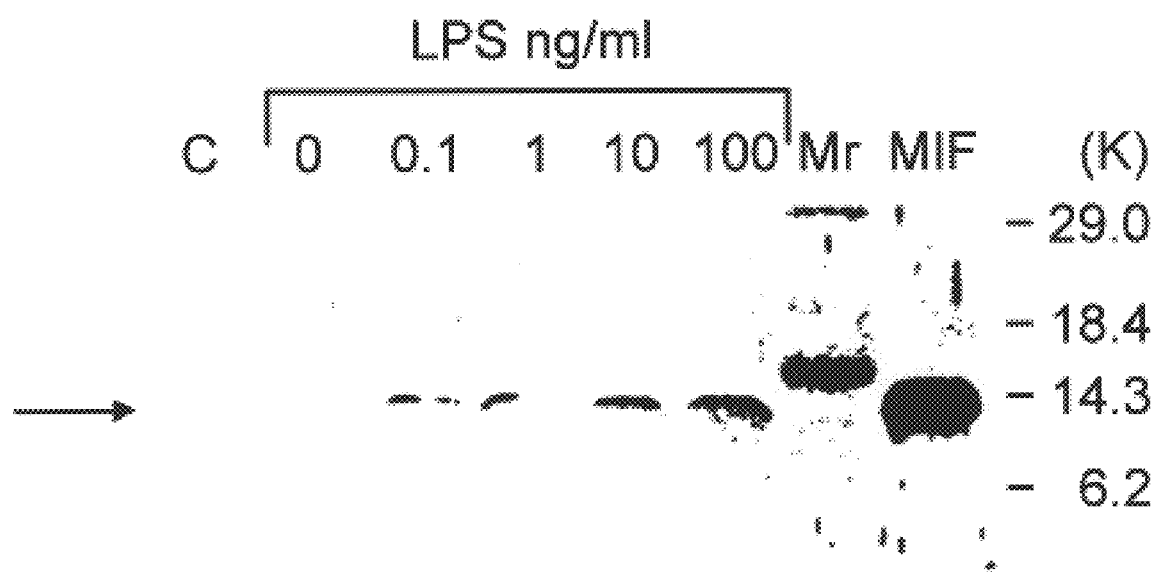

FIG. 8: Western blot analysis of MIF released by pituitary cells.

FIGS. 9A and 9B: Immunocytochemistry of MIF release by pituitary cells. FIG. 9.A. Cells cultured in the absence of LPS; FIG. 9.B. Cells cultured in the presence of 25 μg/ml LPS.

Figure 10:
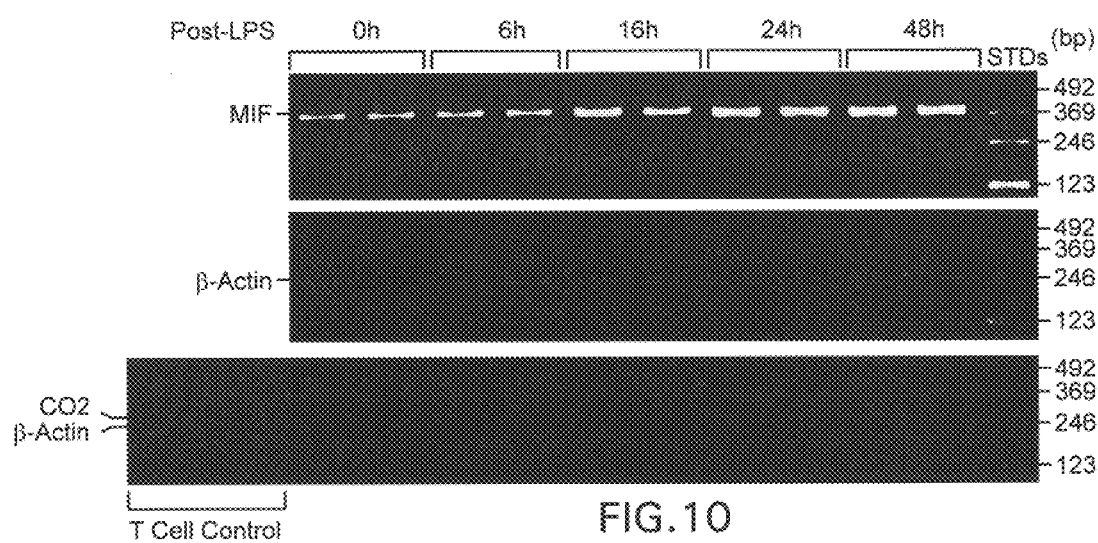

FIG. 10: LPS-induced expression of pituitary MIF mRNA in BALB/c mice.

Figure 11:
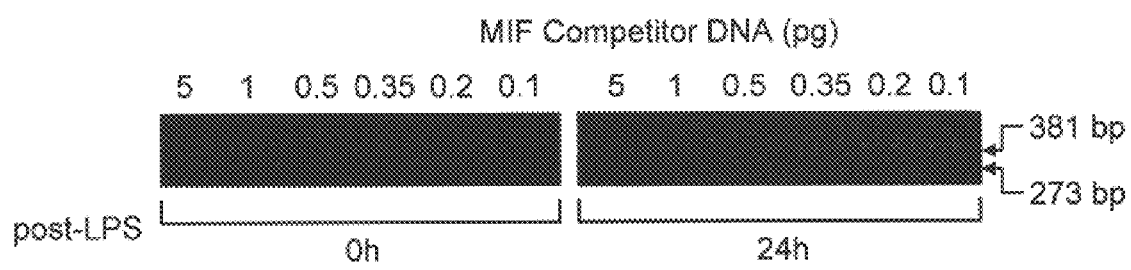

FIG. 11: Competitive PCR quantitation of pituitary MIF mRNA from LPS-stimulated BALB/c mice.

Figure 12:
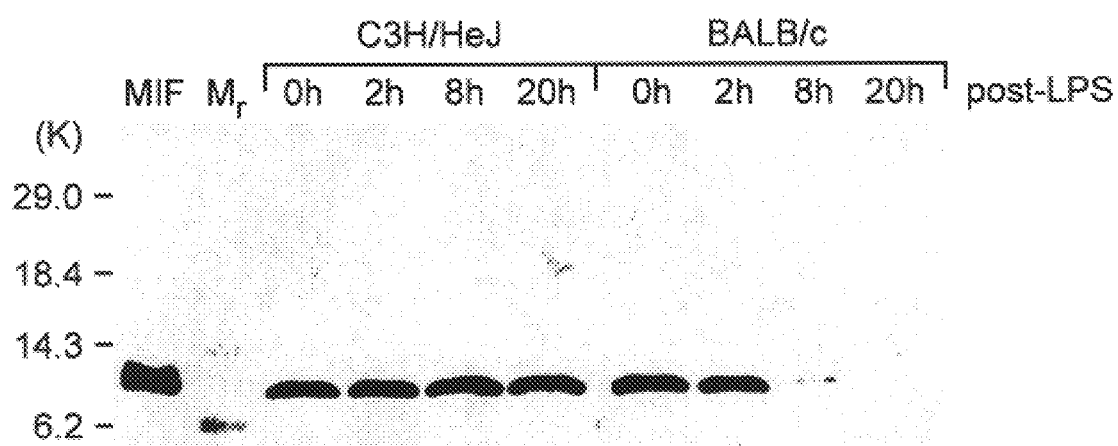

FIG. 12: Presence of MIF protein in mouse pituitaries.

Figure 13:
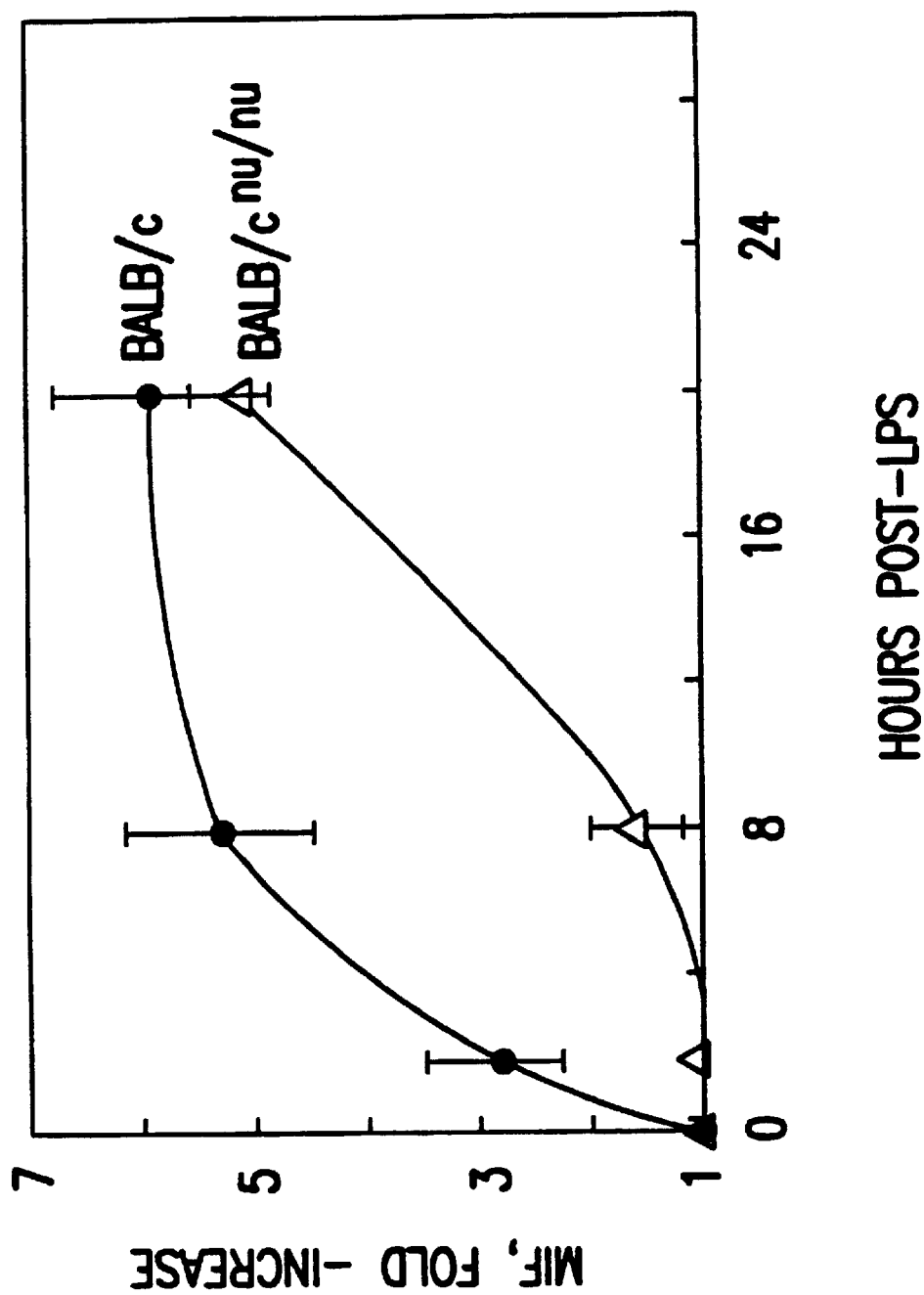

FIG. 13: Temporal analysis of MIF levels, in sera of mice treated with LPS.

Figures 14A, 14B:
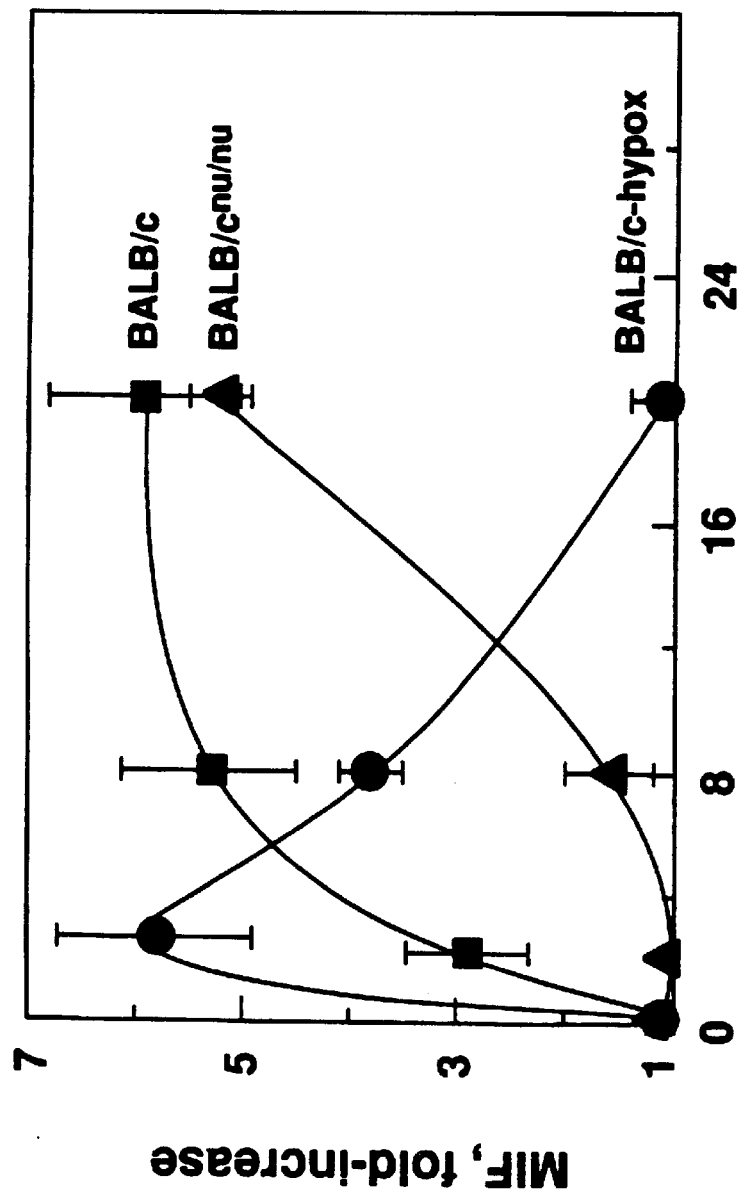

FIG. 14: Western blotting and densitometric analysis of serum MIF in BALB/c, BALB/c$^{nu/nu}$, and hypophysectomized BALB/c mice. Mice were injected i.p. with LPS and blood sampled at intervals for Western blotting analysis. The content of MIF in serum aliquots (5 μl) was quantified by laser densitometry with reference to electrophoresed rMIF standards. The inset shows the MIF blot for the BALB/c mice, demonstrating the time-dependent increase in serum MIF after LPS administration. Each plotted point is the mean±SEM of individual sera from 2 to 5 animals.

Figure 15:
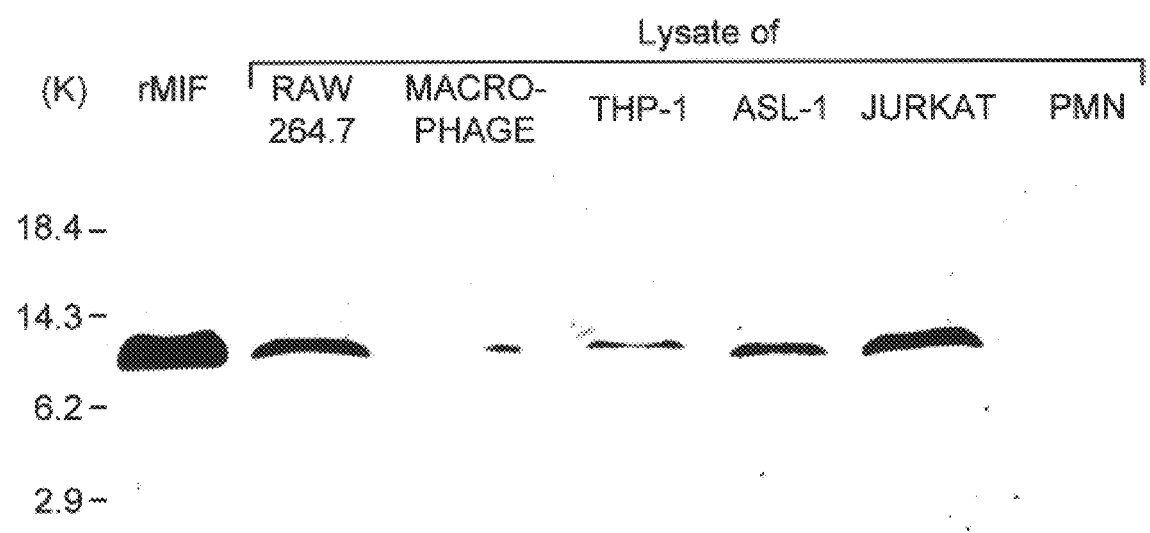

FIG. 15: Western blotting analysis of the MIF content of non-stimulated monocytes/macrophages, T-lymphocytes, and PMNs. Ten μl of cell lysate (equivalent to $5\times10^3$ cells) were electrophoresed through 18% gels, transferred to nitrocellulose membrane, and analyzed with anti-MIF polyclonal antibody. 30 ng of rMIF was electrophoresed and transferred as a standard.

Figure 16A:
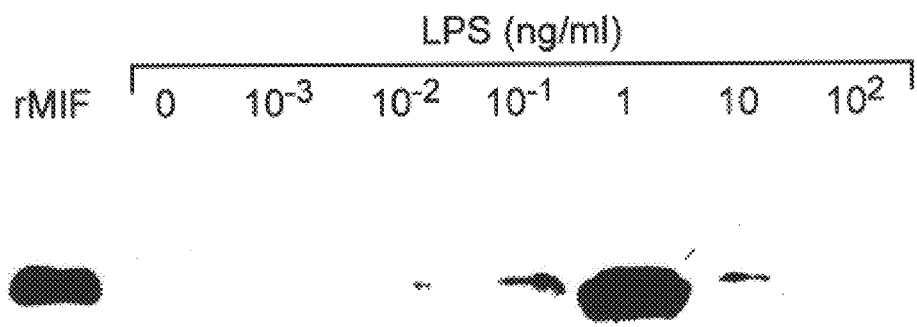
Figure 16B:
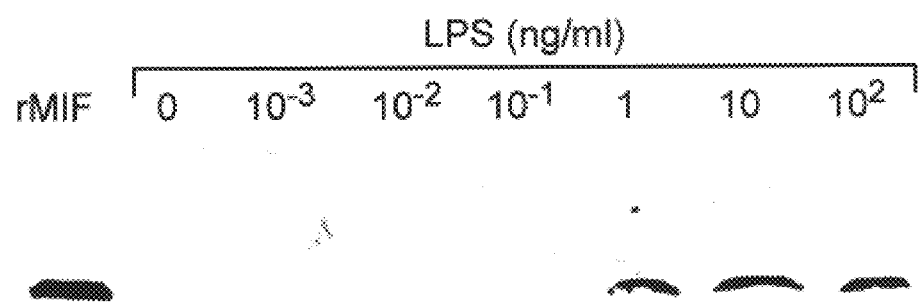
Figure 16C:
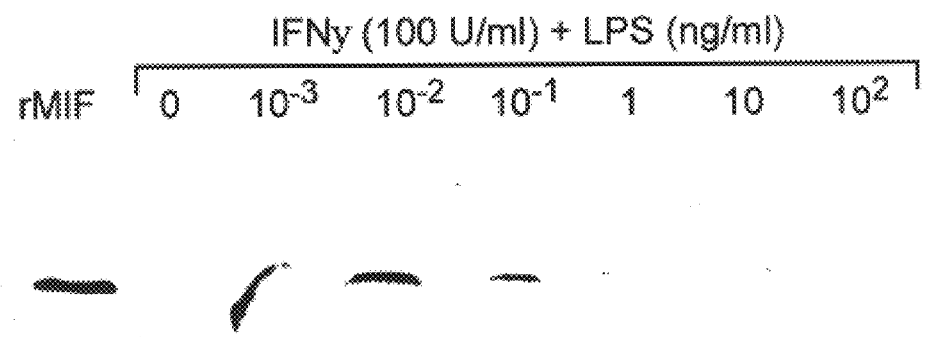

FIGS. 16A, 16B, 16C: Western blotting analysis of MIF secretion by RAW 264.7 cells (FIG. 16A) and by thioglycollate-elicited peritoneal macrophages stimulated with LPS (FIG. 16B) or with IFNγ plus LPS (FIG. 16C).

Macrophages ($4\times10^6$ RAW 264.7 cells or $1\times10^7$ peritoneal macrophages) were incubated for 12 h with LPS or IFNγ plus LPS at the indicated concentrations. The content of MIF secreted into the medium was analyzed by Western blotting. rMIF (30 ng in panel A and 20 ng in panels B and C) was electrophoresed and transferred as a standard.

Figure 17:
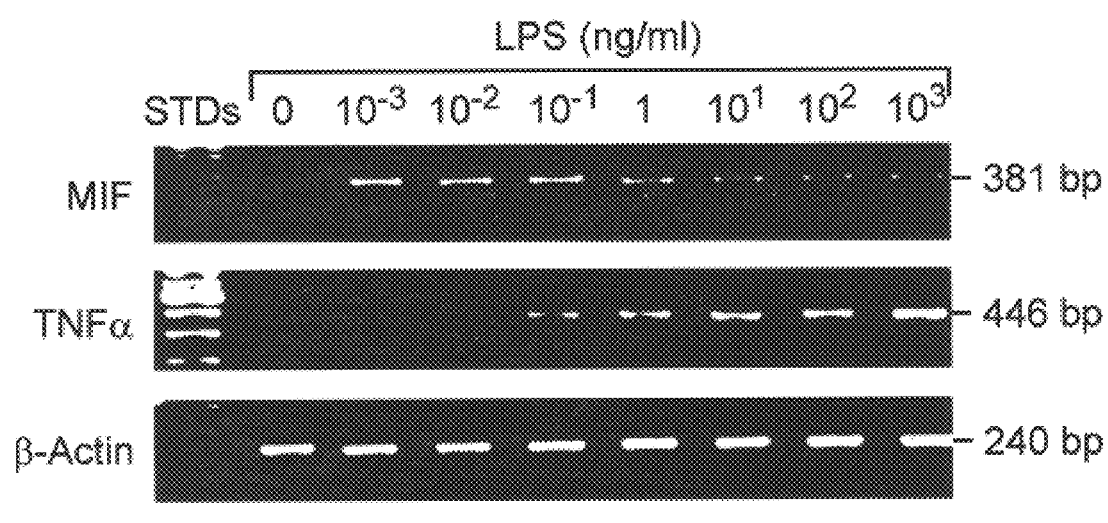

FIG. 17: RT-PCR analysis of MIF, TNFα, and β-actin expression by LPS-stimulated RAW 264.7 macrophages. Cells ($4\times10^6$) were incubated for 12 h in medium containing RPMI/1% FBS and LPS at the indicated concentrations. Total cellular RNA was extracted, CDNA prepared, and gene-specific PCR products analyzed by agarose gel electrophoresis as described in Materials and Methods.

Figure 18:
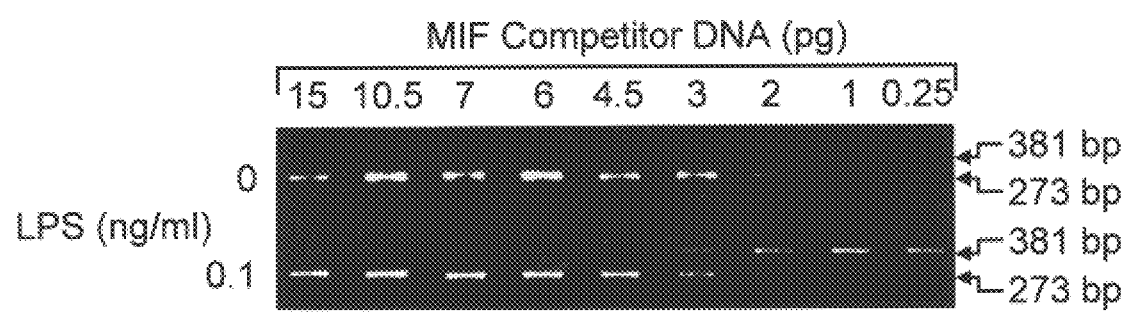

FIG. 18: Competitive PCR analysis of macrophage MIF mRNA after LPS stimulation. RAW 264.7 cells ($4\times10^6$) were incubated for 12 h in RPMI/1% FBS with or without LPS (100 pg/ml). RNA was extracted and MIF mRNA levels analyzed as described in Material and Methods. The amount of MIF competitor template DNA ranged from 0.25 to 15 pg per reaction as shown.

Figure 19:
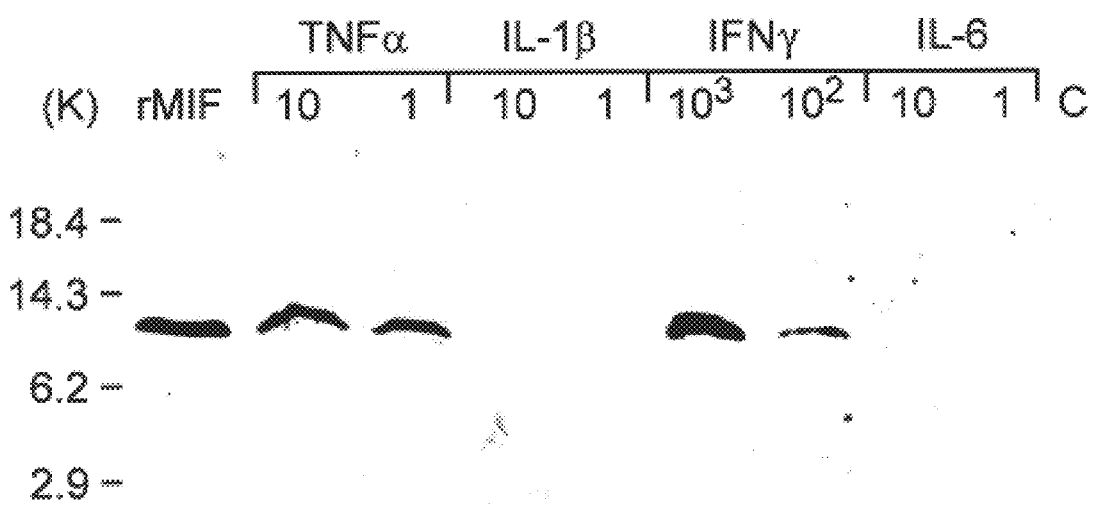

FIG. 19: Western blotting analysis of cytokine-induced MIF secretion by RAW 264.7 macrophages. Cells ($4\times10^6$) were incubated for 12 h with TNFα, IL-1β, IL-6 (10 or 1 ng/ml), or IFNγ (1000 or 100 IU/ml). 20 ng of rMIF was electrophoresed and transferred as a standard.

Figure 20:
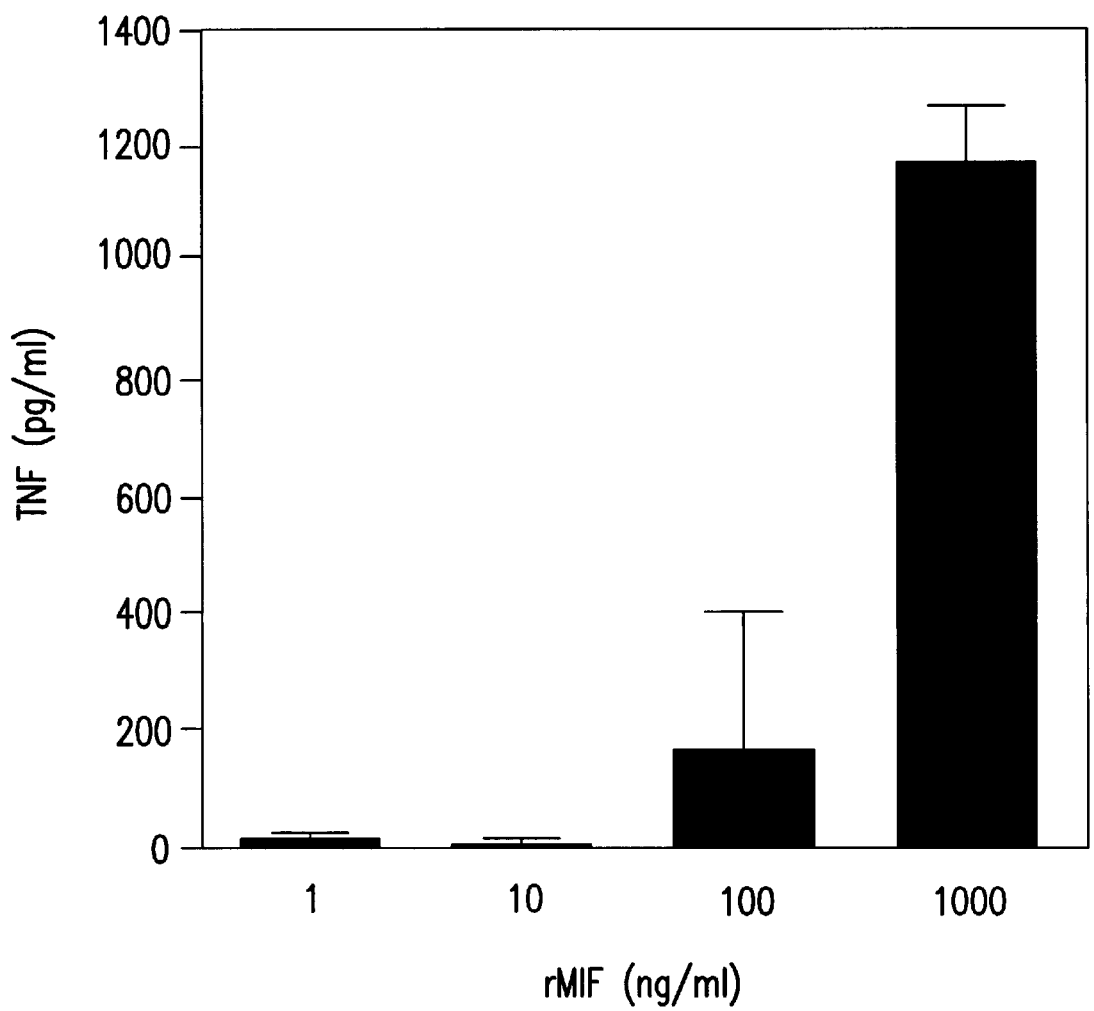

FIG. 20: Concentration of TNFα in cell-culture supernatants of RAW 264.7 macrophages stimulated with rMIF. Cells ($4\times10^6$) were incubated for 12 h with the indicated concentrations of rMIF or with medium alone (control). Culture medium then was removed and the TNFα content quantified by L929 cell cytotoxicity. TNFα concentration is expressed as the difference between the level produced by rMIF-stimulated cells and by control (non-stimulated) cells. Data are expressed as the mean±SD of three separate experiments.

Figure 21A:
Figure 21B:
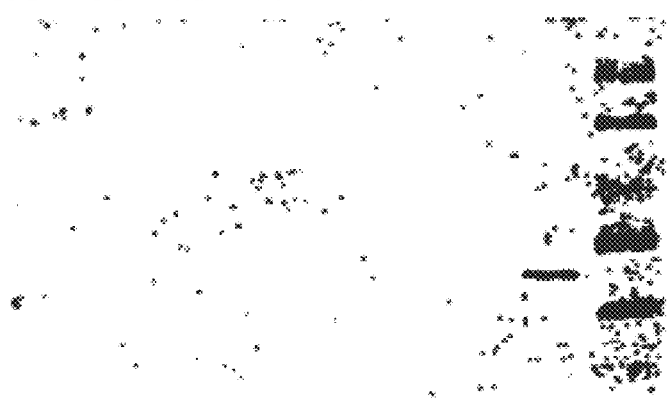

FIG. 21: Western blotting analysis of the inhibition by 20α-dihydrocortisol of the MIF response of RAW macrophages to dexamethasone.

Figure 22:
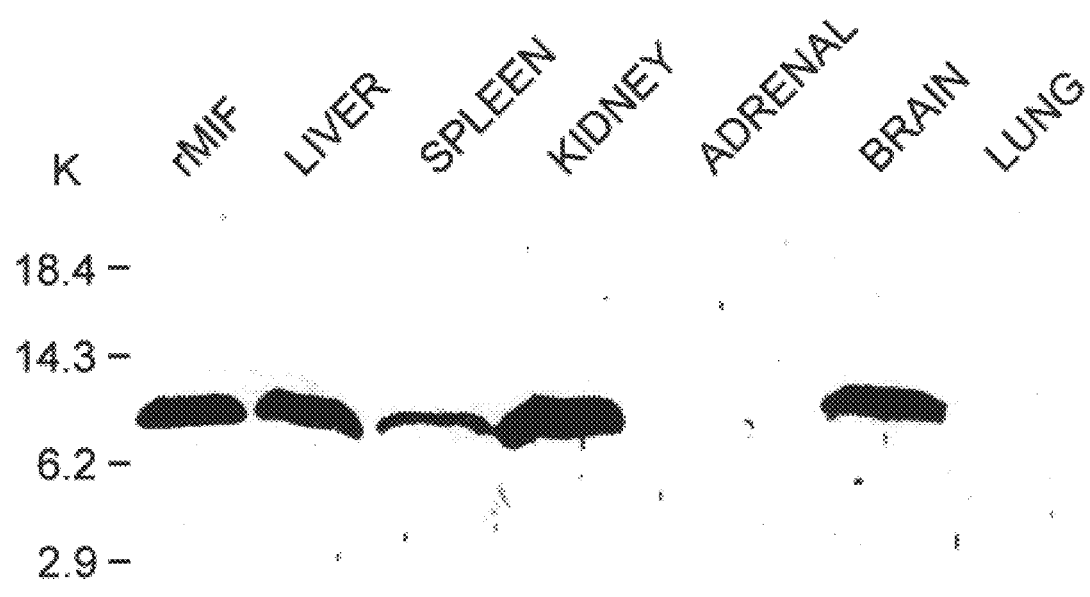

FIG. 22: Western blotting analysis of the organ distribution of murine MIF protein. Organs were obtained from an untreated BALB/c mouse. Aliquots (60 μg of protein) of liver, spleen, kidney, adrenal, brain and lung lysates were electrophoresed through 18% gels, transferred to nitrocellulose membrane, and analyzed with anti-MIF polyclonal antibody. 20 ng of rMIF was electrophoresed and transferred as a standard. Although not visible, a MIF band of much lower intensity also was detected in the adrenals and lungs.

5. DETAILED DESCRIPTION OF THE INVENTION

The present invention involves compositions and methods that inhibit MIF release and/or activity in vivo, for the treatment of any conditions involving cytokine-mediated toxicity, which include but are not limited to shock, including endotoxin-induced septic shock and exotoxin-induced toxic shock, inflammation, graft versus host disease, autoimmune diseases, acute respiratory distress syndrome, granulomatous diseases, chronic infections, transplant rejection, cachexia, viral infections, parasitic infections, including for instance malaria, and/or bacterial infections.

The inhibition of MIF activity in accordance with the invention may be accomplished in a number of ways, which may include, but are not limited to, the use of factors which bind to MIF and neutralize its biological activity; the use of MIF-receptor antagonists; the use of compounds that inhibit the release of MIF from cellular sources in the body; and the use of nucleotide sequences derived from MIF coding, non-coding, and/or regulatory sequences to prevent or reduce MIF expression. Any of the foregoing may be utilized individually or in combination to inhibit MIF activity in the treatment of the relevant conditions, and further, may be combined with any other anti-cytokine therapy (including steroid therapy), anti-initiator therapy, inhibitory cytokines or any combination thereof.

5.1. MIF is a Critical Mediator in the Shock Syndrome and Integrates Central and Peripheral Inflammatory Responses MIF is identified herein as both a neuroendocrine mediator and a macrophage cytokine which plays an important role in host inflammatory responses to infection and tissue invasion. Upon release after a proinflammatory stimulus, macrophage-derived MIF may act together with TNFα and other cytokines to coordinate local cellular responses against infection or tissue invasion. Pituitary-derived MIF, however, may serve to prime systemic immune responses once a localized inflammatory site fails to contain an invasive agent, or else act as a CNS-derived stress signal to activate the immune system against invasion. Thus, MIF may act in concert with adrenocorticotrophic hormone (ACTH) and the adrenocortical axis to modulate systemic inflammatory responses.

The working examples described infra, demonstrate that MIF, historically considered to be a product of activated T-lymphocytes, is also produced by the pituitary and macrophages (see Section 11 and 12; infra); that MIF plays a critical role in endotoxin-induced septic shock (caused by gram negative organisms; see Section 7, infra), exotoxin-induced toxic shock syndrome (caused by gram positive organisms; see Section 8, infra), parasite-induced disease responses (see Section 9, infra), and non-infectious inflammatory diseases, e.g., involving the cell-mediated immune response (see Section 10, infra); and that MIF acts in concert with glucocorticoids to regulate inflammation and immunity (see Section 13, infra); and that MIF plays a role in the development of a primary immune response (see Section 16, infra). In particular, the results show that MIF potentiates lethality of endotoxemia, whereas the inhibition of MIF confers protection against lethal endotoxemia. Inhibition of MIF similarly confers protection against toxic shock syndrome. Surprisingly, MIF is induced by many of the glucocorticoids that are considered to be anti-inflammatory agents.

The experiments in animals described herein indicate that a dominant role of MIF is to serve as a proinflammatory mediator. A proinflammatory spectrum of action for MIF has been verified by in vitro studies described herein. As shown in Section 6, infra, recombinant (rMIF) was found to induce TNFα secretion by macrophages, indicating that MIF and TNFα may act locally in a reciprocal, proinflammatory loop, i.e., MIF and TNFα stimulate the production of each other by cells of the immune system. Recombinant MIF, in combination with other proinflammatory stimuli, e.g., IFN-γ, also promotes murine macrophage nitric oxide (NO) synthesis (see Section 6, infra).

The Applicants have found that the resting pituitary contains large stores of preformed MIF which are released into the circulation after activation of the hypothalamic-pituitary axis by endotoxin, but not from pituicytes by several other cytokines which participate in the proinflammatory response, such as TNFα, IL-1β, IL-6 or IFN-γ (see Section 11, infra). MIF is also released by macrophages in response to low doses of endotoxin, and in response to TNFα and IFN-γ (see Section 12, infra), in response to parasitic infection (see Section 9 infra), and in response to steroids (see Section 13, infra). Thus, the macrophage is not only a target for MIF, but is also an important source of MIF in vivo.

FIG. 1 depicts the profile of endotoxin-induced MIF and TNFα serum concentrations detected during the shock response. Detectable serum concentrations of TNFα quickly peak and clear within 1–2 hours of exposure to endotoxin. In contrast, detectable serum concentrations of MIF gradually increase during the acute phase (1–8 hours), peak at 8 hours and persist during the post-acute phase (>8 hours) for up to 20 hours. While not limited to any theory of operation, the following cellular sources are proposed for the serum concentrations of MIF observed, based on the data presented in Sections 11 and 12 infra, and FIGS. 13 and 14: MIF is probably produced by activated T-cells and macrophages during the proinflammatory stage of endotoxin-induced shock, e.g., as part of the localized response to infection. Once released by a pro-inflammatory stimulus, e.g., low concentrations of LPS, or by TNFα and IFN-γ (but not IL-1β or IFN-γ), macrophage-derived MIF is the probable source of MIF produced during the acute phase of endotoxic shock. Both the pituitary, which releases MIF in response to LPS (but not INF-α, IL-1β, IL-6 or IFN-γ), and macrophages are the probable source of MIF in the post-acute phase of endotoxic shock, when the infection is no longer confined to a localized site.

In view of Applicants' discovery that the pituitary is a source of MIF, the notion that hypophysectomy sensitizes experimental animals to the lethal effects of LPS initially suggested that MIF may act to down-regulate host inflammatory responses. Therefore, it was surprising to find that purified, recombinantly prepared MIF (rMIF), when injected in mice produced visible symptoms of endotoxemia, and when co-injected with LPS, potentiated lethality in mice. E.g., see the results presented in the working example in Section 7, infra, which demonstrate that MIF substantially amplifies endotoxin-induced mortality of animals. Thus, contrary to what was expected, it is shown herein that an increase in MIF is not beneficial to the host system, and, in fact, appears to exacerbate cytokine-mediated conditions such as septic shock. The results also show that MIF is induced by toxic shock syndrome toxin-1 (TSST-1), a staphylococcal exotoxin (Section 8, infra), and by hemozoin, a specific malarial product (Section 9, infra).

It was equally surprising to discover that inhibition of MIF conferred protection against lethal toxemia. As demonstrated in the working example presented in Section 7, infra, inhibition of MIF activity leads to a dramatic increase in the cumulative survival of animals challenged with high-dose endotoxin or TNFα. Anti-MIF antiserum also markedly reduced mortality in test animals challenged with lethal doses of TSST-1 (see Section 8, infra). These data establish that MIF contributes significantly to lethality and may in this sense be considered a necessary or essential component of the shock syndrome.

In accordance with the invention, the inhibition of MIF activity and/or release may be used to treat inflammatory response and shock. Beneficial effects may be achieved by intervention at both early and late stages of the shock response. In this respect, the working examples also describe the production of monoclonal antibodies directed against both human and murine MIF, which may be used to neutralize MIF activity (see Section 17, infra).

While not limited to any theory or mechanism responsible for the protective effect of MIF inhibition, preliminary studies show that anti-MIF therapy is associated with an appreciable (up to 35–40%) reduction in circulating serum TNFα levels. This reduction is consistent with the TNFα-inducing activity of MIF on macrophages in vitro, and suggests that MIF is responsible, in part, for the extremely high peak in serum TNFα level that occurs 1–2 hours after endotoxin administration despite the fact that MIF cannot be detected in the circulation at this time. Thus, MIF inhibition therapy may be beneficial at the early stages of the inflammatory response.

MIF also plays an important role during the post-acute stage of the shock response, and therefore, offers an opportunity to intervene at late stages where other treatments, such as anti-TNFα therapy, are ineffective. The working examples described herein show that MIF is released at the post-acute stage of shock, when it is detectable in the circulation. In the experimental system used, anti-MIF therapy protected against lethal shock in animals challenged with high does of endotoxin (i.e., doses which induce release of pituitary MIF into the circulation), and in animals challenged with TNFα (i.e., where the exogenous TNFα overrides the beneficial reduction in circulating endogenous TNFα concentrations achieved using anti-MIF). The ability of anti-MIF therapy to protect animals challenged with TNFα indicates that neutralization of MIF during the later, post-acute phase of septic shock is efficacious. The protective effect of the antibody may be attributed, in part, to neutralization of pituitary and macrophage MIF released in the post-acute phase of septic shock when circulating MIF is readily detected. Because MIF is a necessary component of the shock syndrome, and the peak of serum MIF expression occurs after that of TNFα, MIF inhibitors may be used to successfully treat cytokine-mediated conditions even later than the point at which administration of TNFα inhibitors is no longer effective.

Since steroids are potent inhibitors of cytokine production, their effects were examined on MIF secretion by macrophages and pituitary cells (see Section 13, infra). Surprisingly, steroids were found to induce rather than inhibit MIF secretion by these cells. The secretion of MIF in response to steroids may reduce the benefit of steroid therapy currently used to treat inflammation. Therefore, MIF inhibition therapy may be used in conjunction with steroids to treat shock and other cytokine-mediated pathological states, particularly in chronic inflammatory states such as rheumatoid arthritis. Such combination therapy may be beneficial even subsequent to the onset of pathogenic or other inflammatory responses. For example, administration of steroids alone inhibits the TNFα response only if given simultaneously with or before LPS challenge. In the clinical setting, the administration of steroids subsequent to the onset of septic shock symptoms has proven of little benefit (Bone et al., 1987, N. Engl. J. Med. 317: 653–658; Spring et al., 1984, N. Engl. J. Med. 311: 1137–1141). Combination steroids/MIF inhibition therapy may be used to overcome this obstacle. In another example, when treating conditions such as rheumatoid arthritis, the administration of steroids alone can result in the induction of MIF, which may override the inhibitory effects of the administered steroid on the inflammatory response. In such cases, MIF inhibition therapy can be used in conjunction with steroid treatment. Therapy can be designed to inhibit MIF release and/or activity locally and/or systemically.

Finally, in yet another aspect of the invention, newly identified MIF-inhibitors are described. For example, the Applicant's have discovered that certain steroid derivatives commonly thought to be inactive or thought to block the anti-inflammatory effects of steroids ("anti-steroids") actually inhibit MIF release in response to subsequent steroid challenge. Such "inert" or "anti-steroid" compounds may be used in conjunction with anti-inflammatory steroids to treat inflammatory diseases, especially non-infectious inflammatory diseases such as autoimmunity, rheumatoid arthritis, graft versus host disease etc. In particular, the data described herein (see Section 13, infra) show that steroids, such as dexamethasone, which are commonly used to treat inflammation actually induce MIF release. The steroid-induced release of MIF occurs at dose ranges that are used in vivo to avoid side effects, e.g., severe water retention, etc. (i.e., higher doses of steroids which result in serious side effects, and lower doses of steroids which are ineffective to treat inflammation do not appear to induce MIF release). The release of MIF in response to steroid challenge can be inhibited by pretreating with a MIF-inhibiting dose of the so-called "inactive" or "anti-steroid" derivatives, such as 20α-dihydrocortisol. Because these derivatives are "inert" high doses which inhibit-MIF release should be well tolerated. The prior administration of the "inactive" compound should not induce side effects, should inhibit MIF release, and thus, may potentiate the anti-inflammatory action of the "active" steroid subsequently administered. Assays are described herein to identify additional compounds that can be used to inhibit the steroid-induced release of MIF from cellular sources in the body.

The following subsections summarize the data presented in Sections 6 through 15, infra.

5.1.1. Identification of MIF as a Pituitary Hormone

To investigate the production and release of novel pituitary products, we examined the secretory profile of the murine anterior pituitary cell line, AtT-20. These corticotrophic cells have been used widely to study ACTH release and we thought they were potentially useful cells in which to begin to investigate humoral interactions between the central nervous system (CNS), the hypothalamus and the periphery. As shown in Section 9, infra, we incubated AtT-20 cells with LPS for various time intervals and examined culture supernatants by SDS-PAGE. These analyses revealed the specific release by pituitary cells of an apparently novel 12.5 kDa protein. The 12.5 kDa protein was then isolated and determined by amino-terminal sequencing to be highly similar to an amino acid sequence predicted from a recently cloned human MIF cDNA (Weiser et al., 1989, supra). We cloned this pituitary protein from the cDNA of LPS-stimulated AtT-20 cells and showed that it is actually the murine homolog of human MIF (90% identity over 115 amino acids) (see Section 6, infra). As little as 100 pg/ml of LPS was found to induce pituitary cell secretion of MIF. However, pituitary MIF secretion was not induced by TNF-α, IL-1β, IL-6 or IFN-γ (see Section 11, infra).

Immunocytochemical analyses revealed that resting, non-stimulated pituitary cells contain significant amounts of preformed MIF. Thus, a large fraction of the MIF that is released by pituitary cells in response to LPS arises from stored, intracellular pools. Electron microscopic studies of whole mouse pituitaries labeled with immunogold-conjugated anti-MIF antibody localize MIF to granules present within corticotrophic cells. It appears that in vivo, MIF-containing granules are released either by the direct action of circulating endotoxin or by specific hypothalamic releasing factor(s).

In vivo studies in mice showed that pituitary MIF mRNA levels increase after LPS challenge and reach a plateau after 16–24 hours. Over the same time course, the pituitary content of preformed MIF protein decreases to almost undetectable levels. To determine whether the release of pituitary MIF is associated with a concomitant rise in serum MIF, we obtained blood samples from LPS-injected mice and analyzed serum for MIF content by western blotting. In normal mice, MIF was detected 2 hours after administration of LPS and its levels increased in serum over approximately 20 hours. This time course for the rise in serum MIF is consistent both with the decrease in pituitary MIF protein and with the increase in pituitary MIF mRNA that occurred after injection of LPS. In contrast, MIF in the serum of hypophysectomized mice showed a markedly different pattern of induction. Serum specimens obtained from LPS-treated, hypophysectomized mice showed no detectable MIF at 20 hours, the time at which serum MIF levels were highest in normal mice. These data are consistent with the notion that the pituitary is critical to the MIF response that appears in serum during endotoxemia, and that pituicytes contribute to serum levels of MIF. We then calculated the amount of preformed MIF stored in the pituitary and the amount of MIF that appears in serum after activation by LPS of the hypothalamic-pituitary axis. The quantities of MIF present in the pituitary and in serum were well within the range observed for ACTH and other anterior pituitary hormones (Table I).

TABLE I

COMPARISON OF PITUITARY MACROPHAGE MIGRATION INHIBITORY FACTOR (MIF) CONTENT AND SERUM MIF LEVELS WITH LEVELS OF OTHER ANTERIOR PITUITARY HORMONES

| Hormone | Pituitary content[a] (% of total protein) | Serum level[b] (ng ml$^{-1}$) |
|---|---|---|
| MIF | 0.05 | 80–340 |
| ACTH | 0.2 | 2–500 |
| Prolactin | 0.08 | 200–300 |

[a]Pituitary hormone content at resting conditions.
[b]Serum hormone level under conditions of maximal pituitary stimulation.

5.1.2. Macrophage MIF Production

As shown in Section 12, infra, hypophysectomized mice have a markedly abnormal serum MIF response compared with control mice. The gradual increase in serum MIF over 20 hours is not observed. Instead, on closer examination, a peak of serum MIF is observed during the early, acute phase of endotoxaemia ($\leq$3 h after LPS injection). Given the lack of a pituitary in hypophysectomized mice, and the well-accepted unresponsiveness of T cells to LPS, we considered that the MIF present in the circulation at 2 hours must reflect the release of this cytokine by an additional LPS-sensitive cell population. Based on the observation that such an early peak in the serum MIF response is reminiscent of a macrophage TNFα response, we examined the possibility that MIF is also produced by cells of the monocyte-macrophage lineage.

Significant amounts of preformed MIF protein were found in the resting, nonstimulated murine monocyte cell line RAW 264.7, murine peritoneal macrophages and the human monocyte cell line THP-1. Western blotting revealed that the MIF content of murine or human monocytes-macrophages was similar to that of the murine ASL-1 and the human Jurkat T cell lines. In contrast, cell lysates obtained from purified polymorphonuclear leukocytes did not contain detectable MIF protein. Whole tissue analyses demonstrated significant amounts of both MIF protein and mRNA in organs that have a high content of macrophages (see Section 14, infra), complementing recent observations that MIF mRNA is present constitutively in tissues such as the spleen, the liver, and the kidney. (Lanahan et al., 1992, Mol. Cell. Biol. 12: 3919–3929).

Various proinflammatory stimuli, such as LPS, TNFα and IFN-γ were observed to be potent inducers of macrophage MIF release (see Section 12, infra). Secretion of significant amounts of MIF occurred at LPS concentrations (10–100 pg ml$^{-1}$) that are lower in general than has been observed to be optimal for the induction of TNFα release. Significant amounts of preformed MIF mRNA were also present in resting macrophages, and stimulation by LPS increased these mRNA levels approximately two-fold. Peak mRNA stimulation also occurred at very low concentrations of LPS (1 pg ml$^{-1}$).

5.1.3. Cloning, Expression and Biochemical Characterization of MIF

The cloning of murine MIF (muMIF) from an anterior pituitary cell line and the purification of native MIF from mouse liver are described in Section 6, infra. For comparison purposes, human MIF (huMIF) was cloned from the Jurkat T-cell line. Sequence analysis of murine pituitary MIF and human T-cell MIF cDNA demonstrated a 90% homology between the murine and human proteins. Cloned Jurkat T-cell MIF cDNA differs by one nucleotide from the first published human T-cell MIF cDNA (Weiser et al., 1989), but is in agreement with human MIF cDNA derived from human lens tissue (Wistow et al., 1993, Proc. Natl. Acad. Sci. USA 90: 1272–1275), and with a T-cell glycosylation inhibition factor (GIF) cDNA (Mikayama et al., 1993, Proc. Natl. Acad. Sci. USA 90: 10056–10060). The single nucleotide difference results in a change in the deduced amino acid sequence (Ser 106→Asn 106), thus increasing homology of the human and murine proteins.

DNA homology analysis showed that both human and murine MIF lack a conventional N-terminal leader sequence. Thus, MIF joins a growing list of cytokines, such as IL-1 (Rubartelli et al., 1990, EMBO J. 9: 1503–1510), basic fibroblast growth factor (bFGF; Jackson et al., 1992, Proc. Natl. Acad. Sci. USA 89: 10691–10695), and a secreted form of cyclophilin (Sherry et al., 1992, Proc. Natl. Acad. Sci. USA 89: 3511–3515) which are released from cells by non-classical protein secretion pathways.

Recombinant murine and human MIF were expressed in *E. coli*, purified to homogeneity by a simple two-step procedure, and the proteins characterized by a variety of biochemical and biological criteria. Native MIF obtained from mouse liver was found to be monomeric and to be free of significant post-translational modifications as assessed both by endoglycosidase F treatment followed by SDS-PAGE/Western blotting and by mass spectroscopic analysis. Recombinant and native MIF exhibited a number of comparable effects on monocytes/macrophages. Recombinant MIF was found to inhibit monocyte migration when assayed in modified Boyden chambers. MIF also induced TNFα secretion, and promoted the release of nitric oxide (NO)

from macrophages primed with IFN-γ. Circular dichroism (CD) spectroscopy revealed that bioactive, recombinant MIF exhibits a highly ordered three-dimensional structure, with a >55% content of β-pleated sheet and α-helix. Thermodynamic stability studies also showed that despite a high content of ordered secondary structure elements, the conformation of MIF was readily perturbed by denaturing solvent conditions. These studies define a number of the biochemical and biological properties of recombinant and purified, native MIF and provide, for the first time, information concerning the three-dimensional structure of this protein.

5.1.4. Biodistribution of MIF and MIF Receptors

The working example in Section 14, infra, presents a study that illustrates, the distribution of MIF and MIF-binding sites, i.e. MIF-receptors within the body. The study indicates that MIF receptors are present in kidney cells, for example. Further, two such MIF receptors are identified, for the first time, in the working example presented, infra, in Section 13. Such receptors may be genetically engineered for use as MIF inhibitors.

5.2. Inhibitors of MIF Activity

Described below are factors which may be used as MIF antagonists, i.e., factors which inhibit the biologic activity of MIF.

5.2.1. MIF-binding Partners

Factors that bind MIF and neutralize its biological activity, hereinafter referred to as MIF binding partners, may be used in accordance with the invention as treatments of conditions involving cytokine-mediated toxicity. While levels of MIF protein may increase due to endotoxin challenge, the interaction of inhibitory MIF-binding partners with MIF protein prohibits a concomitant increase in MIF activity. Such factors may include, but are not limited to anti-MIF antibodies, antibody fragments, MIF receptors, and MIF receptor fragments.

Various procedures known in the art may be used for the production of antibodies to epitopes of recombinantly produced (e.g., using recombinant DNA techniques described infra), or naturally purified MIF. Neutralizing antibodies, i.e. those which compete for or sterically obstruct the binding sites of the MIF receptor are especially preferred for diagnostics and therapeutics. Such antibodies include but are not limited to polyclonal, monoclonal, chimeric, single chain, Fab fragments and fragments produced by an Fab expression library.

For the production of antibodies, various host animals may be immunized by injection with MIF and/or a portion of MIF. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to MIF may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce MIF-specific single chain antibodies.

The hybridoma technique has been utilized to generate anti-MIF monoclonal antibodies. Hybridomas secreting IgG monoclonal antibodies directed against both human and murine forms of MIF have been isolated and characterized for their ability to neutralize MIF biological activity. Anti-MIF monoclonal antibodies were shown to inhibit the stimulation of macrophage-killing of intracellular parasites. The anti-MIF monoclonal antibodies have also been utilized to develop a specific and sensitive ELISA screening assay for MIF. Both the anti-MIF monoclonal antibodies and the ELISA assay may be used in the diagnosis and/or treatment of inflammatory responses and shock.

Antibody fragments which recognize specific MIF epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to MIF.

MIF receptors, MIF receptor fragments, and/or MIF receptor analogs may, in accordance with the invention, be used as inhibitors of MIF biological activity. By binding to MIF protein, these classes of molecules may inhibit the binding of MIF to cellular MIF receptors, thus disrupting the mechanism by which MIF exerts its biological activity. Small organic molecules which mimic the activity of such molecules are also within the scope of the present invention.

MIF receptors may include any cell surface molecule that binds MIF in an amino acid sequence-specific and/or structurally-specific fashion. Such MIF receptors include, but are not limited to the 72 kD MIF receptor class having a partial amino acid sequence of:

AKKGAVGGI and the 52 kD receptor having a partial amino acid sequence of:

I-X-HNTVATEI(S)(G)YN(N/G)A(M)

both of which are presented in the working example in Section 13, infra. The residues in parenthesis are provisional assignment.

Additional MIF receptors and genes that encode MIF receptors may be identified, isolated, and cloned using a variety of techniques well known to those of ordinary skill in the art. For example, MIF receptor molecules may be identified and isolated using standard affinity chromatography techniques wherein those molecules exhibiting sequence- and/or structural binding specificity to MIF protein are separated from other non-MIF binding molecules. The MIF binding proteins may be additionally purified, using standard techniques, at which point the protein may be tested and utilized for its ability to inhibit MIF.

Alternatively, the amino acid sequence of the purified protein may be at least partially determined, and then used to design oligonucleotides with which to screen cDNA and/or genomic libraries in order to clone the gene(s) that encode(s) MIF receptors, techniques of which are well known to those of skill in the art. Further, new MIF receptor genes may be cloned by construction of a cDNA library in a mammalian expression vector such as pcDNA1, that contains SV40 origin of replication sequences which permit high copy number expression of plasmids when transferred into COS cells. The expression of the MIF receptor on the surface of transfected COS cells may be detected in a number of ways, including the use of radioactive, fluorescent, or enzymatically labeled MIF. Cells expressing an MIF receptor may be enriched by subjecting transfected cells to a FACS (fluorescent activated cell sorter). For a review of cloning strategies which may be used, see e.g., Maniatis, 1989, Molecular Cloning, A Laboratory Manual, Cold Springs Harbor Press, New York; and Ausubel et al., 1989, Current Protocols in Molecular Biology, (Green Publishing Associates and Wiley Interscience, New York)

Fragments of any of the MIF receptors described above may also be used as MIF inhibitory agents, and any MIF receptor fragment possessing any amino, carboxy, and/or internal deletion that specifically binds MIF so as to inhibit MIF biological activity is intended to be within the scope of this invention. An amino and/or carboxy deletion refers to a molecule possessing amino and/or carboxy terminal truncations of at least one amino acid residue. An internal deletion refers to molecules that possess one or more non-terminal deletions of at least one amino acid residue. Among these MIF receptor fragments are truncated receptors in which the cytoplasmic or a portion of the cytoplasmic domain has been deleted, and fragments in which the cytoplasmic and the transmembrane domain(s) has been deleted to yield a soluble MIF receptor containing all or part of the MIF receptor extracellular domain.

MIF receptor analogs which specifically bind MIF may also be used to inhibit MIF activity. Such MIF receptor analogs may include MIF receptor or receptor fragments further possessing one or more additional amino acids located at the amino terminus, carboxy terminus, or between any two adjacent MIF receptor amino acid residues. The additional amino acids may be part of a heterologous peptide functionally attached to all or a portion of the MIF receptor protein to form a MIF receptor fusion protein. For example, and not by way of limitation, the MIF receptor, or a truncated portion thereof, can be engineered as a fusion protein with a desired Fc portion of an immunoglobulin. MIF receptor analogs may also include MIF receptor or MIF receptor fragments further possessing one or more amino acid substitutions of a conservative or non-conservative nature. Conservative amino acid substitutions consist of replacing one or more amino acids with amino acids of similar charge, size, and/or hydrophobicity characteristics, such as, for example, a glutamic acid (E) to aspartic acid (D) amino acid substitution. Non-conservative substitutions consist of replacing one or more amino acids with amino acids possessing dissimilar charge, size, and/or hydrophobicity characteristics, such as, for example, a glutamic acid (E) to valine (V) substitution.

The MIF receptors, MIF receptor fragments and/or analogs may be made using recombinant DNA techniques. Here, the nucleotide sequences encoding the peptides of the invention may be synthesized, and/or cloned, and expressed according to techniques well known to those of ordinary skill in the art. See, for example, Ausubel, F. M. et al., eds., 1989, Current Protocols In Molecular Biology, Vol. 1 and 2, John Wiley and Sons, New York. Caruthers, et al., 1980, Nuc. Acids Res. Symp. Ser. 7:215–233; Crea and Horn, 1980, Nuc. Acids Res. 9(10):2331; Matteucci and Caruthers, 1980, Tetrahedron Letters 21:719; and Chow and Kempe, 1981, Nuc. Acids Res. 9(12):2807–2817.

Alternatively, the protein itself could be produced using chemical methods to synthesize the amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W.H. Freeman and Co., New York pp. 50–60.) The composition of the synthetic peptides may be confirmed by amino acid analysis or sequencing (e.g., the Edman degradation procedure; see Creighton, 1983, Proteins, Structures and Molecular Principles, W.H. Freeman and Co., New York, pp. 34–49).

These molecules may also be synthesized utilizing alternative procedures which may advantageously affect certain of the molecules' properties, such as stability, bioavailability, and MIF inhibitory activity. For example, MIF receptors, MIF receptor fragments, and MIF receptor analogs may be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few. In another embodiment, the proteins may be synthesized with additional chemical groups present at their amino and/or carboxy termini. For example, hydrophobic groups such as carbobenzoxyl, dansyl, or t-butyloxycarbonyl groups, may be added to the peptides' amino terminus. Further, the peptides may be synthesized such that their steric configuration is altered. For example, the D-isomer of one or more of the amino acid residues of the peptide may be used, rather than the usual L-isomer.

5.2.2. MIF-Receptor Antagonists

Molecules which inhibit MIF biological activity by binding to MIF receptors may also be utilized for the treatment of conditions involving cytokine-meditated toxicity. Such molecules may include, but are not limited to anti-MIF receptor antibodies and MIF analogs.

Anti-MIF receptor antibodies may be raised and used to neutralize MIF receptor function. Antibodies against all or any portion of a MIF receptor protein may be produced, for example, according to the techniques described in Section 5.2.1., supra.

MIF analogs may include molecules that bind the MIF receptor but do not exhibit biological activity. Such analogs compete with MIF for binding to the MIF receptor, and, therefore, when used in vivo, may act to block the effects of MIF in the progress of cytokine-mediated toxicity. A variety of techniques well known to those of skill in the art may be used to design MIF analogs. The coding sequence for human MIF described herein, differs from the published sequence, resulting in a serine to asparagine change in the gene product at amino acid residue number 106. Both the corrected human sequence and that of the murine protein is described in Section 6, infra, and shown in FIG. 2. Recombinant DNA techniques may be used to produce modified MIF proteins containing, for example, amino acid insertions, deletions and/or substitutions which yield MIF analogs with receptor binding capabilities, but no biological activity. Alternatively, MIF analogs may be synthesized using chemical methods such as those described above in Section 5.2.1. (see, for example, Sambrook et al., 1989, Molecular Cloning, A Laboratory Manual, Cold Spring Harbor Press, New York).

MIF receptors and/or cell lines that express MIF receptors may be used to identify and/or assay potential MIF antagonists. For example, one method that may be pursued in the identification of such MIF antagonist molecules would comprise attaching MIF receptor molecules to a solid matrix, such as agarose or plastic beads, microtiter wells, or petri dishes, using techniques well known to those of skill in the art, and subsequently incubating the attached MIF receptor molecules in the presence of a potential MIF analog or analogs. After incubating, unbound compounds are washed away, and the MIF receptor-bound compounds are recovered. In this procedure, large numbers of types of molecules may be simultaneously screened for MIF receptor-binding activity. Bound molecules may be eluted from the MIF receptor molecules by, for example, competing them away from the MIF receptor molecules with the addition of excess MIF, changing the pH or osmotic strength of the buffer or adding chaotropic agents. The binding/elution steps bring about a partial purification of the molecules of interest.

In order to continue the purification process, the eluted molecules may be further fractionated by one or more chromatographic and/or other separation techniques well known in the art until the molecule(s) of interest is (are) purified to the extent necessary. Once compounds having MIF-receptor binding capabilities are identified, the compounds may be assayed for their effects on cytokine-mediated toxicity using cell lines such as those described in this Section, or by normal experimental animal models or alternatively, by utilizing transgenic animal models such as those described in Section 5.4, infra.

Alternatively, screening of peptide libraries with recombinantly produced MIF receptors and/or MIF receptor fragments may be used to identify potential MIF analogs. Once peptides that bind MIF receptor are identified using this screening technique, their effects on cytokine-mediated toxicity may be assayed using cells lines such as those described in this Section, or alternatively, may be evaluated using normal experimental animal models or transgenic animals such as those described in Section 5.4., infra. Small organic molecules which mimic the activity of such peptides are also within the scope of the present invention.

Random peptide libraries consist of all possible combinations of amino acids, and such libraries may be attached to a suitable small particulate solid phase support and used to identify peptides that are able to bind to a given receptor (Lam, K. S. et al., 1991, Nature 354: 82–84). The screening of peptide libraries may have therapeutic value in the discovery of pharmaceutical agents that act to inhibit the biological activity of receptors through their interactions with the given receptor.

Identification of molecules that are able to bind to the MIF receptor may be accomplished by screening a peptide library with recombinant soluble MIF receptor protein. Methods for expression and purification of molecules such as MIF receptors are well known to those of skill in the art. For screening, it is preferred to label or "tag" the MIF receptor molecule. The protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label to the MIF receptor may be performed using techniques that are routine in the art.

Alternatively, MIF receptor expression vectors may be engineered to express a chimeric MIF receptor protein containing an epitope for which a commercially available antibody exists. The epitope-specific antibody may be tagged using methods well known in the art including labeling with enzymes, fluorescent dyes or colored or magnetic beads.

The "tagged" MIF receptor or receptor/conjugate is incubated with the random peptide library for 30 minutes to one hour at 22° C. to allow complex formation between MIF receptor and peptide species within the library. The library is then washed to remove any unbound MIF receptor protein. If MIF receptor has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-MIF receptor complex changes color, and can be easily identified and isolated physically under a dissecting microscope with a micromanipulator. If a fluorescent tagged MIF receptor molecule has been used, complexes may be isolated by fluorescence-activated sorting. If a chimeric MIF protein expressing a heterologous epitope has been used, detection of the peptide/MIF receptor complex may be accomplished by using a labeled epitope-specific antibody. Once isolated, the MIF receptor conjugate may be eluted off, the peptide support washed, and the identity of the peptide attached to the solid phase support determined by peptide sequencing.

MIF analogs may also be identified using cell lines that express MIF receptor. Such cell lines may be ones which naturally express the receptor, such as RAW 264.7 cells, or alternatively, cell lines that have been engineered using recombinant techniques to express MIF receptor. These cell lines may also be used to evaluate potential MIF analogs identified using MIF receptor binding techniques such as those described above.

With respect to engineered cell lines, a variety of cells may be utilized as host cells for expression of the recombinant MIF receptor, including, but not limited to animal cell systems infected with recombinant virus expression vectors (e.g., adeno-virus, vaccinia virus) including cell lines engineered to contain multiple copies of the MIF receptor DNA either stably amplified (e.g., CHO/dhfr) or unstably amplified in double-minute chromosomes (e.g., murine cell lines). In cases where an adenovirus is used as an expression vector, the MIF receptor coding sequence may be ligated to an adenovirus transcription-translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing MIF receptor in infected hosts (e.g., See Logan & Shenk, 1984, Proc. Natl. Acad. Sci. (USA) 81:3655–3659). Alternatively, the vaccinia 7.5K promoter may be used. (See, e.g., Mackett et al., 1982, Proc. Natl. Acad. Sci. (USA) 79: 7415–7419; Mackett et al., 1984, J. Virol. 49: 857–864; Panicali et al., 1982, Proc. Natl. Acad. Sci. 79: 4927–4931).

Specific initiation signals may also be required for efficient translation of inserted MIF receptor coding sequences. These signals include the ATG initiation codon and adjacent sequences. In cases where the entire MIF receptor gene, including its own initiation codon and adjacent sequences, is inserted into the appropriate expression vector, no additional transcriptional control signals may be needed. However, in cases where only a portion of the MIF receptor coding sequence is inserted, exogenous transcriptional control signals, including the ATG initiation codon, must be provided. Furthermore, the initiation codon must be in phase with the reading frame of the MIF receptor coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, and for any normal glycosylation, and/or phosphorylation of the gene product may be used. Such mammalian host cells include but are not limited to CHO, VERO, BHK, HeLa, COS, MDCK, 293, WI38, etc.

The cell lines may be utilized to screen and identify MIF analogs. Synthetic compounds, natural products, and other sources of potentially biologically active materials can be screened in a number of ways, by, for example, testing a compound's ability to inhibit binding of MIF to a MIF receptor. Standard receptor binding techniques may be utilized for this purpose.

The ability of anti-MIF receptor antibodies and potential MIF analogs to reduce or inhibit MIF biological activity may be assayed in vivo by utilizing animals expressing MIF receptor, for instance, normal animals. Such animals may also include transgenic animal models such as those escribed below in Section 5.4, infra.

5.2.3. Other Inhibitors of MIF Activity

As explained in Section 5.1, supra, certain steroids, commonly thought to be either inactive or "anti-steroidal" actually inhibit the release of MIF; e.g., 20α dihydrocortisol. These steroids, or any other compound which inhibits the release of preformed MIF, can be used in combination therapy with anti-inflammatory steroids.

Compounds which inhibit the release of MIF can be identified in cell based assays, such as the one described in Section 13, infra. In general, any pituitary or macrophage cell line that releases MIF in response to a challenge dose of steroid can be used. The assay can be conducted by adding the test compound to the cells in culture which are then challenged with a dose of steroid known to induce MIF release. Test compounds may be administered simultaneously with, or up to several hours before or after the challenge dose so as to identify agents that are useful in inhibiting the MIF response at different stages, i.e., inhibiting release of pre-formed MIF, versus inhibiting de novo synthesis and release, versus inhibiting both.

The conditioned media is then collected from the cultured cells and assayed for MIF; e.g., by immunoassay, including but not limited to an ELISA, Western blot, radioimmunoassay, etc. A reduced amount of MIF in the conditioned media indicates that the test compound inhibits the steroid-induced release of MIF. Compounds so identified in this assay may be used in combination therapy with steroids to treat inflammation. "Biologically inert" or innocuous compounds, such as the inactive steroids, or steroids which can be used at doses that do not cause undesired side effects, may be preferred for therapeutic use. However, any inhibitory compounds having a good therapeutic index, e.g., low toxicity and little or no side effects may be used.

5.2.4. Dose and Treatment Regimens

Inhibitors of MIF biological activity such as anti-MIF antibodies, MIF receptors, MIF receptor fragments, MIF receptor analogs, anti-MIF receptor antibodies, MIF analogs and inhibitors of MIF release, may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Effective concentrations and frequencies of dosages of the MIF inhibitory compounds invention to be administered may be determined through procedures well known to those in the art, which address such parameters as biological half-life, bioavailability, and toxicity. In the case of anti-MIF antibodies, a preferred dosage concentration may range from about 0.1 mg/kg body weight to about 20 mg/kg body weight, with about 10 mg/kg body weight being most preferred. Because antibodies typically exhibit long half-lives in circulation, a single administration of antiserum may be sufficient to maintain the required circulating concentration. In the case of compounds exhibiting shorter half-lives, multiple doses may be necessary to establish and maintain the requisite concentration in circulation.

MIF inhibitors may be administered to patients alone or in combination with other therapies. Such therapies include the sequential or concurrent administration of inhibitors or antagonists of initiators of cytokine-mediated toxicity (e.g. anti-LPS), inhibitors or antagonists of participants in the endogenous cytokine responses (e.g. anti-TNFα, anti-IL-1, anti-IFN-γ, IL-1 RA); and compounds that inhibit or antagonize cytokine-mediated toxicity directly (e.g. steroids, glucocorticoids or IL-10). MIF inhibitor dosage concentration and frequency may be altered when used as a part of a combination therapy and, therefore appropriate tests must be performed in order to determine the best dosage when more than one class of inhibitory compounds is to be administered.

Because MIF expression reaches a peak level in response to endotoxin challenge later than TNFα, anti-MIF compounds may be administered after the period within which anti-TNFα inhibitors are effective. As shown in the working example, described in Section 7, infra, anti-MIF antibody conferred full protection against endotoxemia in animals. Anti-MIF has also been shown in Applicants' pilot studies to reduce circulating TNFα levels, indicating that anti-MIF inhibits the proinflammatory spectrum of activity of MIF, and that anti-MIF inhibits the inflammatory cytokine cascade generally. In in vivo experiments, moreover, anti-MIF was shown to protect against lethal shock induced by administration of exogenous TNFα (see Section 7, infra). Therefore, the beneficial effect of the anti-MIF antibody probably resides in its ability to neutralize the bioactivity of both macrophage MIF released during the acute phase in response to a proinflammatory stimulus (e.g., LPS, or TNFα and IFN-γ), and MIF released by both the pituitary and macrophages during the post-acute phase of the shock response.

The development of anti-MIF monoclonal antibodies provides a specific means for disrupting the mechanism by which MIF exerts its biological activity. The anti-MIF monoclonal antibodies may be used as a therapeutic for conditions involving MIF-mediated adverse effects generally, for instance endotoxin lethality and cytokine-mediated lethality, including TNFα toxicity, such as observed during septic shock. The same antibodies may also be used to protect against the toxic effects of nitric oxide production by macrophages, which is also induced by MIF. MIF has been shown to be an important mediator in the immune response to malaria infection, therefore anti-MIF monoclonal antibodies may be effective in ameliorating the lethality of parasite-induced cytokine release. Aside from being an important mediator of the inflammatory immune response, MIF has also been shown to be involved in the development of a primary immune response. Furthermore, the administration of anti-MIF monoclonals has been shown to abrogate an antigen-specific immune response, confirming that anti-MIF antibodies may be useful therapeutic agents for substantially reducing an undesired immune reaction, such as allergy or autoimmunity.

5.3. Inhibitors of MIF and/or MIF Receptor Gene Expression

Nucleotide sequences derived from the coding, non-coding, and/or regulatory sequences of the MIF and/or MIF receptor genes may be used to prevent or reduce the expression of these genes, leading to a reduction or inhibition of MIF activity. The nucleotide sequence encoding the human MIF protein has been reported. In addition, as presented in the working example in Section 6, infra, the nucleotide sequence of human MIF has been corrected, and a cDNA corresponding to the nucleotide sequence encoding the murine MIF protein has now been identified. Further, the MIF receptor amino acid sequence provided in the working example in Section 15, infra, may, for example, be used to design oligonucleotides for the regulation of MIF receptor genes. Among the techniques by which such regulation of gene expression may be accomplished are, as described below, antisense, triple helix, and ribozyme approaches. Administration of these nucleotide sequences, therefore, may be used to temporarily block expression and/or transcription of the MIF and/or MIF receptor genes as one method of treatment for conditions involving cytokine-mediated toxicity.

These approaches which target gene expression may be used alone, in combination with each other, or alternatively, in conjunction with any of the inhibitory MIF-binding and/or MIF receptor antagonist procedures described above. Further, these gene regulation approaches may be used together with anti-TNFα, anti-initiators and/or other anti-cytokine therapies.

5.3.1. Anti-sense RNA and Ribozymes

Within the scope of the invention are oligo-ribonucleotide sequences, that include anti-sense RNA and DNA molecules and ribozymes that function to inhibit the translation of MIF and/or MIF receptor mRNA. Anti-sense RNA and DNA molecules act to directly block the translation of mRNA by binding to targeted mRNA and preventing protein translation, either by inhibition of ribosome binding and/or translocation or by bringing about the nuclease degradation of the mRNA molecule itself.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of MIF and/or MIF receptor mRNA sequences.

Specific ribozyme cleavage sites within any potential RNA target are initially identified by scanning the target molecule for ribozyme cleavage sites which include the following sequences, GUA, GUU and GUC (See FIG. 2 for an illustration of such potential sites on murine and human MIF cDNA). Once identified, short RNA sequences of between 15 and 20 ribonucleotides corresponding to the region of the target gene containing the cleavage site may be evaluated for predicted structural features such as secondary structure that may render the oligo-nucleotide sequence unsuitable. The suitability of candidate targets may also be evaluated by testing their accessibility to hybridization with complimentary oligonucleotides, using ribonuclease protection assays.

Both anti-sense RNA and DNA molecules and ribozymes of the invention may be prepared by any method known in the art for the synthesis of nucleic acid molecules. These include techniques for chemically synthesizing oligodeoxyribonucleotides well known in the art such as, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.3.2. Triplex DNA Formation

Oligodeoxyribonucleotides can form sequence-specific triple helices by hydrogen bonding to specific complementary sequences in duplexed DNA. Interest in triple helices has focused on the potential biological and therapeutic applications of these structures. Formation of specific triple helices may selectively inhibit the replication and/or gene expression of targeted genes by prohibiting the specific binding of functional trans-acting factors.

Oligonucleotides to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Oligonucleotide sequences may be pyrimidinebased, which will result in TAT and CGC triplets across the three associated strands of the resulting triple helix. The pyrimidine-rich oligonucleotides provide base complementarity to a purine-rich region of a single strand of the duplex in a parallel orientation to that strand. In addition, oligonucleotides may be chosen that are purine-rich, for example, containing a stretch of G residues. These oligonucleotides will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation may be increased by creating a so called "switchback" oligonucleotide. Switchback oligonucleotides are synthesized in an alternating 5'-3',3'-5' manner, such that they base pair with first one strand of a duplex and then the other, eliminating the necessity for a sizeable stretch of either purines or pyrimidines to be present on one strand of a duplex.

5.3.3. Administration of Oligonucleotides

For anti-MIF therapeutic uses, the inhibitory oligonucleotides may be formulated and administered through a variety of means, including systemic, and localized, or topical, administration. Techniques for formulation and administration may be found in "Remington's Pharmaceutical Sciences," Mack Publishing Co., Easton, Pa., latest edition. The mode of administration may be selected to maximize delivery to a desired target organ in the body. For example, $^{125}$I-MIF binding studies detailed in Section 12, infra, indicate that MIF is preferentially distributed to the liver and kidney. Therefore, oligonucleotides designed to inhibit expression of the MIF-receptor may be formulated for targeting to these organs; in this regard, liposome-encapsulated oligonucleotides may prove beneficial. Alternatively, MIF itself is produced in T cells and macrophages and, in response to endotoxin induction, in the pituitary. Therefore, oligonucleotides designed to inhibit the expression of MIF should be formulated for targeting to these organs.

For systemic administration, injection is preferred, including intramuscular, intravenous, intraperitoneal, and subcutaneous. For injection, the oligonucleotides of interest are formulated in aqueous solutions, preferably in physiologically compatible buffers such as Hanks's solution, Ringer's solution, or physiological saline buffer. In addition, the oligonucleotides may be formulated in solid or lyophilized form, then redissolved or suspended immediately prior to use. Systemic administration may also be accomplished by transmucosal, transdermal, or oral means. For transmucosal or transdermal administration, penetrants appropriate to the barrier to be permeated are used in the formulation. Such penetrants are generally known in the art. Transmucosal administration may be through nasal sprays or suppositories. For oral administration, oligonucleotides may be formulated into capsules, tablets, and tonics. For topical administration, the oligonucleotides of the invention are formulated into ointments, salves, gels, or creams, as is generally known in the art.

Alternatively, the oligonucleotides of the invention may first be encapsulated into liposomes, then administered as described above. Liposomes are spherical lipid bilayers with aqueous interiors. All molecules that are present in an aqueous solution at the time of liposome formation (in this case, oligonucleotides) are incorporated into this aqueous interior. The liposomal contents are both protected from the external microenvironment and, because liposomes fuse with cell membranes, are efficiently delivered into the cell cytoplasm, obviating the need to neutralize the oligonucleotides' negative charge.

The introduction of oligonucleotides into organisms and cells for such purposes may be accomplished by several means. For mammalian administration, each of the techniques described above for therapeutic oligonucleotide purposes may be used. In addition, other standard techniques for introduction of nucleic acids into cells, including, but not limited to, electroporation, microinjection, and calcium phosphate precipitation techniques may be utilized.

5.4. Transgenic Animal Models

Transgenic animals may be engineered, using techniques well known to those of skill in the art, whose cells may contain modified and/or additional MIF and or MIF receptor genes within their genomes. For example, animals may be produced that contain inactive MIF and/or MIF receptor genes, or alternatively, may contain additional MIF and/or MIF receptor genes.

Such transgenic animals may be used as model systems for the evaluation of cytokine responses in vivo, and may additionally serve as a means by which new drugs for the treatment of conditions involving cytokine-mediated toxicity are identified and tested.

5.4.1. MIF and/or MIF Receptor Transgenes

DNA containing the nucleotide coding sequence for all or any portion of the MIF gene may be used to produce transgenic animals. Alternatively, all or any portion of a gene encoding a MIF receptor may be used. Further, insertions, substitutions, and/or deletions of one or more nucleotides of the MIF and/or MIF receptor genes may also be utilized in the construction of the transgenic animals. Due to the degeneracy of the genetic code, other DNA sequences which encode substantially the same MIF or MIF receptor protein or a functional equivalent can also be used. The nucleotide coding sequence used to produce the transgenic animals of the invention may be regulated by any known promoter regulatory nucleotide sequence. If it is required that expression of the transgene be limited to one or more specific tissues, tissue-specific enhancer regulatory sequences may also be used. Multiple copies of the genes or gene constructs may be stably integrated into the transgenic founder animals.

Any of the nucleotide coding sequences and/or regulatory sequences that will yield any of the variants described here can be produced using recombinant DNA and cloning methods which are well known to those of skill in the art. In order to produce the gene constructs used in the invention, recombinant DNA and cloning methods which are well known to those skilled in the art may be utilized (see Sambrook et al., 1989, Molecular Cloning, A Laboratory Manual, 2nd Ed., Cold Spring Harbor Laboratory Press, New York). In this regard, appropriate MIF and/or MIF receptor coding sequences may be generated from MIF cDNA or genomic clones using restriction enzyme sites that are conveniently located at the relevant positions within the sequences. Alternatively, or in conjunction with the method above, site directed mutagenesis techniques involving, for example, either the use of vectors such as M13 or phagemids, which are capable of producing single stranded circular DNA molecules, in conjunction with synthetic oligonucleotides and specific strains of *Escherichia coli* (*E. coli*) (Kunkel, T. A. et al., 1987, Meth. Enzymol. 154:367–382) or the use of synthetic oligonucleotides and PCR (polymerase chain reaction) (Ho et al., 1989, Gene 77:51–59; Kamman, M. et al., 1989, Nucl. Acids Res. 17: 5404) may be utilized to generate the necessary nucleotide coding sequences. Appropriate MIF and/or MIF receptor sequences may then be isolated, cloned, and used directly to produce transgenic animals. The sequences may also be used to engineer the chimeric gene constructs that utilize regulatory sequences other than the MIF and/or MIF receptor promoter, again using the techniques described here. These chimeric gene constructs would then also be used in the production of transgenic animals.

Transgenic animals may also be produced in which the function of the endogenous MIF and/or MIF receptor genes has been disrupted. To accomplish these endogenous gene disruptions, the technique of site-directed inactivation via gene targeting (Thomas, K. R. and Capecchi, M. R., 1987, Cell 51:503–512) may be used. Briefly, vectors containing some nucleotide sequences homologous to the endogenous gene of interest are designed for the purpose of integrating, via homologous recombination with chromosomal sequences, into and disrupting the function of, the nucleotide sequence of said endogenous gene.

5.4.2. Production of Transgenic Animals

Animals of any species, including but not limited to mice, rats, rabbits, guinea pigs, pigs, mini-pigs, and non-human primates, e.g., baboons, squirrel monkeys and chimpanzees may be used to generate the transgenic animals of the invention. Any technique known in the art may be used to introduce the transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. (For a review of such techniques, see Gordon, 1989, Transgenic Animals, Intl. Rev. Cytol. 115:171–229, which is incorporated by reference herein in its entirety.)

Once the founder animals are produced, they may be bred, inbred, outbred, or crossbred to produce colonies of the particular genotype desired. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems.

5.5. Diagnostic Applications

MIF protein and/or mRNA levels may be monitored in an individual, using standard techniques, as an indication of the deleterious aspects of a disease condition. For the measurement of MIF protein concentrations, such monitoring techniques include, but are not limited to immunological assays such as, for example, Western blots, immunoassays such as radioimmuno-precipitation, enzyme-linked immunoassays, and the like. For the measurement of MIF mRNA concentrations, such techniques may include, for example, hybridization techniques such as Northern blot analysis, or any RNA amplification techniques, which may involve, for example, polymerase chain reaction (the experimental embodiment set forth in Mullis, K. B., 1987, U.S. Pat. No. 4,683,202) ligase chain reaction (Barany, F., 1991, Proc. Natl. Acad. Sci. USA 88: 189–193) self-sustained sequence replication (Guatelli, J. C. et al., 1990, Proc. Natl. Acad. Sci. USA 87: 1874–1878), transcriptional amplification system (Kwoh, D. Y. et al., 1989, Proc. Natl. Acad. Sci. USA 86: 173–1177), or Q-Beta Replicase (Lizardi, P. M. et al., 1988, Bio/Technology 6: 1197).

6. EXAMPLE

Molecular Cloning of MIF and Structural Comparison Between Murine and Human MIF 6.1. Materials and Methods 6.1.1. Materials Reagents for polymerase chain reaction (PCR), reverse transcription (RT), and other molecular biology techniques were purchased from Gibco BRL (Grand Island, N.Y.) unless stated otherwise. PCR buffer was from Perkin Elmer Cetus (Norwalk, Conn.); RNAse inhibitor "rRNasin" was obtained from Promega (Madison, Wis.); RNAzol™B was from TEL-TEST, INC. (Friendswood, Tex.); and oligonucleotides were purchased from OLIGOS ETC., INC. (Wilsonville, Oreg.). Manual DNA sequencing was performed with the SEQUENASE$^R$ 2.0 system (United States Biochemical, Cleveland, Ohio, Tabor & Richardson, 1987). For automated DNA sequencing, the Taq DyeDeoxy™ Terminator Cycle Sequencing Kit (Applied Biosystems Inc., Foster City, Calif.) was utilized. Western blotting was performed following a modification of the method by Anderson et al. (1982, Electrophoresis 3:135). Sodium dodecylsulfate-polyacrylamide gel electrophoresis (SDS-PAGE) and Western blotting reagents were from Pierce (Rockford, Ill.). Polyclonal anti-rmuMIF antiserum was prepared from rabbits immunized with purified rmuMIF. Thioglycollate broth (Difco, Detroit, Mich.) was prepared according to the manufacturer's recommendation, autoclaved, and stored protected from light at room temperature. E. coli O111:B4 LPS and polymyxin B were purchased from Sigma (St. Louis, Mo.). LPS was resuspended in pyrogen-free water, vortexed, sonicated, aliquoted (5 mg/ml), and stored at −20° C. Serial dilutions of LPS were prepared in pyrogen-free water and sonicated (Branson 3210, Danbury, Conn.) for 10 min prior to use.

6.1.2. Molecular Cloning of Murine and Human MIF

Murine MIF was cloned from the mouse anterior pituitary cell line AtT-20/D16v-F2 (American Type Culture Collection, Rockville, Md.). Cells were plated at 1×10$^6$ cells/ml in DMEM containing 50 μg/ml gentamicin (Gibco BRL), and 10% heat-inactivated fetal bovine serum (FBS) (HyClone, Logan, Utah). After 3 h of incubation at 37° C. in a humidified atmosphere with 5% $CO_2$, non-adherent cells were removed and the remaining adherent cells washed twice with DMEM/10% FBS. LPS (50 μg/ml) then was added and the cells were incubated for 16 h. At the end of this time, cell culture medium was removed and total RNA was isolated with RNAzol™B according to the manufacturer's instructions. One μg of RNA was reverse transcribed using oligo (dT)$_{12-18}$ and M-MLV reverse transcriptase in a 50 μL reaction. Five μL of cDNA was amplified by PCR (32 cycles; 1 min at 94° C., 1 min at 55° C., 1 min at 72° C.) using MIF primers. A single DNA amplification product of expected size was obtained and purified using the GENE CLEAN II$^R$ Kit (BIO 101 Inc., La Jolla, Calif.). The cDNA then was cloned into the plasmid pT7Blue and transformed into Nova Blue competent *E. coli* using the pT7Blue T-Vector Kit (Novagen, Madison, Wis.). Recombinant DNA was prepared from multiple white colonies using the Plasmid Magic™ Minipreps DNA Purification System (Promega) and sequenced manually in a Sequi-Gen II Sequencing Cell (BIO-RAD, Hercules, Calif.).

For human MIF cloning, Jurkat H33HJ-JA1 cells (American Type Culture Collection) were plated at $1\times10^6$ cells/ml in RPMI containing 50 µg/ml gentamicin and 10% heat-inactivated FBS. After 3 h of incubation at 37° C. in a humidified atmosphere with 5% $CO_2$, non-adherent cells were removed and the remaining adherent cells washed twice with RPMI/10% FBS. Cells were incubated for another hour and the total RNA was isolated and subjected to RT as described above. NdeI/MIF- and BamHI/MIF-fusion primers (5'-CCATATGCCGATGTTCATCGTAAACAC-3' and 3'-CGGATCCTGCGGCTCTTAGGCGAAGG-5') were designed from a huMIF cDNA sequence (Weiser et al., 1989, Proc. Natl. Acad. Sci. USA 86: 7522) and used to amplify human MIF cDNA as described above. A single PCR product of predicted size was obtained, purified using the GENE CLEAN II$^R$ Kit, and ligated into the NdeI/BamHI-digested pET11b vector (Novagen). *E. coli* DH5α was transformed with the ligation mixture and the single recombinant colonies isolated after overnight growth. Plasmid DNA was prepared from eight clones and the MIF insert sequenced bi-directionally by automated methods using an ABI Model 373A DNA sequencer (Applied Biosystems Inc.).

6.1.3. Expression and Purification of Recombinant MIF

The recombinant pT7Blue clone containing muMIF cDNA was digested with the restriction enzymes NdeI and BamHI, and the MIF insert isolated and ligated into the NdeI/BamHI-digested pET11b vector (Novagen). *E. coli* DH5α was transformed and the single recombinant colonies isolated and stored in 20% glycerol at −80° C. until use. Murine or human MIF-containing pET11b plasmid DNA then was prepared and used to transform the *E. coli* BL21 (DE3) expression strain (Novagen). One-liter cultures were grown at 37° C. until the optical density at 600 nm reached 0.6–0.8. Isopropyl 1-thio-β-D-galactopyranoside (IPTG) was added to a final concentration of 1 mM and the incubation continued at 37° C. for an additional 3 h. Bacteria then were harvested by centrifugation and the cell pellets frozen at −20° C. until use.

For protein purification, the bacterial pellets (corresponding to 50 ml of culture) were thawed and resuspended in 3.5 ml of Tris-buffered saline (50 mM Tris-HCl, 150 mM NaCl, pH 7.5). The bacteria were lysed by adding an equal volume of washed glass beads (106 microns; Sigma, G-8893) and vortexing the mixture vigorously for 10 min. Lysis was confirmed by examination under phase contrast microscopy. Glass beads were removed by centrifugation at 1000 g for 10 min and the bacterial extract then was centrifuged at 38000 g for 30 min. The supernatant, representing the cleared bacterial lysate, was sterile-filtered through a 0.45 µm and then a 0.22 µm membrane filter and subjected to MONO Q anion exchange chromatography using a Fast Protein Liquid Chromatography system (FPLC) (Pharmacia, Piscataway, N.J.). The Mono Q column was equilibrated with Tris-buffered saline. MIF was eluted with the same buffer in the first flow-through fractions (3 ml), which were pooled and placed on ice immediately. The MIF-containing fractions then were applied to a C8-SepPak reverse-phase (RP) column (Waters, Division of MILLIPORE, Milford, Mass.) that had been washed first with methanol, followed by water. Unbound material was eluted by washing the resin with 10 column volumes of water and 20% acetonitrile/water, respectively. MIF then was eluted with 6 column volumes of 60% acetonitrile/water, frozen at −80° C., lyophilized, and kept at −20° C. until use. For renaturation, MIF was dissolved at a concentration of 200–400 µg/ml in 20 mM sodium phosphate buffer (pH 7.2) containing 8 M urea and 5 mM DTT, and dialyzed against 20 mM sodium phosphate buffer (pH 7.2) containing 5 mM DTT, followed by 20 mM sodium phosphate buffer (pH 7.2) alone. Renatured MIF was sterile-filtered and kept at 4° C. until use. The LPS content of MIF preparations was determined by the chromogenic Limulus amoebocyte assay (Bio-Whittaker Inc., Walkersville, Md.). Attempts to purify rmuMIF from the cleared bacterial lysate by affinity chromatography with S-hexyl-glutathione-agarose beads (Sigma, H-7011) were performed following the method for single-step purification of protein/glutathione-S-transferase fusion constructs (Smith & Johnson, 1988, Gene 67: 31).

6.1.4. Purification of Native MIF

Two grams of mouse liver acetone powder (Sigma, L-8254) were resuspended in 20 ml of Tris-buffered saline, vortexed, and the insoluble material removed by centrifugation at 1000 g for 10 min. The supernatant, containing MIF and other hepatic proteins, was filtered (0.45 µm followed by 0.22 µm filter) and subjected to MONO Q/FPLC anion exchange chromatography as described above. MIF eluted with the first flow-through fractions (3 ml), which were pooled and applied to a Pro S cation exchange column (BIO-RAD) that was equilibrated with Tris-buffered saline. MIF eluted with Tris-buffered saline and the MIF-containing fractions again were recovered from the flow-through. The MIF fractions then were pooled and applied to a C8-SepPak cartridge. MIF was eluted with 60% acetonitrile/water, lyophilized, and stored as described above. Attempts to purify liver MIF from mouse liver supernatant by affinity chromatography with S-hexyl-glutathione-agarose beads were performed as described above.

6.1.5. Biochemical Characterization of MIF

SDS-polyacrylamide gel electrophoresis (SDS-PAGE) was performed in 18% gels under reducing conditions (Laemmli, 1970, Nature 227: 680). The gels were either stained with silver or processed further for Western blotting. For silver staining, gels first were fixed for 16 h in 50% methanol/10% acetic acid and then analyzed as described (Poehling & Neuhoff, 1981, Electrophoresis 2: 141). For Western blotting, proteins were transferred to nitrocellulose membrane (Schleicher & Schuell, Keene, N.H.) by electroblotting at 50 V and 150 mA for 16 h using CAPS-transfer buffer (10 mM CAPS, 20% methanol, pH 11.0). Membranes then were incubated with blocking buffer (50 mM Tris-HCl, 500 mM NaCl, pH 7.5, 5% non-fat dry milk, 0.05% Tween-20) followed by incubation with a 1:1000 dilution of polyclonal rabbit anti-rmuMIF antiserum in binding buffer (50 mM Tris-HCl, 500 mM NaCl, pH 7.5, 1% BSA, 0.05% Tween-20). After extensive washing in binding buffer, membranes were incubated with a 1:1000 dilution of horseradish peroxidase-conjugated goat anti-rabbit antibody (Pierce) in binding buffer, washed twice with binding buffer, twice with 50 mM Tris-Base (pH 7.5) containing 150 mM NaCl, and developed with chloronaphthol/$H_2O_2$ substrate. Pre-stained protein molecular weight ($M_r$) markers ranged from 2.5–43 kDa (Gibco BRL).

N-terminal MIF sequence was determined by Edman degradation (Allen, 1981 In: Sequencing of Proteins and Peptides, Elsevier, Amsterdam, N.Y.) and automated gas-phase sequencing following a manufacturer's protocol (Applied Biosystems).

For N-glycosylation analysis, 0.1 μg of purified liver-derived MIF was incubated with the endoglycosidase PNGase F according to the manufacturer's instructions (New England BioLabs, Beverly, Mass.). Samples then were mixed 1:1 with Laemmli electrophoresis buffer, boiled for 5 min, and ¼ of the incubation mixture analyzed by SDS-PAGE/Western blotting as described above. To control for digestion efficiency, IgG light and heavy chains were digested in parallel and resolved on the same gel. Digestion was assessed to be complete after 3 h incubation with 5000 units/ml of PNGase F.

For analytical size exclusion chromatography, 40 μg of purified rmuMIF or rhuMIF was dissolved in 200 μl 20 mM sodium phosphate buffer (pH 7.2) containing 7 M GdnHCl. The sample was separated over a Superose 12 HR 10/30 column (Pharmacia), equilibrated with the same buffer, and eluted at a flow rate of 0.5 ml/min. Size markers were from BIO-RAD (1.35–670 kDa) and were chromatographed under the same conditions.

Mass spectrometric analysis (MS) of MIF was performed by matrix-assisted laser desorption ionization MS as described elsewhere (Hillenkamp & Karas, 1990, Meth. Enzymol. 193: 280) using a Shimadzu Kratos Kompact MALDI 3 V3.0.2 machine (Hannover, Germany). Twenty individual spectra were accumulated for each mass analysis. In addition, rmuMIF was analyzed by ion-spray mass spectroscopy (IS-MS) using an API III triple quadrupole mass spectrometer with an IonSpray™ interface (Sciex, Toronto).

Purified, renatured rmuMIF (20 μg/ml) and MIF-containing bacterial lysates (estimated MIF content: 50 μg/ml) were analyzed photometrically for glutathione-S-transferase (GST) activity by the method of Fjellstedt et al. (1973, J. Biol. Chem. 248: 3702) using 1,2-epoxy-3-(p-nitrophenoxy)propane (EPNP) as a substrate and bovine GST (Sigma, G-8386) as a positive control (Blocki et al., 1992, Nature 360: 269). In this assay system, bovine GST (400 μg/ml) was found to have an enzyme activity of 0.014 units/ml with respect to the substrate EPNP.

6.1.6. Bioactivity Profile

The macrophage/monocyte migration inhibitory activity of recombinant MIF was analyzed by studying the migration of human peripheral blood monocytes in modified Boyden chambers (Boyden, 1962, J. Exp. Med. 115: 453). Monocytes were isolated from heparinized venous blood of healthy donors and resuspended at a concentration of 2.5× $10^6$ cells/ml in Gey's balanced salts solution (Gibco BRL) containing 2% fatty acid-free bovine serum albumin (Sigma) and 20 mM Hepes (pH 7.2). MIF-containing (0.0001–10 μg/ml) solutions or buffer controls were placed in the lower compartment of the Boyden chamber, covered tightly by a polyvinylpyrrolidone-free polycarbonate filter (5-μm pore size, no. 155845, Costar Corp., Cambridge, Mass.) and monocytes ($1\times10^5$) added to the compartment above the filter. The chambers then were incubated for 3 h at 37° C. in a humidified atmosphere with 5% $CO_2$. At the end of this time, the filters were recovered and the cells fixed and stained with Giemsa reagent. Monocytes then were counted as described previously (Sherry et al., 1992, Proc. Natl. Acad. Sci. USA 89: 3511).

TNFα production was quantitated in MIF-conditioned RAW 264.7 macrophage supernatants by L929 cell cytotoxicity as described previously (Wolpe et al., 1988, J. Exp. Med. 167: 570). RAW 264.7 macrophages were resuspended in RPMI/10% FBS, plated at $1\times10^6$ cells/ml, incubated for 3 hours at 37° C. in a humidified atmosphere with 5% $CO_2$, and washed twice with RPMI/1% FBS. Cells were incubated for 12–14 hours with various doses of MIF diluted in RPMI/1% FBS. At the end of each experiment, cell culture media were collected, centrifuged (10 min at 800 g), and supplemented with 1 mM PMSF. MIF-induced TNFα activity was measured immediately afterwards. Polyclonal rabbit anti-recombinant murine TNFα antiserum (50 μl/ml) blocked TNFα activity completely, and MIF did not contribute to TNFα activity as recombinant murine TNFα (rTNFα) (5 pg/ml to 1 μg/ml) cytotoxicity remained unchanged when rmuMIF (10 pg/ml to 10 μg/ml) or anti-rmuMIF antibody were added to L929 cells together with rTNFα.

Nitric oxide (NO) production was quantitated in MIF-conditioned RAW 264.7 and thioglycollate-elicited peritoneal exudate macrophage supernatants by measuring nitrite and nitrate content with the Griess reagent. RAW 264.7 macrophages were prepared and conditioned as described above. In some experiments, cells were incubated for 1 h with recombinant murine interferon-γ (IFN-γ) (100 IU/ml) (Boehringer-Mannheim, Indianapolis, Ind.) prior to the addition of MIF. Thioglycollate-elicited peritoneal exudate macrophages were obtained from BALB/c mice that were injected intra-peritoneally 3–4 days previously with 2 ml of sterile thioglycollate broth. Cells were harvested under strict aseptic conditions by lavage of the peritoneal cavity with 5 ml of an ice-chilled 11.6% sucrose solution. After centrifugation (10 min at 800 g), cells were resuspended in RPMI/10% FBS and plated at a density of $2\times10^6$ cells/ml. After 3 h of incubation, non-adherent cells (i.e. PMNs, lymphocytes) were removed with RPMI/1% FBS and the remaining adherent cells conditioned with MIF as described for RAW 264.7 cells. Trace concentrations of contaminating LPS were neutralized by incubating MIF (1 and 10 μg/ml in cell culture media) with polymyxin B at a concentration of 10 and 100 ng/ml, respectively, for 30 min at room temperature under sterile conditions. The mixture was cleared by centrifugation and added to the prepared macrophage cultures. The polymyxin B concentration added was approximately a 1000-fold higher than necessary to neutralize the contaminating LPS present. For antibody neutralization of MIF activity, rmuMIF (1 and 10 μg/ml in cell culture media) was treated with 20 μL/ml of anti-rmuMIF or normal rabbit control serum and added to the macrophages as described above.

6.1.7. Conformational and Structural Stability Analysis

CD spectra were recorded on an Aviv Associates Model 62DS spectropolarimeter. The spectra represent the average of three scans recorded at 25° C. in the range between 190 nm and 250 nm and were collected at 0.25 nm intervals, with a band width of 1.5 nm and a time constant of 1.0 sec. The quartz cells (1 and 10 mm) used in all CD measurements were washed with 30% HCl in ethanol, rinsed with water and methanol, and dried before used. Protein concentrations were determined from stock solutions prepared in 20 mM phosphate buffer (pH 7.2) using the Bio-Rad protein assay (BIO-RAD). This assay was found to agree with values obtained by quantitative amino acid analysis. Thirty min before CD analysis, proteins were diluted from the stock solutions to a final concentration of 10 μM in 20 mM phosphate buffer (pH 7.2), unless stated otherwise. CD spectra are presented as a plot of the mean molar ellipticity per residue ($[\theta]$, deg $cm^2$ $dmol^{-1}$) versus the wavelength.

For unfolding experiments, MIF stock solutions dissolved in 20 mM phosphate buffer (pH 7.2) were mixed with increasing volumes of 8 M GdnHCl (molecular biology reagent grade, Sigma) prepared in 20 mM phosphate buffer (pH 7.2) so as to achieve a final protein concentration of 10 μM and the indicated final GdnHCl concentrations. Samples then were equilibrated at room temperature for 30 min prior to the recording of CD spectra.

6.2. Results
6.2.1. Cloning of Murine and Human MIF

N-terminal protein sequencing and cDNA cloning were used to identify the murine homolog of MIF among the proteins secreted by LPS-stimulated anterior pituitary cells. MuMIF cDNA was prepared from the total RNA of LPS-stimulated anterior pituitary cells (AtT-20) and amplified with MIF primers. MIF cDNA then was cloned into the pT7Blue T-vector and subjected to DNA sequence analysis. The muMIF cDNA sequence obtained from 6 plasmid clones was compared to a previously published human T-cell MIF cDNA (Weiser et al., 1989, Proc. Natl. Acad. Sci. USA 86: 7522). Murine MIF cDNA (FIG. 3) was found to display a 88.2% sequence homology to this huMIF sequence over a 348 nucleotide open reading frame and to be identical in sequence with recently reported murine 3T3 fibroblast, and murine embryonic eye lens MIF cDNAs (Lanahan et al., 1992, Mol. Cell. Biol. 12: 3919; Wistow et al., 1993, Proc. Natl. Acad. Sci. USA 90: 1272).

HuMIF cDNA was prepared by RT/PCR of RNA isolated from resting Jurkat H33HJ-JA1 T-cells. MIF cDNA was amplified with flanking primers bearing NdeI/BamHI restriction sites, thus enabling the subsequent cloning of the huMIF amplification product directly into a NdeI/BamHI-digested pET11b prokaryotic expression plasmid. Human MIF cDNA sequence then was obtained by sequencing both DNA strands of 8 independently derived E. coli clones. This Jurkat T-cell MIF sequence was found to be identical to a recently reported human fetal lens MIF cDNA (Wistow et al., 1993, Proc. Natl. Acad. Sci. USA 90: 1272) and a glycosylation inhibition factor (GIF) cDNA (Mikayama et al., 1993, Proc. Natl. Acad. Sci. USA 90: 10056), but differed from the first reported human T-cell MIF sequence obtained from the T-CEMB cell line (Weiser et al., 1989, Proc. Natl. Acad. Sci. USA 86: 7522) by a single base change at position 318. This G→A substitution produces a conservative $Ser^{106}$→$Asn^{106}$ change in the deduced amino acid sequence and renders the human protein even more homologous with murine MIF. Murine pituitary MIF cDNA and human Jurkat cell cDNA exhibited 88.5% identity over a 348 nucleotide open reading frame and the a mino acid sequences deduced for murine (AtT-20) and human (Jurkat) MIF were found to be 90% identical over the 115 amino acids (FIG. 4). No apparent N-terminal signal sequences were evident in either the murine or the human proteins. MIF thus joins a growing list of cytokines, such as interleukin-1 (IL-1) (Rubartelli et al., 1990, EMBO J. 9:1503), basic fibroblast growth factor (bFGF) (Jackson et al., 1992, Proc. Natl. Acad. Sci. USA 89: 10691), and a secreted form of cyclophilin (Sherry et al., 1992, Proc. Natl. Acad. Sci. USA 89: 3511), which are released from cells by non-classical protein secretion pathways. Two potential N-glycosylation sites were found a t positions 75 and 110 of the muMIF amino acid sequence and were at nearly identical positions in the human Jurkat MIF sequence (positions 73 and 110). Three cysteine residues (positions 57, 60, and 81) also were at identical places in the murine and human MIF predicted amino acid sequences.

6.2.2. Expression and Purification of Recombinant MIF from E. coli

Recombinant muMIF and huMIF were expressed in E. coli by cloning murine and human MIF cDNA into the IPTG-inducible pET expression plasmid system. Initial attempts to express murine MIF from the pET15b vector, which created an N-terminal oligo-histidine fusion protein and allowed for facile purification of recombinant protein by ion metal affinity chromatography (IMAC), were unsuccessful because the protein was resistant to the subsequent thrombin cleavage necessary to remove the oligo-histidine leader. Thus, recombinant muMIF was expressed and then purified by conventional means and the muMIF cDNA subcloned into the plasmid pET11b. This produced a construct which bore a three amino acid (Met-Asp-Ser) leader sequence attached to the N-terminus of MIF. HuMIF also was expressed from the pET11b vector but was engineered by DNA amplification to begin at the second amino acid of the open reading frame, with the start methionine of MIF provided by the NdeI restriction site. The correct expression of MIF was verified by N-terminal amino acid sequencing of gel-purified protein (10 amino acids for muMIF), SDS-PAGE, and Western blotting with anti-AtT-20 MIF antibody. The pET11b-derived MIF was used for the subsequent purification of bioactive muMIF and huMIF.

Recombinant murine or human MIF were found to constitute 40% of the total supernatant protein of E. coli lysates. Anion exchange chromatography at pH 7.5 resulted in approximately an 80% purification of murine and human MIF. Subsequent application to a C8 reverse-phase column yielded pure protein for both the murine and the human recombinant proteins, as verified by the appearance of single bands of predicted $M_r$ (12.5 kDa) by SDS-PAGE/silver staining and by mass spectrometric analysis, infra. This simple and rapid two-step procedure was used to purify 1 mg of murine or human MIF per 50 ml of E. coli culture. After renaturation, 0.8–0.9 mg of soluble, bioactive recombinant MIF was obtained per 50 ml culture. The overall yield of MIF protein from total bacterial supernatant protein was estimated to be 20%. This two-step purification method was elected for reasons of simplicity and rapidity and to minimize protein losses by non-specific precipitation. Purification by C8 chromatography using a disposable, low volume push column also served to remove the LPS carried over from E. coli host cells. Recombinant MIF purified by these procedures contained no more than trace amounts of LPS (4–8 ng LPS per mg MIF).

6.2.3. Purifiaction of Native MIF

To assess more precisely the biological activities of recombinant MIF, native MIF was also purified from mouse tissue. Pituitary cells yielded insufficient quantities of MIF protein for biochemical characterization, but Western blotting showed that the liver was an abundant source of MIF in vivo. MIF was purified from liver by a method similar to that used for recombinant MIF purification. Mono Q anion exchange chromatography resulted in partial purification and increased the relative MIF content by approximately 25-fold. Subsequent application to the C8 push column afforded almost pure MIF. Upon SDS-PAGE/silver staining analysis however, 5 additional bands were detected that could not be removed by varying the elution conditions of the RP chromatography. A Pro S cation exchange chromatography step therefore was added prior to the C8 step to remove these contaminants. The purity and homogeneity of liver MIF was established by SDS-PAGE/silver staining, Western blotting using anti-rmuMIF antibody, and mass spectrometric analysis. Laser desorption MS demonstrated a single protein species of $M_r$ 12,555. The MIF content of mouse liver acetone powder was estimated to be less than 0.1% of total protein and 2 grams of mouse liver powder were used to purify to homogeneity 50 μg native liver MIF.

6.2.4. Biochemical Characterization of MIF

The $M_r$ for liver murine MIF, rmuMIF, and rhuMIF were each between 12000 and 13000 as estimated by reducing SDS-PAGE. Two potential N-linked glycosylation sites were detected in the predicted amino acid sequence of murine and human MIF and thus the possibility that native muMIF was post-translationally glycosylated in vivo was investigated. Endoglycosidase F (PNGase F) digestion of purified liver MIF followed by reducing SDS-PAGE/Western blotting analysis showed no shift in the observed $M_r$, indicating the absence of significant N-glycosylation of native liver MIF.

Gel exclusion chromatography of GdnHCl-denatured recombinant MIF showed a $M_r$ of 14,256 and 13,803 for the murine and human proteins, respectively, indicating that MIF eluted predominantly as a monomer.

Laser desorption MS of MIF was performed to further assess glycosylation as well as the presence of any other significant post-translational modifications of MIF. Native MIF obtained from mouse liver was determined to have a $M_r$ of 12,555 (predicted MH$^+$ average mass of oxidized muMIF=12,503). By comparison, rmuMIF (which bore a 3 amino acid N-terminal leader sequence) was found to have a $M_r$ of 12,814 (predicted MH$^+$ average mass of oxidized rmuMIF 12,801). Ion-spray MS of rmuMIF yielded a similar mass ($M_r$=12,804). Using laser desorption MS, rhuMIF was found to have a $M_r$ of 12,521 (predicted MH$^+$ average mass of oxidized rhuMIF=12,475). Differences observed between the experimental and theoretical, predicted masses were within the margin of experimental error (0.1–1%) for these analyses. These data essentially ruled out the presence of significant post-translational modifications of either native or recombinant MIF protein.

A 12 kDa protein purified from rat liver bearing N-terminal homology with huMIF has been reported to bind to glutathione affinity matrix and to exhibit glutathione-S-transferase (GST) activity (Blocki et al., 1992, Nature 360: 269). Neither liver MIF nor rmuMIF was shown to specifically absorb to glutathione-modified matrix.

6.2.5. Bioactivity Profile

Purified rmuMIF displayed significant migration inhibitory activity when tested on human peripheral blood monocytes (FIG. 5). A bell-shaped dose response curve was observed with peak activity occurring at 0.1 μg/ml. The precise basis for diminished inhibitory activity at high MIF concentrations is not known, but similar dose-response profiles have been observed for chemotactic cytokines (Sherry et al., 1992, Proc. Natl. Acad. Sci. USA 89: 3511).

Recombinant MIF was used to induce TNFα release by the murine RAW 264.7 macrophage cell line. Both rmuMIF and rhuMIF added at concentrations of 0.1–10 μg/ml caused the release of bioactive TNFα in the ng/ml range (Table II). Despite species-specific differences, rhuMIF at 1/μg/ml was found to be slightly more active than rmuMIF on murine macrophages. At the same concentration (1 μg/ml), the TNFα-inducing activity of MIF obtained from mouse liver was found to be higher than the activity of rmuMIF. When tested at a concentration of 0.1 μg/ml however, the TNFα-inducing activity of mouse liver MIF was identical to rmuMIF. Similar findings were obtained when thioglycollate-elicited mouse peritoneal macrophages were used to study MIF-induced TNFα release. Overall, the activity of purified native MIF was within the range observed for the recombinant proteins.

TABLE II

MIF-INDUCED SECRETION OF TNFα BY MOUSE MACROPHAGES[a]

| MIF (μg/ml) | Secretion of TNFα (ng/ml) induced by: | | |
|---|---|---|---|
| | rmuMIF | rhuMIF | Native MIF |
| 10 | ND | 3.9 ± 2.8 | ND |
| 1 | 1.2 ± 0.1 | 3.4 ± 2.8 | 6.9 ± 3.4 |
| 0.1 | 0.2 ± 0.3 | 2.9 ± 2.4 | 0.2 ± 0.1 |
| 0.01 | 0 | ND | 0 |

[a]RAW 264.7 macrophages were prepared and incubated with MIF for 12–14 h as described in Section 6.1.6. supra. After the incubations, macrophage culture supernatants were removed, and analyzed by L929 cell toxicity assay for TNFα activity. TNFα measurements were performed in duplicate and TNFα activity is expressed as the difference between the level produced by MIF- stimulated cells and by non-stimulated control cells. Data arethe mean ± SEM of at least three separate experiments. ND: not determined.

Native and recombinant MIF also induced NO production in macrophages (Table III). However, significant MIF-induced NO production was observed only when macrophages were incubated with IFN-γ prior to stimulation with MIF. In RAW 264.7 macrophages, the activity of rhuMIF at 1 μg/ml was found to be approximately 4-fold higher than rmuMIF. Native MIF obtained from mouse liver also was more active in this assay than rmuMIF. MuMIF stimulated NO production from IFN-γ-primed, thioglycollate-elicited peritoneal exudate macrophages at levels which were comparable with those observed in RAW 264.7 cells. However, liver MIF at 1 μg/ml was not found to be more active than rmuMIF on this macrophage cell type.

The synthesis of NO by macrophages is induced by ≧10 ng/ml of LPS and this effect is potentiated by IFN-γ priming (Ding et al., 1988, J. Immunol. 141: 2407). To exclude the possibility that the trace amounts of LPS present in recombinant MIF preparations contribute to NO production, MIF-induced NO release was tested after neutralization of LPS with a large excess of polymyxin B. The production of NO was not reduced by polymyxin B treatment, arguing against a potentiating role for LPS in the stimulation of macrophages by MIF. In further control studies, the addition of neutralizing anti-rmuMIF antiserum (20 μl/ml) inhibited rmuMIF (1 and 10 μg/ml)-induced NO production, further confirming the specificity of macrophage stimulation by recombinant MIF.

TABLE III

NO PRODUCTION IN MOUSE MACROPHAGES INDUCED BY MIF, ALONE OR IN COMBINATION WITH IFN-γ[a]

| | MIF (μg/ml) | Formation of nitrite (μM) induced by: | | |
|---|---|---|---|---|
| | | rmu MIF | rhuMIF | Native MIF |
| − IFN-γ | 10[a] | 0.2 ± 0.2 | 3.7 ± 2.1 | ND |
| | 1[a] | 0.5 ± 0.5 | 1.5 ± 1.0 | 0 |
| | 0.1[a] | 0.3 ± 0.3 | 0 | 0 |
| | 0.01[a] | 0 | ND | 0 |

TABLE III-continued

NO PRODUCTION IN MOUSE MACROPHAGES INDUCED
BY MIF, ALONE OR IN COMBINATION WITH IFN-γ[a]

| | MIF (μg/ml) | Formation of nitrite (μM) induced by: | | |
|---|---|---|---|---|
| | | rmu MIF | rhuMIF | Native MIF |
| + IFN-γ | 10[a] | 12.3 ± 2.5 | 25.3 ± 7.5 | ND |
| | 1[a] | 5.7 ± 1.3 | 20.4 ± 5.7 | 9.8 ± 1.3 |
| | 0.1[a] | 1.7 ± 0.7 | 8.4 ± 2.6 | 3.1 ± 1.0 |
| | 0.01[a] | 1.9 ± 1.2 | ND | 0.5 ± 0.2 |
| | 1[b] | 12.5 | ND | 3.5 |

[a]RAW 264.7 macrophages were prepared and incubated with MIF for 12–14 h. At the end of incubation, 300 μL of culture supernatant was removed, mixed with 600 μL of Griess reagent, and the concentration of nitrite measured. Nitrite measurements were performed in duplicate and nitrite production is expressed as the difference between the level produced by MIF-stimulated cells versus non-stimulated, or IFN-γ-treated control cells. Data arethe mean ± SEM of at least three separate experiments. ND: not determined.
[b]NO production by MIF-stimulated thioglycollate-elicited peritoneal macrophages in place of RAW 264.7 macrophages. Data are the mean of two separate experiments.

6.2.6. Conformational and Structural Stability Analyses

Far-UV CD has been used widely to analyze the solution conformation of proteins and to verify native and renatured protein structures (Greenfield & Fasman, 1969, Biochemistry 8: 4108). Far-UV CD spectroscopy and GdnHCl-induced unfolding studies were performed with recombinant MIF to begin to assess the secondary structure and the structural stability of this protein in a solution environment. No concentration dependent changes in the CD spectra of MIF were observed within the range studied (1.6–32 μM MIF). The spectrum for rmuMIF showed a pronounced positive ellipticity at 192 nm, a broad negative ellipticity between 209 nm and 222 nm, and small distinct minima at 210 nm and 222 nm. These data are consistent with a highly ordered secondary structure containing predominantly β-sheet, but also α-helix conformation. The spectrum for rhuMIF showed a prominent positive ellipticity at 197 nm and a strong negative ellipticity between 211 nm and 225 nm was observed. This CD spectrum also was consistent with a highly ordered secondary structure, but was suggestive of a higher β-sheet content and a lower α-helix content than rmuMIF. Secondary structure compositions for both proteins then were estimated from computational fits of the CD spectra over the 190–250 nm range using the method of Brahms & Brahms (1980, J. Mol. Biol. 138: 149), which is frequently employed for the analysis of β-sheet-rich proteins. Recombinant muMIF was estimated to contain 42.2% β-sheet, 15.3% α-helix, 7.2% β-turn, and a remainder of 35.3% in random coil. Recombinant huMIF contained a somewhat greater extent of ordered structure, with 72.9% β-sheet, 0% α-helix, 8.3% β-turn, and 17.3% random coil conformation. Secondary structure calculations following the methods of Chou & Fasman (1978, Adv. Enzymol. 47: 45) and Garnier et al. (1978, J. Mol. Biol. 120: 97) also predicted that both muMIF and huMIF exhibit a highly ordered secondary structure. Chou/Fasman calculations predicted the following secondary structure compositions-rmuMIF: 35.6% β-sheet, 10.6% α-helix, and 21.2% β-turn; rhuMIF: 26.1% β-sheet, 30.4% α-helix, and 17.4% β-turn. Garnier/Osguthorpe/Robson analysis predicted the following structures-rmuMIF: 39% β-sheet, 8.5% α-helix, and 20.3% β-turn; rhuMIF: 24.4% β-sheet, 19.1% α-helix, and 25.2% β-turn. The CD data, together with the secondary structure predictions according to the Chou/Fasman and Garnier/Osguthorpe/Robson calculations, indicate that both recombinant murine and human MIF contain a high fraction of β-sheet conformation (24.4%–72.9%). The spectroscopic data and primary sequence predictions showed a similar a-helical content for rmuMIF (8.5%–15.3%). Although the secondary structures predicted by Chou/Fasman and Garnier/Osguthorpe/Robson calculations suggested that there was a significant α-helical content in huMIF, the CD analysis did not show any detectable α-helical elements in rhuMIF.

Helical conformations induced at the membrane-water interface have been suggested to be important for ligand membrane interactions and to influence the binding of ligands to receptors (Kaiser & Kezdy, 1983, Proc. Natl. Acad. Sci. USA 80:1137; Fry et al., 1992, Biopolymers 32:649; Erne et al., 1985, Biochemistry 24: 4263). 2,2,2-Trifluoro-ethanol (TFE) induces and stabilizes the helical conformation of proteins with a helix-forming propensity and has been used to mimic the influence of membranes on polypeptide conformation (Sönnichsen et al., 1992, Biochemistry 31: 8790). To begin to test whether the α-helical content of either murine or human MIF might be increased in the membranous environment, far-UV CD analysis of rmuMIF and rhuMIF was performed in 50% TFE. TFE significantly increased the α-helical content of rmuMIF, as demonstrated by a larger positive ellipticity at 192 nm and pronounced negative ellipticities at 208 nm and 222 nm. The calculated fraction of α-helix conformation increased from 15.3% to 34.7% in the presence of TFE. Recombinant huMIF, which was found to have no measurable α-helical elements in aqueous solution, showed a significant content of α-helix in the presence of TFE as evident by a shift of the positive ellipticity from 197 nm to 192 nm and distinct negative ellipticities at 208 nm and 222 nm. Computational analysis of the spectroscopic data showed that the percentage of α-helix increased from 0% to 36.3%. These data indicate that both murine and human MIF are likely to adopt significant α-helical conformation in a membranous environment.

Protein structural stability can be quantitated by determining the free energy of unfolding, $\Delta G_{N-U}$, where N is the fraction of protein in the native state and U is the fraction in the unfolded state. One method used frequently to assess protein stability is to measure protein mean molar ellipticity per residue as a function of wavelength and GdnHCl concentration (Pace, 1975, CRC Crit. Rev. Biochem. 3: 1). Unfolding curves expressed as the percentage of unfolded protein relative to native protein (i.e. the change in ellipticity at 222 nm) over the concentration of GdnHCl provide two measures of structural stability: 1) the midpoint of unfolding, $[GdnHCl]_{0.5}$, which can be deduced from the linear part of the unfolding curve and 2) the free energy of unfolding at zero denaturant concentration, $\Delta G°_{N-U}$, which can be extrapolated from the unfolding curve by the linear extrapolation method (LEM) (Santoro & Bolen, 1992, Biochem. 31: 4901). Both measures are based on the premise that unfolding follows a reversible two-state mechanism and that unfolding free energy is linearly dependent on denaturant concentration (Greene & Pace, 1974, J. Biol. Chem. 249: 5388).

The CD spectra of rmuMIF were recorded between the wavelengths 210 nm–250 nm in the presence of increasing concentrations of GdnHCl (0–7 M). Recording below 210 nm was not performed due to strong scattering effects at these wavelengths. The MIF spectrum, defined in the absence of GdnHCl, changed visibly when ≧1.5 M GdnHCl was present, indicating a significant loss of conformational integrity. The featureless spectrum for fully denatured MIF in the presence of 7 M GdnHCl was similar to spectra observed for other fully unfolded proteins (Greenfield & Fasman, 1969, Biochem. 8: 4108). For quantitation of GdnHCl-induced unfolding, the unfolding of MIF α-helical structures was plotted by expressing the relative change in [θ] at 222 nm (percent unfolded) with respect to increasing concentrations of GdnHCl. The midpoint of unfolding was observed to be at 1.8 M GdnHCl. Next, the LEM was applied to extrapolate $\Delta G°_{N-U}$ from a plot of $\Delta G_{N-U}$ versus the concentration of GdnHCl([GdnHCl]). Data points of the linear portion of the curve could be replotted according to the following equation:

$$\Delta G_{N-U} = \Delta G°_{N-U} - m[\text{GdnHCl}]$$

where m is the slope of the curve, and subjected to linear regression analysis. Murine MIF thus was calculated to have a $\Delta G°_{N-U}$ of 11.75 kJ/mol. By comparison, globular proteins generally exhibit $\Delta G°_{N-U}$ values of approximately 50±15 kJ/mol (Pace 1990, Trends Biochem. Sci. 15: 14).

7. EXAMPLE

In Vivo Administration of MIF Increases Endotoxin-Induced Lethality and Anti-MIF Treatment Confers Protection The following experiment was initially carried out to test the efficacy of purified MIF as a protective factor against endotoxin-induced lethality in animals. Surprisingly, the in vivo administration of MIF potentiated LPS lethality in mice and exacerbated the response to endotoxin challenge. Furthermore, mice pretreated with an anti-MIF antiserum were significantly protected against endotoxin-induced lethality. Anti-MIF treatment also protected against TNFα-induced lethality.

7.1. Materials and Methods 7.1.1. Mice

Nine-week-old BALB/c mice (19–21 g of weight) were utilized for this study. A total of 20 animals in each category (i.e., LPS, LPS plus MIF, anti-MIF, preimmune serum and saline-treated) were included in the experiments described below.

7.1.2. In Vivo Treatment With Endotoxin and MIF

Mice were injected i.p. with 15 mg/kg *E. coli* 01111:B4 LPS (lipopolysaccharide) in saline. MIF prepared as described in Section 6, supra, was administered i.p. to mice at 5 mg/kg in saline at 0 and 12 hours after LPS treatment. Both control and treated animal groups were maintained under the standardized conditions of the animal facility colony rooms and monitored for survival.

7.1.3. Anti-MIF Treatment

Anti-MIF antiserum was produced by immunization of rabbits with 100 μg of recombinant murine MIF purified from *E. coli* transfected with the coding sequence in an expression vector. Anti-MIF serum and normal rabbit serum (NRS) showed no cross-reactivity with *E. coli* 0111:84 LPS as assessed by Western blot analysis and LPS-specific ELISA.

Mice were pretreated with anti-MIF antiserum (containing <0.2 ng LPS/ml), preimmune NRS (containing <3 ng LPS/ml), or a saline control 24 hours and 2 hours prior to challenge with LPS (i.p. at 17.5 mg/ml, an amount of *E. coli* 011.B LPS that had been established as an $LD_{75}$ for saline-injected control mice in prior dose-ranging studies). Pretreatments consisted of 200 μl of sera or 200 μl 0.9% (w/v) NaCl as control, administered i.p.

TNFα challenge consisted of 0.7 μg in Tris-buffered saline administered i.p. concurrently with 18 mg D-galactosamine.

7.2. Results

The effects of MIF on endotoxin-induced lethality were tested by comparing the survival curves of animals challenged in the presence and absence of administered exogenous recombinant MIF. Briefly, each animal was injected i.p. with 300 μg LPS. Half of the animals were additionally administered 100 μg MIF i.p. at 0 and 12 hours post-LPS challenge.

The pooled data representing the results of two such experiments are depicted in FIG. 6A in graphic form. These experiments demonstrate that MIF potentiated LPS lethality in the mice tested. First, the LPS/MIF-treated mice showed an accentuated rate of mortality in that a differential effect of MIF administration, relative to that of the LPS-only mice, was seen beginning approximately 20 hours post LPS challenge. Second, the overall survival of animals in the two categories demonstrated the increased cumulative mortality of animals exposed to MIF in addition to LPS, with only 15% of the LPS/MIF mice surviving at 84 hours post-LPS challenge compared to 65% of the LPS-only treated mice surviving to this time point. The overall comparison in a two tailed Fisher's exact test is P=0.003.

The effects of MIF on endotoxin- and TNFα-induced lethality were tested by comparing the survival of animals challenged after pretreatment with anti-MIF antisera to those animals pretreated with preimmune sera and saline controls. Briefly, animals were injected, i.p., with either anti-MIF antisera, preimmune sera, or saline, 24 hours and 2 hours prior to challenge with either LPS or TNFα.

FIG. 6B illustrates the pooled data representing the results of two experiments in which the mice were challenged with LPS. As can be seen, mice pretreated with anti-MIF antisera were significantly protected from LPS-induced lethality, with all mice surviving until the last recorded timepoint, 86 hours post-challenge. In contrast, only 25% of the animals that had been pretreated with the saline control were still alive at 84 hours post-LPS challenge, and only 50% of those pretreated with preimmune sera were alive. A statistical analysis of these results indicated that the chances of these results occurring under the null hypothesis were, for the overall comparison: P<0.00001; anti-MIF vs. saline: P<0.00001; anti-MIF vs. NRS: 0.0004; and NRS vs. saline: 0.19.

Table IV illustrates the pooled data representing the results of three experiments in which the mice were challenged with TNFα and galactosamine. As recorded above in similar experiments with LPS challenge, mice pretreated with anti-MIF antisera were significantly protected from TNFα-induced lethality, with all mice surviving until the last recorded timepoint. In contrast, only 50% of the animals that had been pretreated with the saline control were still alive at 120 hours post-TNFα challenge, and only 60% of those pretreated with preimmune sera were alive. Any marginal benefits afforded by pretreatment with preimmune control sera in these experiments most likely reflects the well-known but small beneficial effect of exogenous gamma globulin treatment.

TABLE IV

| Treatment Group | Days after TNFα and galactosamine challenge | | | | |
| --- | --- | --- | --- | --- | --- |
| | 1 | 2 | 3 | 4 | 5 |
| Saline | 9/10 | 9/10 | 9/10 | 5/10 | 5/10 |
| | 90% | 90% | 90% | 50% | 50% |
| Pre-immune | 10/10 | 10/10 | 10/10 | 6/10 | 6/10 |
| | 100% | 100% | 100% | 60% | 60% |

TABLE IV-continued

| Treatment Group | Days after TNFα and galactosamine challenge | | | | |
|---|---|---|---|---|---|
| | 1 | 2 | 3 | 4 | 5 |
| Anti-MIF | 10/10 100% | 10/10 100% | 10/10 100% | 10/10 100% | 10/10 100% |

Fraction of the treatment groups surviving after TNFα + galactosamine treatment on day 0.

These experiments demonstrate that the immunological neutralization of MIF had the ability to protect against both LPS-induced and TNFα-induced lethality in the mice tested, as evidenced by the sparing by anti-MIF treatment of animals that would otherwise be expected to die. Thus, these results not only prove that exogenously administered MIF has a deleterious effect on the shock process, but also demonstrate that the neutralization of endogenous MIF protects against endotoxin-induced and TNFα-induced lethality due to shock.

8. EXAMPLE

Administration of Exotoxin Induces MIF Secretion and Anti-MIF Treatment Confers Protection

8.1. Materials and Methods
8.1.1. Cell Preparation and MIF Induction

RAW 264.7 murine macrophages were obtained from the American Type Culture Collection (Rockville, Md.). Cells were grown in RPMI 1640 medium (Gibco, Grand Island, N.Y.), 10% heat-inactivated fetal bovine serum (FBS) (HyClone, Logan, Utah), 50 μg/ml of carbenicillin and gentamicin. RAW 264.7 macrophages were washed with fresh medium, harvested by gentle scraping, resuspended in RPMI/10%FBS, and incubated at $3\times10^6$ cells/well in 3.5-cm tissue culture plates (Linbro®, Flow, McLean, Va.). After 3 h of incubation at 37° C. in a humidified atmosphere with 5% $CO_2$, nonadherent cells were removed and wells were washed twice with RPMI/1%FBS. Cells then were incubated for 12–15 h with TSST-1 (at concentrations ranging from 100 ng/ml to 100 attog/ml). At the end of experiment, cell-culture media were collected and centrifuged (10 min at 800 g). Cell-conditioned media were concentrated 10-fold by membrane filtration (10 kD cut-off) (Centricon-10, Amicon, Beverly, N.Y.).

Thioglycollate-elicited peritoneal macrophages were obtained from BALB/c mice that were injected i.p. 3–4 days previously with 2 ml of sterile thioglycollate broth. Cells were harvested under strict aseptic conditions by lavage of the peritoneal cavity with 5 ml of an ice-chilled 11.6% sucrose solution. After centrifugation (10 min at 800 g), cells were resuspended in RPMI/10% FBS, enumerated and plated at a density of $3-4\times10^6$ cells/well. Cells were incubated for 12 to 15 h with TSST-1 (at concentrations ranging from 100 ng/ml to 100 attog/ml).

Murine T-cells (LBRM-33, a T lymphoma cell-line) were obtained from the American Type Culture Collection (Rockville, Md.). Cells were grown in RPMI 1640 medium (Gibco, Grand Island, N.Y.), 10% heat-inactivated fetal bovine serum (FBS) (HyClone, Logan, Utah), 0.05 mM 2-mercaptoethanol and 50 μg/ml of gentamicin. Cells were washed with fresh medium, harvested by gentle scraping, resuspended, and incubated at $1\times10^6$ cells/well in 3.5-cm tissue culture plates (Linbro®, Flow, McLean, Va.). After 3 h of incubation at 37° C. in a humidified atmosphere with 5% $CO_2$, nonadherent cells were removed and wells were washed twice with RPMI/1%FBS. Cells then were incubated for 12–15 h with TSST-1 (at concentrations ranging from 100 ng/ml to 100 attog/ml). At the end of experiment, cell-culture media were collected and centrifuged (10 min at 800 g). Cell-conditioned media were concentrated 10-fold by membrane filtration (10 kD cut-off) (Centricon-10, Amicon, Beverly, N.Y.).

Samples were resolved on 18% SDS polyacrilamide gels and analyzed by Western blotting as described above.

8.1.2. Anti-MIF Treatment

Eight to 10-week-old (19–21 g) female BALB/c were purchased from Charles River (Kingston, N.Y.). Animals were housed in groups of 5 or 10 mice per cage with free access to food and water and were acclimatized for 5 days prior to experimentation. BALB/C mice were injected i.p. with 200 μl of polyclonal rabbit anti-MIF serum or normal rabbit serum (controls) followed 2 hr later by a lethal i.p. injection combining 50 μg of TSST-1 with 20 mg D-galactosamine. Mice were observed for 7 days.

8.2. Results

TSST-1 was found to be an extremely potent inducer of MIF secretion by macrophages (both RAW 264.7 and peritoneal macrophages) and T cells in vitro. Dose-response studies of TSST-1-induced MIF secretion showed two peaks of MIF secretion. The first peak occurred at 10 pg/ml of TSST-1 and the second at 100 attog/ml ($=10^{-4}$ pg/ml). Anti-MIF treatment markedly reduced mortality from 87.5% (controls) to 33% (p=0.05, two-tailed Fisher's exact test) (FIG. 7).

9. EXAMPLE

MIF is a Primary Inflammatory Mediator in Parasitic Infections

9.1. Production of MIF in Malaria Infection

During malaria infection, hemozoin results from the pericyte-specific polymerization of heme molecules liberated by the catabolism of red blood cell hemoglobin by intra-erythrocytic forms of Plasmodium, and this "malaria pigment" accumulates within the reticuloendothelial system of infected individuals. The structure of hemozoin is known, and hemozoin can be chemically synthesized by polymerizing ferric heme in acetic acid, and separated from unreacted heme by sequential extraction in $NaHCo_3$ buffer (pH 9.2) and ethanol. Endotoxin-free synthetic hemozoin, prepared as above, was added to the murine monocyte cell line RAW 264.7. The treated cells secreted a protein of 12.5 kDa which was shown to be MIF by Western blotting and N-terminal sequence analysis. Thus, hemozoin was a potent inducer of MIF in vitro at as little as 1 nmole heme equivalents. Furthermore, co-incubation of hemozoin with IFN-γ at 10–100 U/ml further increased MIF release.

To further assess the role of MIF in malaria infection, blood was drawn from C3H/HeN mice exhibiting a low level of chronic parasitemia with *Plasmodium berghei* (10% parasitized red cells). Five μl serum aliquots were reacted with an anti-MIF antibody and analyzed by Western blotting. This relatively low level of parasitemia was associated with readily detectable levels of circulating serum MIF. Levels of parasitemia in the 10% range were sufficient to maintain persistent MIF production for as long as 28 days.

In addition, 500 nmoles of endotoxin-free synthetic hemozoin was injected i.p. into C3H/HeN mice and blood sampled 24 and 48 hours later. The sera were separated and assayed for MIF by Western blotting and TNFα by L929 cytotoxicity assays. Although circulating TNFα levels were undetectable in this study (<50 pg/ml), MIF was readily detected in sera at 24 and 48 hours. Hence, a low level of parasitemia was associated with circulating MIF in vivo. MIF appeared in sera under circumstances when TNFα was not detectable. Hemozoin alone was found sufficient to induce MIF production in vitro and in vivo. Taken together, these results show that MIF is an important early mediator in the host response to malaria infection. Furthermore, this observation indicates that anti-MIF therapy may be effective in ameliorating the pathological sequelae of parasite-induced cytokine release.

10. EXAMPLE

Anti-MIF Abrogates Antigen-specific Immune Responses

This example demonstrates that anti-MIF antibody can substantially reduce the magnitude of an antigen-specific immune response. This indicates that MIF is a critical component of an immune response, and thus anti-MIF treatment may be useful in substantially reducing an undesired immune reaction such as autoimmunity and allergy.

10.1. Anti-MIF Inhibits Antigen-specific T Cell Proliferation

Ten BALB/c mice were primed in vivo with RNase A emulsified in complete Freund's adjuvant at 1:1 ratio. Each mouse received 20 µg of RNase A in 0.2 ml i.p. After 2–3 weeks, splenic T cells were isolated and their proliferative activity assayed. In a microtiter plate, $4 \times 10^5$ T cells were incubated with $5 \times 10^5$ antigen-presenting cells per well. While the addition of RNase A led to an increased proliferation of the in vivo primed T cells as measured by $^3$H-thymidine incorporation, this proliferation was reduced to control levels when anti-MIF antibody was also added.

10.2. Anti-MIF Inhibits Antigen-specific Inflammatory Response

BALB/c mice were primed in the left rear footpad and in the neck muscle with complete Freund's adjuvant at 0.2 ml per injection. After 10–14 days, the mice were boosted in the right rear footpad with 50 µl of purified protein derivative (of tuburculin; PPD) with or without 50 µl of anti-MIF antibody. When the width of the right rear footpads of the animals were measured with calipers 48 hours later as an indication of delayed-type hypersensitivity reaction, anti-MIF treatment was shown to reduce the swelling in the footpads by greater than 50% as compared to controls. Analysis by light microscopy also revealed histopathological evidence of reduced inflammation in footpads of anti-MIF treated mice.

11. EXAMPLE

Production of Migration Inhibitory Factor by the Pituitary Gland

The following example describes the production of MIF by pituitary cells in vitro and in vivo.

11.1. Materials and Methods
11.1.1. Cells

The murine anterior pituitary cell line AtT-20 was obtained from American Type Culture Collection and maintained in low serum medium.

11.1.2. Induction of MIF

AtT-20 cells were cultured for 24 hours in serum-free medium (enriched serum-free Joklik's medium from Gibco) containing various concentrations of LPS (E. coli LPS 0111:B4 from Sigma) at 0.5 µg/ml–50 µg/ml. Two ml of conditioned media was removed from $1.5 \times 10^5$ cells and concentrated 100-fold by membrane filtration (10K cut off) prior to SDS polyacrylamide gel electrophoresis (18%). Silver staining analysis of the gels revealed a 12.5 kDa protein band. This protein was transferred to polyvinylidene difluoride membrane and its primary N-terminal amino acid sequence was determined by automated gas-phase sequencing (Applied Biosystems).

11.1.3. Western Blot

MIF release from pituitary (AtT-20) cells was analyzed by Western blotting with anti-MIF antibody (FIG. 8). $1.5 \times 10^5$ pituitary cells were cultured serum-free for 18 h with different concentrations of LPS. After transfer, nitrocellulose membranes were incubated with rabbit anti-rMIF serum (1:1000 dilution) and bound antibody visualized with horse-radish peroxidase-conjugated goat anti-rabbit antibody. 100 ng of rMIF was electrophoresed on the same gel for reference. Control supernatants (C) contained 1 µg/ml LPS that was added after removal of cells. Pre-immune serum showed no reactivity.

11.1.4. Immunocytochemistry

Cells were cultured for 16 h in the presence (FIG. 9B) or absence (FIG. 9A) of 25 µg/ml LPS, washed, fixed with formaldehyde, and incubated with anti-rMIF serum (1:1000 dilution) prior to staining with immunoperoxidase-linked goat anti-rabbit antibody. No staining was observed with pre-immune serum or with immune serum that had been pre-incubated with rMIF.

11.1.5. Detection of MIF mRNA

Pituitary mRNA analyses from two representative mice are shown for each time interval (FIG. 10). RT-PCR analysis utilized murine MIF primers (22 cycles), β-actin primers (25 cycles), or CD2 primers (pituitary cDNA: 35 cycles, control spleen cDNA: 25 cycles) as shown. Nine-week old mice were injected intraperitoneally with LPS at a dose of 2.25 mg/kg and sacrificed 0, 6, 16, 24 and 48 h later. Pituitary RNA was prepared by extraction with RNAzol (Biotecx Laboratories, Inc.) from a total of four mice per time interval. After reverse transcription with oligo-dT, DNA amplification products were analyzed by agarose gel electrophoresis. Reverse transcription efficiency was assessed and normalized relative to β-actin mRNA. The murine MIF primers were: 5'-CCATGCCTATGTTCATCGTG-3' and 3'-GA-ACAGCGGTGCAGGTAAGTG-5' and were designed to amplify a 381 bp sequence that spanned at least one intron, as determined by Southern hybridization and internal restriction enzyme analysis of mouse genomic DNA. Murine intron-spanning CD2 primers were 5'-CCTGGTCGCAGAGTTTAA-3' and 3'-TCTGTTCCTTGCAAGACC-5', and β-actin primers were 5'-GTGGGCCGCTCTAGGCACCA-3' and 3'-TGGCCTTAGGGTTCAGGGGG-5'.

11.1.6. Polymerase Chain Reaction

RNA was analyzed (FIG. 11) at 0 h and 24 h after LPS injection (2.25 mg/kg) by competitive PCR as described (Li et al., 1991, J. Exp. Med. 174:1259–1262), utilizing a 273 bp competitive MIF template. The competitive template was added in the range of 0.1 to 5 pg per reaction as shown in FIG. 11 and co-amplified with cDNA utilizing the MIF primers described in Section 9.1.5., supra. At 0 h, equivalent amounts of cDNA and competitor DNA amplification products appear in the lane showing 0.35 pg of MIF competitor template. At 24 h, equivalent amounts of cDNA and competitor DNA amplification products appear in the lane showing 1.0 pg of MIF competitor template.

11.1.7. Expression of MIF Protein IN VIVO

Pituitary MIF protein content was measured in BALB/c and C3H/HeJ mice challenged with LPS (FIG. 12). A similar LPS-dependent decrease in pituitary MIF protein content was observed in both C3H/HeN and BALB/$c^{nu/nu}$ mice as in BALB/c mice. Mice (N=2–5 per time point) were injected intraperitoneally with LPS at 2.25 mg/kg, pituitary lysates were prepared at intervals, and protein analyzed by Western blotting. Aliquots representing ¼ of a pituitary were electrophoresed, transferred to nitrocellulose membrane, and incubated with anti-rMIF serum (1:1000 dilution). Bound antibody was visualized by incubation with horseradish peroxidase-conjugated goat anti-rabbit antibody and substrate.

Nine-week-old mice were injected intraperitoneally with LPS at 2.25 mg/kg and serum samples (5 µl each) obtained at indicated time intervals were analyzed by Western blotting. Single bands corresponding to MIF were observed and quantified by laser densitometry (Shimadzu FDU-3, CS-9000 U). Recombinant MIF standards were electrophoresed and transferred in adjacent lanes. Scanning integrals are presented as relative MIF content normalized to the respective 0 h zone on each membrane. Each plotted point is the mean±SEM obtained for individual sera from multiple animals (N=2–5 per time point).

11.2. Results

The murine anterior pituitary cell line AtT-20 was cultured under low serum conditions in the presence of increasing amounts of bacterial endotoxin. At time intervals, the conditioned media was collected, concentrated, and analyzed for the presence of secreted proteins by SDS polyacrylamide gel electrophoresis. Endotoxin stimulation was observed to result in the specific time- and concentration-dependent secretion of a 12.5 kDa protein. The specificity of the secretory response was confirmed by the absence of LPS-induced cytopathicity, as determined by the lack of an LPS-related increase of supernatant lactate dehydrogenase activity. These measurements revealed no LPS-dependent increase in enzyme activity, despite prolonged (24 h) incubation under serum-free conditions (0 µg LPS: 112.8±17.9 IU/L, 50 µg LPS: 119.7±13.1 IU/L; P=NS). The 12.5 kDa protein was isolated, subjected to N-terminal microsequencing, and identified as the murine homolog of human MIF (96% identity over 27 amino acids).

Cellular activation by LPS is known to be potentiated by serum factors such as LPS-binding proteins that interact with specific cell surface receptors (Schuman et al., 1990, Science 349:1429–1431; Wright et al., 1990, Science 249:1431–1433). Supplementation of culture medium with 1% fetal bovine serum increased markedly the secretion of MIF from pituitary cells stimulated by LPS. As little as 100 pg/ml of LPS was found to induce pituitary cell secretion of MIF (FIG. 8). In contrast, MIF was not released by incubation with the inflammatory mediators tumor necrosis factor α, (1–100 ng/ml), interleukin-1β (1–100 ng/ml), interleukin-6 (1–100 ng/ml), or interferon-γ (1–100 ng/m.). Western blotting analysis of pituitary cell lysates also revealed that resting, non-stimulated cells contained significant amounts of pre-formed MIF. Immunocytochemistry studies confirmed these results and showed the disappearance of substantial amounts of immunoreactive, intracellular MIF within 16 hr of LPS stimulation (FIGS. 9A and 9B).

To investigate the pituitary expression of MIF in vivo, pituitary mRNA analysis was performed in mice injected with sublethal amounts of LPS (2.25 mg/kg). Pituitary RNA was isolated at increasing time intervals and subjected to reverse transcription-polymerase chain reaction (RT-PCR) analysis. Pituitary MIF mRNA levels increased with time and reached a plateau 16–24 h after LPS challenge in endotoxin-sensitive mice (FIG. 10). These findings were confirmed by competitive PCR analysis of representative cDNA preparations that showed a 3-fold increase in pituitary MIF mRNA after LPS stimulation (FIG. 11). Although infiltrating mononuclear cells were not evident in stained pituitary sections obtained after LPS treatment, in order to exclude a potential T cell contribution of pituitary MIF mRNA, pituitary cDNA was amplified with primers specific for the T cell-specific gene product, CD2. Despite intentional overcycling, RT-PCR analysis of CD2 was uniformly negative, ruling out infiltrating T cells as a possible source of pituitary MIF mRNA (FIG. 10). LPS did not induce pituitary MIF mRNA in the genetically endotoxin-resistant strain C3H/HeJ, while congenic endotoxin-sensitive C3H/HeN mice showed an increase of pituitary MIF mRNA between 0 hr and 24 hr similar to that observed with BALB/c mice.

The pituitary content of MIF protein in vivo was analyzed by Western blotting of pituitary lysates. Pituitaries obtained from normal, non-stimulated mice showed significant amounts of pre-formed MIF protein (FIG. 12). A significant decrease in pituitary MIF content was observed 8–20 h after LPS injection in endotoxin-sensitive mice, but not in endotoxin-resistant (C3H/HeJ) mice.

Previous studies over the years have identified MIF to be a product of lectin-stimulated T cells (Weiser et al., 1989, Proc. Natl. Acad. Sci. USA 86:7522–7526; Weiser et al., 1981, J. Immunol. 126:1958–1962). Since LPS does not directly activate T cells, MIF that appears in the circulation presumably results from direct stimulation of various cell types, including but not limited to pituitary cells and monocyte/macrophages by LPS or from indirect activation LPS-induced mediators of these and other cell types, including for instance T cells. In order to better establish the contribution of various cell types to circulating serum MIF in endotoxemic mice, control BALB/c, and T cell-deficient BALB/$c^{nu/nu}$ mice were injected intraperitoneally with LPS, serum samples were analyzed by gel electrophoresis and Western blotting, and serum MIF levels quantified by laser densitometry (FIG. 13). Serum MIF was detected at 2 h in wild-type mice (BALB/c) and increased over 20 h in a time-dependent fashion. In contrast, T cell-deficient (nude) mice showed a markedly delayed response in the appearance of serum MIF. MIF levels increased significantly only after 8 h of LPS challenge.

These findings indicate that pituitary MIF contributes directly to circulating serum MIF that is detectable in the post-acute phase (≧8 hours) of endotoxaemia. This time course is consistent with the disappearance of pituitary MIF protein and the induction of pituitary MIF mRNA levels that were observed in vivo (FIGS. 10 and 11). The results obtained in nude mice indicate that T cell MIF contributes primarily to the serum MIF that appears in the first 8 h. LPS treatment (2.25 mg/kg) of endotoxin-resistent C3H/HeJ mice produced no detectable serum MIF.

12. EXAMPLE

Production of Migration Inhibitory Factor by Macrophages

12.1. Materials and Methods 12.1.1. Reagents

E. coli O111:B4 LPS, polymyxin B, carbenicillin, PMSF and Tween-20 were obtained from Sigma (St. Louis, Mo.). LPS was resuspended in pyrogen-free water, vortexed, sonicated, aliquoted (5 mg/ml), and stored at −20° C. Serial dilutions of LPS were prepared in pyrogen-free water by sonication (Branson 3210, Danbury, Conn.). Gentamicin was from Gibco (Grand Island, N.Y.). Thioglycollate broth (Difco, Detroit, Mich.) was prepared according to the manufacturer's recommendation, autoclaved, and stored protected from light at room temperature. Horseradish peroxidase-conjugated goat anti-rabbit antibody was purchased from Pierce (Rockford, Ill.) and 4-chloro-1-naphthol and stabilized 3,3',5,5'-tetramethylbenzidene (TMB) substrate for horseradish peroxidase were from Promega (Madison, Wis.). Polyclonal anti-MIF serum was generated by immunizing New Zealand White rabbits (Hare Marland, Hewitt, N.J.) with purified recombinant murine MIF. On week 1 and 2, rabbits were inoculated intra-dermally with 100 $\mu$g of rMIF diluted in complete Freund's adjuvant, and with 50 $\mu$g of rMIF diluted in incomplete Freund's adjuvant on week 4. Immune serum was collected one week after the last inoculation.

12.1.2. Cytokines

Recombinant murine MIF (rMIF) was expressed in *E. coli* BL21/DE3 (Novagen, Madison, Wis.) and purified to homogeneity by anion exchange (Mono Q; Pharmacia, Piscataway, N.J.) and reverse phase chromatography (C8-SepPak, Millipore, Milford, Mass.), lyophilized and reconstituted in sodium phosphate buffer (20 mM, pH 7.2) following procedures in Example 6, supra. MIF bioactivity was established by measuring dose-dependent MIF-induced augmentation of *Leishmania major* killing by macrophages and by neutralization of this activity with anti-MIF antibody. rMIF contained 9 pg of endotoxin per $\mu$g protein as determined by the chromogenic Limulus amoebocyte assay (Bio-Whittaker Inc., Walkersville, Md.). Recombinant murine IL-1$\beta$ and IL-6 (5 $\mu$g/ml after reconstitution) were obtained from R&D (Minneapolis, Minn.) and recombinant murine IFN$\gamma$ ($10^5$ IU/ml) was from Boehringer-Mannheim (Indianapolis, Ind.). Cytokines were reconstituted in pyrogen-free water containing 0.1% of very low endotoxin BSA (Miles Inc., Kankakee, Ill.) and stored at –80° C. The endotoxin content of the reconstituted cytokines was 0.5 ng/$\mu$g of TNF$\alpha$, 2 ng/$\mu$g of IL-1$\beta$, 1.1 ng/$\mu$g of IL-6 and 0.06 pg/unit of IFN$\gamma$ as determined by the chromogenic Limulus amoebocyte assay.

12.1.3. Animals and Experimental Design

Eight to 10-week-old (19–21 g) female BALB/c (control), T cell-deficient BALB/c$^{nu/nu}$ (nude), and hypophysectomized BALB/c mice were purchased from Charles River (Kingston, N.Y.). Animals were housed in groups of 5 or 10 mice per cage with free access to food and water (supplemented with 5% glucose for hypophysectomized mice) and were acclimatized for 5 days prior to experimentation. Mice were injected i.p. with nonlethal doses of LPS (2.25 mg/kg for BALB/c and T cell-deficient mice, and 50 $\mu$g/kg for hypophysectomized mice), and sacrificed 2, 8 and 20 h after LPS challenge to collect serum. The LPS dose was adjusted to provide a comparable degree of lethality in the control BALB/c group as among the hypophysectomized mice, which are hypersensitive to endotoxin. Five $\mu$l of serum was analyzed by Western blotting and visualized with anti-MIF antibody.

12.1.4. Cells

RAW 264.7 murine macrophages, THP-1 human monocytes, ASL-1 murine and Jurkat human T lymphocyte cell lines were obtained from the American Type Culture Collection (Rockville, Md.). Cells were grown in RPMI 1640 medium (Gibco, Grand Island, N.Y.) containing 2 mM glutamine, 10% heat-inactivated fetal bovine serum (FBS) (HyClone, Logan, Utah), 50 $\mu$g/ml of carbenicillin and gentamicin. Medium for ASL-1 cells additionally was supplemented with 1 mM sodium pyruvate. Thioglycollate-elicited peritoneal macrophages were obtained from BALB/c mice that were injected i.p. 3–4 days previously with 2 ml of sterile thioglycollate broth. Cells were harvested under strict aseptic conditions by lavage of the peritoneal cavity with 5 ml of an ice-chilled 11.6% sucrose solution. After centrifugation (10 min at 800 g), cells were resuspended in RPMI/10% FBS, enumerated, and plated at a density of $2\times10^6$ or $4\times10^6$ cells/well. Human polymorphonuclear leukocytes were isolated from peripheral blood by density gradient centrifugation (Vadas et al. 1979, J. Immunol. 122: 1228; Sherry et al., 1981, In: Methods for Studying Mononuclear Phagocytes, Academic Press, N.Y., p. 187).

12.1.5. MIF Content of Macrophage and T Lymphocyte Lysates

Aliquots of $1\times10^6$ cells of each type were lysed with Tris-buffered saline (50 mM Tris-Base, 150 mM NaCl, pH 7.5) containing 1% NP-40, 0.5% deoxycholic acid, 0.1% SDS and 2 mM EDTA. Cellular debris was pelleted and the supernatants were diluted with an equal volume of reducing SDS-PAGE sample buffer. Ten microliter of lysate (equivalent to $5\times10^3$ cells) were electrophoresed through 18% polyacrylamide gels, and transferred to nitrocellulose membranes for Western blot analysis using polyclonal rabbit anti-MIF serum.

12.1.6. Stimulation of Macrophages by LPS and Cytokines

RAW 264.7 macrophages were washed with fresh medium, harvested by gentle scraping, resuspended in RPMI/10% FBS, and incubated at $2\times10^6$ or $4\times10^6$ cells/well in 3.5-cm tissue culture plates (Linbro®, Flow, McLean, Va.). After 3 h of incubation at 37° C. in a humidified atmosphere with 5% $CO_2$, nonadherent cells were removed and wells were washed twice with RPMI/1% FBS. Cells then were incubated for 12 h with LPS (at concentrations ranging from 1 pg/ml to 1 $\mu$g/ml) or with cytokines (1 or 10 ng/ml for TNF$\alpha$, IL-1$\beta$, and IL-6, and 10, 100 or 1000 IU/ml for IFN$\gamma$) diluted in RPMI/1% FBS. For time-course experiments, conditioned media of parallel cultures were removed at 3, 6, 9, 12 and 15 h intervals after LPS stimulation. Thioglycollate-elicited peritoneal macrophages ($10^7$ cells/well) were harvested as described and conditioned similarly to RAW 264.7 cells. Cells were incubated for 12 h either with LPS or with IFN$\gamma$ plus LPS. When co-stimulated with IFN$\gamma$ and LPS, cells were first incubated for an hour with IFN$\gamma$ (100 IU/ml) before addition of LPS at the indicated concentrations. At the end of each experiment, cell-culture media were collected, centrifuged (10 min at 800 g), and supplemented with PMSF (1 mM). Supernatants then were concentrated 10-fold by membrane filtration (10 kD cut-off) (Centricon-10, Amicon, Beverly, N.Y.). Cellular RNA was extracted from adherent cells.

12.1.7. Reverse Transcription and Polymerase Chain Reaction (RT-PCR)

Total cellular RNA was extracted from macrophages with RNAzol-B (Tel-Test Inc., Friendswood, Tex.) following the manufacturer's protocol. One $\mu$g of RNA was reversed transcribed using oligo (dT)$_{12-18}$ and M-MLV reverse transcriptase (Gibco, Grand Island, N.Y.) in a 50 $\mu$l reaction. Five $\mu$l of cDNA was amplified by PCR in a Perkin-Elmer/Cetus 9600 thermal cycler (denaturation 1 min at 94° C., annealing 1 min at 55° C., elongation 1 min at 72° C.) using murine MIF primers (32 cycles), TNF$\alpha$ primers (22 cycles), or $\beta$-actin primers (25 cycles). Intron-spanning TNF$\alpha$ primers were 5'-GCGGAGTCCGGGCAGGTCTA-3' and 3'-GGGGGGCTGGCTCTGTGAGG-5'. DNA amplification products were analyzed on 2% agarose gels and gel loading was normalized to β-actin PCR products. Quantification of MIF mRNA from LPS-stimulated RAW 264.7 macrophages was done by competitive PCR (Gilliland et al., 1990, Proc. Natl. Acad. Sci. USA 87: 2275). The 273 bp competitive cDNA template was added at the indicated concentrations and co-amplified with MIF cDNA using MIF primers.

12.1.8. Western Blots

For Western blotting, samples were resolved on 18% SDS polyacrylamide gels under reducing conditions and transferred onto nitrocellulose membrane (Schleicher and Schuell, Keene, N.H.) at 50 V and 150 mA for 16 h. Membranes were blocked with 500 mM NaCl, 50 mM Tris-Base, pH 7.5 buffer containing 5% nonfat dry milk and 0.05% Tween-20 and incubated first with polyclonal rabbit anti-rMIF serum and then with horseradish peroxidase-conjugated goat anti-rabbit IgG antibody (each diluted 1:1000 in 500 mM NaCl, 50 mM Tris-Base, pH 7.5 buffer with 1% BSA and 0.05% Tween-20). Polyclonal rabbit anti-murine MIF serum was demonstrated to react with both natural and recombinant murine and human MIF. Incubations were for 1 h each. MIF was visualized by development with chloronaphthol/$H_2O_2$ or with TMB substrate. Serum MIF bands were quantified by laser densitometry (Shimadzu FDU-3, CS-9000U, Braintree, Mass.). Faint densitometric signals in the MIF region were detected in most sera prior to LPS administration (0 h). Hence, scanning integrals are presented as relative serum MIF content (i.e. fold-increase) normalized to the respective 0 h zone (i.e. background or baseline staining) on each membrane. Each plotted point is the mean±SEM of individual sera from 2 to 5 animals.

12.1.9. MIF-induced Secretion of TNFα by Macrophages

Cells ($4 \times 10^6$/well) were processed as described above and stimulated for 12 h with rMIF at specified concentrations ranging from 100 pg/ml to 1 μg/ml. At 1 μg/ml of rMIF, LPS contamination was 9 pg/ml as assessed by Limulus assay. To neutralize this minute amount of LPS, rMIF was preincubated for 1 h at 37° C. with polymyxin B (1 μg/ml). MIF-induced TNFα activity in cell-culture supernatant was quantitated by L929 cell cytotoxicity (Wolpe et al., 1988, J. Exp. Med. 167: 570). MIF-induced TNFα activity was blocked completely by anti-TNFα antibodies. rMIF did not contribute to TNFα activity, as recombinant murine TNFα (dose range: 5 pg/ml to 1 μg/ml) cytotoxicity remained unchanged when rMIF (10 pg/ml to 10 μg/ml) or anti-MIF polyclonal serum were added to L929 cells together with rTNFα.

12.2. Results 12.2.1. Serum MIF Levels in LPS-injected Mice

Pituitary MIF contributes significantly to the MIF that appears in serum during endotoxemia. Serum MIF reached peak levels in normal mice at 20 h but was undetectable in hypophysectomized mice at this time, demonstrating that the pituitary is a major source of the MIF that appears in serum after LPS injection.

The central role played by MIF in endotoxic shock, together with the known hypersensitivity of hypophysectomized mice to LPS, led to experiments to examine more closely the kinetics of MIF appearance in the circulation during the early, acute phase (i.e. 2–8 h) of endotoxemic shock. For comparison purposes, serum MIF kinetics were also examined in nude mice, which lack a T cell source of MIF. Control, hypophysectomized, and nude mice were injected with LPS and serum prepared at intervals and quantified for MIF content by Western blotting and laser scanning densitometry (FIG. 14). Whereas serum MIF concentrations increased gradually over 20 h in control mice, hypophysectomized mice exhibited a rapid rise and then prompt fall in MIF that peaked 2 h after LPS injection. In nude mice, the rise in serum MIF was delayed by 8 to 12 h, but increased in a manner that was similar to that of the control mice. Given the lack of a pituitary source of MIF in the hypophysectomized mice, the MIF present in the circulation at 2 h reflected the release of MIF by an additional LPS-sensitive cell population. Such serum MIF kinetics were reminiscent of a macrophage TNFα response (Beutler et al., 1985, J. Exp. Med. 161: 984; Beutler et al., 1985, J. Immunol. 135: 3972; Michie et al., 1988, N. Eng. J. Med. 318: 1481) and thus the possibility that MIF was produced by cells of the monocyte/macrophage lineage was examined.

12.2.2. Expression of MIF in Resting Macrophages

Since both a pituitary cell-line (AtT-20) and the whole pituitary in vivo contain substantial amounts of pre-formed MIF, the intracellular MIF content of various inflammatory cells and cell lines was analyzed. Significant amounts of pre-formed MIF protein were found to be present in cell lysates obtained from resting, non-stimulated murine RAW 264.7 cells, murine peritoneal macrophages, and human THP-1 monocytes (FIG. 15). It was estimated that on average there was 0.1–1 pg of immunoreactive, pre-formed MIF protein per macrophage. The MIF content of murine or human monocytes/macrophages was similar to that of two T cell lines, the human Jurkat and the murine ASL-1. In contrast, cell lysates obtained from purified polymorphonuclear leukocytes (PMNs) exhibited no detectable MIF protein (FIG. 15).

12.2.3. MIF Secretion by LPS-stimulated Macrophages

MIF was observed to be secreted by macrophages into culture medium after LPS stimulation. In RAW 264.7 macrophages, MIF secretion was induced by as little as 10 pg/ml of LPS, peaked at 1 ng/ml, and was not detectable at LPS concentrations>1 μg/ml (FIG. 16A). In elicited peritoneal macrophages, 1 ng/ml of LPS was required to induce MIF secretion, and a maximal response was observed with 10–100 ng/ml of LPS (FIG. 16B). Of significance, co-stimulation of cells with IFNγ (100 IU/ml, given 1 h prior to LPS) plus LPS resulted in a >1000-fold increase in LPS responsiveness (FIG. 16C).

We next examined the time-course of MIF secretion in parallel cultures of RAW 264.7 macrophages maximally stimulated with 1 ng/ml of LPS. As assessed by Western blotting, MIF was first detected 6 to 9 h after LPS stimulation. Maximum amounts of MIF appeared in medium between 9 and 12 h post-LPS stimulation. MIF levels then decreased, indicating that by 12 h, MIF is removed or degraded at a rate that exceeds that of synthesis and release by macrophages.

12.2.4. Expression of MIF mRNA by LPS-stimulated Macrophages

The expression of MIF mRNA by LPS-stimulated RAW 264.7 macrophages was investigated by reverse transcription and polymerase chain reaction (RT-PCR). Parallel cultures were incubated for 12 h with medium or increasing amounts of LPS and analyzed for the expression of MIF, TNFα, and β-actin. MIF mRNA was expressed constitutively in non-stimulated murine RAW 264.7 cells (FIG. 17) and in elicited peritoneal macrophages. As expected, the expression of TNFα mRNA increased over the range of LPS concentrations (1 pg/ml to 1 μg/ml). In contrast, MIF mRNA levels correlated inversely with LPS concentration over this dose range. MIF mRNA level was highest in cells induced with 1 pg/ml of LPS and lowest in those induced by 1 μg/ml of LPS.

To assess more quantitatively the induction of MIF mRNA, cDNA was prepared from control and LPS-stimulated cultures of RAW 264.7 macrophages and analyzed by competitive PCR. The amount of competitive template which was required to obtain equivalent levels of MIF and competitor DNA amplification products was 1.5 pg for non-stimulated (control) macrophages and 3 pg for LPS-induced (100 pg/ml) RAW 264.7 macrophages (FIG. 18). Therefore, macrophage MIF mRNA increased approximately 2-fold after LPS induction, an increase comparable to that observed in pituitary cells in vivo (3-fold after induction with 45 μg of LPS injected i.p.). The time-course of MIF mRNA induction was examined in RAW 264.7 macrophages incubated with 1 ng/ml of LPS, the LPS concentration which induced maximum MIF secretion in these cells. MIF mRNA levels increased 6 h after LPS induction and remained elevated for up to 12 h post-LPS.

12.2.5. Interaction Between MIF and Pro-inflammatory Cytokines

The detection of elevated levels of MIF in blood after LPS administration together with the finding of an important role for MIF in experimental endotoxemia led to the investigation of the interaction between MIF and other pro-inflammatory cytokines. MIF release by RAW 264.7 macrophages was studied after stimulation with recombinant murine TNFα, IL-1β, IL-6, or IFNγ. By Western blotting, TNFα and IFNγ were found to induce MIF secretion in a dose-dependent fashion (FIG. 19). The lowest concentration of cytokine which was effective under these experimental conditions was 1 ng/ml of TNFα and 10 IU/ml of IFNγ. The TNFα and IFNγ effects could not be accounted for by LPS contamination of recombinant cytokine preparations, which were found to be 0.5 pg/ng of TNFα and 60 fg/U of IFNγ. LPS and IFNγ had additive/synergistic effect on MIF secretion, whereas TNFα and IL-1β did not. Finally, MIF production was not induced by either IL-1β or IL-6 at 1 or 10 ng/ml.

The secretion of TNFα and IL-1β by RAW 264.7 macrophages was examined after stimulation with rMIF. MIF samples were pre-incubated for 1 h with polymyxin B at 1 μg/ml to neutralize small amounts of contaminating LPS (9 pg/μg of MIF by the chromogenic Limulus assay). rMIF at concentrations ≧100 ng/ml was found to induce the secretion of bioactive TNFα as determined by the L929 cytotoxicity assay (FIG. 20). The MIF-induced TNFα bioactivity was blocked completely by anti-TNFα antibodies and rMIF did not contribute to TNFα cytotoxicity, as recombinant murine TNFα cytotoxicity was unchanged when rMIF or anti-MIF polyclonal serum were added to L929 cells together with rTNFα. IL-1β secretion, in contrast, was not detectable by Western blotting over the concentration of rMIF tested.

13. EXAMPLE

Steroid Induces MIF Secretion by Macrophages 13.1. Materials and Methods
13.1.1. Cell Preparation and MIF Induction RAW 264.7 murine macrophages were obtained from the American Type Culture Collection (Rockville, Md.). Cells were grown in RPMI 1640 medium (Gibco, Grand Island, N.Y.), 10% heat-inactivated fetal bovine serum (FBS) (HyClone, Logan, Utah), 50 μg/ml of carbenicillin and gentamicin. RAW 264.7 macrophages were washed with fresh medium, harvested by gentle scraping, resuspended in RPMI/10%FBS, and incubated at 3×10$^6$ cells/well in 3.5-cm tissue culture plates (Linbro®, Flow, McLean, Va.). After 3 h of incubation at 37° C. in a humidified atmosphere with 5% $CO_2$, nonadherent cells were removed and wells were washed twice with RPMI/1%FBS. In some experiments designed to test for inhibition of MIF release, test compounds were then added to the culture media. For example, the cells were pre-treated with 20α-dihydrocorticol at a final concentration of 10$^{-6}$M. Cells then were incubated for 12–15 h with various steroids at concentrations ranging from 10$^{-6}$M to 10$^{-14}$M (e.g., dexamethasone), along with the desired test compound (e.g., 20α-dihydrocortisol) if any. At the end of experiment, cell culture media were collected and centrifuged (10 min at 800 g). Cell-conditioned media were concentrated 10-fold by membrane filtration (10 kDa cut-off) (Centricon-10, Amicon, Beverly, N.Y.).

Thioglycollate-elicited peritoneal macrophages were obtained from BALB/c mice that were injected i.p. 3–4 days previously with 2 ml of sterile thioglycollate broth. Cells were harvested under strict aseptic conditions by lavage of the peritoneal cavity with 5 ml of an ice-chilled 11.6% sucrose solution. After centrifugation (10 min at 800 g), cells were resuspended in RPMI/10% FBS, enumerated and plated at a density of 3–4×10$^6$ cells/well. Cells were incubated for 12 to 15 h with various steroids (at concentrations ranging from 10$^{-6}$M to 10$^{-14}$M).

Samples were resolved on 18% SDS polyacrylamide gels under reducing conditions and transferred onto nitrocellulose membrane (Schleicher and Schuell, Keene, N.H.) at 50 V and 150 mA for 16 h. Membranes were blocked with 500 mM NaCl, 50 mM Tris-Base, pH 7.5 buffer containing 5% nonfat dry milk and 0.05% Tween-20 and incubated first with polyclonal anti-rMIF serum and then with horseradish peroxidase-conjugated goat anti-rabbit IgG antibody (each diluted 1:1000 in 500 mM NaCl, 50 mM Tris-Base, pH 7.5 buffer with 1% BSA). Polyclonal rabbit anti-murine MIF was shown to react with both natural and recombinant murine and human MIF. Incubations were 1 h each. MIF was visualized by development with chloronaphtol/$H_2O_2$ or with TMB substrate.

13.1.2. Steroid Injection

Canulated Sprague-Dawley female rats were purchased from Zivic-Miller. Animals were housed with free access to food and water and were acclimatized for at least 2 days prior to experimentation. Rats were injected i.v. through the jugular vein with either dexamethasone (1, 10 or 20 mg/kg), or with RU38486 (mifepristone) (1 or 10 mg/kg), or with the two drugs together (both at 10 mg/kg, RU38486 was injected 15 min. before dexamethasone). Serum was collected 3, 6, and 9 hours post-steroids injection and analyzed by Western blotting with anti-MIF antibody.

13.2. Results

MIF was observed to be secreted by murine macrophages (RAW 264.7 macrophages and/or elicited peritoneal macrophages) after stimulation with dexamethasone, hydrocortisol, 5β-Pregnane-3α,11β,17α,21-tetrol-20-one (tetrahydrocortisol), 4-pregnene-11β,17α,20α,21-tetrol-3-one (20α-dihydrocortisol), RU38486 (mifepristone), aldosterone, testosterone, and progesterone (Table V). In addition, dexamethasone at 10 mg/kg, RU 38486 at 10 mg/kg or a combination of both drugs induced MIF secretion in vivo. Serum MIF was detected 3 to 6 hours after steroid injection.

As shown in FIG. 21, pretreatment and co-administration of 20α-dihydrocortisol attenuates or abolishes the MIF response to dexamethasone.

TABLE V

STEROIDS INDUCE MIF SECRETION BY MURINE MACROPHAGES

| Steroids | Range of Steroid Concentrations (M) Inducing MIF in: | |
|---|---|---|
| | RAW 264.7 Macrophages | Peritoneal Macrophages |
| Dexamethasone | $10^{-8}$ to $10^{-14}$ | $10^{-8}$ to $10^{-12}$ |
| Hydrocortisone | $10^{-8}$ to $10^{-12}$ | $10^{-8}$ to $10^{-16}$ |
| 5β-Pregnane-3α,11β,17α,21-Tetrol-20-one (Tetrahydrocortisol) | $10^{-8}$ to $10^{-14}$ | Not tested |
| 4-pregnene-11β,17α,20α,21-tetrol-3-one (20α dihydrocortisol)* | $10^{-10}$ to $10^{-14}$ | $10^{-10}$ to $10^{-14}$ |
| Aldosterone | $10^{-10}$ to $10^{-14}$ | $10^{-8}$ to $10^{-14}$ |
| Testosterone | $10^{-6}$ to $10^{-14}$ | $10^{-8}$ to $10^{-14}$ |
| RU-38486 (mifepristone)* | $10^{-8}$ to $10^{-14}$ | Not tested |
| Progesterone | $10^{-4}$ to $10^{-12}$ | Not tested |

*At higher concentrations, these steroids inhibit the macrophage release of MIF in response to a challenge dose of dexamethasone, i.e., a dose that normally would induce MIF release.

14. EXAMPLE

Organ Distribution of MIF and MIF Receptor

The following example describes the organ distribution of MIF and MIF receptor in mice.

14.1. Materials and Methods
14.1.1. Labeling of Exogenous MIF

Five μl $^{125}$I-MIF (specific activity, $2\times10^4$ cpm/ng) together with 5 μl $^{51}$Cr-labeled red blood cells (RBCs), were injected intravenously in a total of 300 μl saline. One preparation additionally contained 40 μg unlabeled MIF as a competitor. Ten minutes prior to injection, each mouse was given 10 mg Na-iodide i.p. Mice were sacrificed 10 minutes after injection.

14.1.2. Tissue Preparation

Four hundred μl blood was collected from each mouse immediately after sacrificing. Additionally, various organs were removed, rinsed in PBS, and blotted dry on filter paper. Organs were weighed and radioactivity was counted on two separate windows (one for $^{125}$I, one for $^{51}$Cr) on a gamma counter. The remainder of the carcass was also weighed and counted.

14.1.3. Organ Distribution of Endogenous MIF

The organ distribution of MIF protein was examined in a 8 to 10-week old female BALB/c mouse sacrificed by $CO_2$ asphyxiation and necropsied under aseptic conditions. Organs (brain, liver, spleen, kidneys, adrenals and lungs) were excised, sectioned and homogenized at 4° C. with Tris-buffered saline (50 mM Tris-Base, 150 mM NaCl, pH 7.5) containing 1% NP-40, 0.5% deoxycholic acid, 0.1% SDS, 2 mM EDTA and 1 mM PMSF. Cellular debris was pelleted and aliquots of organ lysate supernatants, adjusted for protein concentration, were diluted with an equal volume of reducing SDS-PAGE sample buffer. Samples (equivalent to 60 μg of protein) were electrophoresed through 18% polyacrylamide gels and transferred to nitrocellulose membranes for Western blot analysis using polyclonal anti-MIF serum.

14.2. Results

The organ distribution of endogenous MIF protein was examined in normal mice. Mouse tissues were homogenized and aliquots of total protein electrophoresed and analyzed by Western blotting. As shown in FIG. 22, pre-formed MIF was detectable in mouse liver, spleen, kidney and brain. Much lower amounts were also found in the adrenals and lungs. These organs contain significant amounts of macrophages, suggesting that the MIF protein present in these tissues is at least partly macrophage-associated.

$^{125}$I-MIF was also injected into mice in order to determine the tissue distribution of MIF receptors. The index of the tissue specific localization of radiolabelled MIF was determined, as described in Beutler et al., 1985, J. Immunol. 135:3972. As shown in Table VI, a particularly high level of MIF-binding was observed in the kidneys and liver among the organs examined.

TABLE VI

| Organs | Index of Tissue Specific Localization of Radiolabelled MIF |
|---|---|
| Liver | 256 |
| Kidney | 2334 |
| Lung | 52 |
| Adrenal | 47 |
| Spleen | 78 |
| Small Intestine | 247 |
| Large Intestine | 122 |
| Brain | 17 |
| Skin | 103 |

15. EXAMPLE

MIF Receptor Identification

In this example, receptor proteins that bind to MIF are identified, and the partial amino acid sequences of each of these MIF receptors are presented.

15.1. Materials and Methods
15.1.1. Cell Lysate Preparation

Two large tissue culture plates ($5\times10^7$ cells) of murine RAW 264.7 cells (a monocyte-like line) were solubilized by the addition of 2.5 ml of lysis buffer (50 MM Tris pH 7.5, 150 mM NaCl, 1% Triton X-100, with protease inhibitors). Plates were incubated on ice with gentle rotation. Plates were then scraped, the contents collected, and centrifuged in 4 microfuge (1.5 ml) tubes at 10,000×g for 10 min at 4° C. Supernatants were collected and stored on ice.

15.1.2. Affinity Chromatography

For preparation of an MIF-conjugated affinity column, 1 gm of CNBr-Sepharose was first washed with 1 mM HCl. Bacterial recombinant murine MIF (3 mg) was dissolved in 40% acetonitrile/$H_2O$. MIF solution then was mixed with activated CNBr-Sepharose and incubated for 3 hr at room temperature. Unreacted CNBr-Sepharose then was quenched by incubation with 0.2 M glycine pH 8.0 overnight. Coupling efficiency was determined by comparison of optical absorbance of MIF solution before and after coupling, and determined to be 85%. Resin then was washed, poured into a column and equilibrated with lysis buffer.

Supernatants of lysed RAW cell preparation were loaded onto MIF-Sepharose at a flow rate of 2 ml/hr, and washed sequentially with 3 column volumes of lysis buffer. Remaining bound protein was eluted with 5 volumes of 0.05% Triton X-100 in 0.1 M glycine, pH 2.5. Fractions were collected and buffered with 90 μl of 1 M Tris base.

15.1.3. Gel Electrophoresis

Fractions containing protein species of interest were concentrated over Centricon-10 membranes, resuspended in equal volumes of 2×Laemmli sample buffer, and electrophoresed on 7.5% SDS-PAGE gels. Proteins were transferred onto PVDF filters utilizing 10 mM CAPS pH 11/20% methanol transfer buffer. Filters were stained with Ponceau-S and protein bands corresponding to molecular weights 52 kD and 72 kD were identified and excised.

15.1.4. Microsequencing Analysis

The excised protein bands were subjected to microsequencing analysis using automated gas-phase sequencing methods (Applied Biosystems).

15.2. Results

Putative MIF receptor protein was isolated by MIF affinity chromatography of RAW cell lysates on an MIF affinity column, as described above in Section 13.1.2.

Three fractions (6, 7, 8) were found to contain two protein species, 52 kD and 72 kD, when analyzed by SDS-PAGE. When parallel transfers were performed onto membranes which were then incubated with $^{125}$I-labelled MIF, it was demonstrated that both the 52 kD and the 72 kD bands bound radiolabelled MIF. Ligand binding was inhibited by simultaneous incubation of membranes with excess unlabelled MIF, thereby showing that binding was MIF specific.

Protein from the 52 kD species was isolated and subjected to amino acid microsequencing. A partial amino acid sequence was obtained from this 52 kD putative MIF receptor, as shown here:

Ile-X-His-Asn-Thr-Val-Ala-Thr-Glu-Ile-(Ser)-(Gly)-Tyr-Asn-(Asn/Gly)-(Ala)-(Met)

The residues in parenthesis are tentative designation.

Similarly, protein from the 72 kD species was isolated and sequenced. A partial amino acid sequence was determined and shown here:

Ala-Lys-Lys-Gly-Ala-Val-Gly-Gly-Ile

16. EXAMPLE

Inhibition of Humoral Immunity With Anti-MIF Antibody

Treatment of naive animals with purified neutralizing anti-MIF antibody was shown to inhibit the development of a primary immune response to a soluble test antigen, e.g. ribonuclease (RNase). Five BALB/c mice were immunized by intraperitoneal injection with 0.1 mg of bovine RNase A (dissolved in 0.1 ml sterile PBS) emulsified with complete Freund's adjuvant (1:1). This was followed by the intra-abdominal injection of 0.4 mg polyclonal anti-MIF IgG (in 0.1 ml PBS) or, in control mice, 0.4 mg of purified pre-immune IgG. The antibodies were administered again at 3, 5 and 7 days after the primary immunization. After 12 days, the animals were sacrificed and blood samples were collected for serum assays for anti-RNase immunoglobulin by ELISA with RNase-coated plates. When compared to RNase-immunized controls, anti-MIF treated RNase-immunized mice showed a 70% reduction in circulating anti-RNase immunoglobulin levels (n=5 mice per group).

17. EXAMPLE

Production of Monoclonal Antibodies Directed Against Human and Murine MIF

Hybridomas secreting monoclonal antibodies (MAbs) directed against human and murine forms of MIF were made and isolated according to methods well known in the art. In brief summary, female BALB/c mice were immunized intraperitoneally (i.p.) with recombinant murine or human MIF (10 µg/mouse) in Ribi Adjuvant (Ribi Immunochem.). During the immunization and boost period, mice were tail-bled and serum anti-MIF antibody titers, as well as isotype distribution (IgM vs IgG), were assayed by microtiter plate-based direct enzyme-linked immunosorbent assay (ELISA) methods on wells with immobilized recombinant MIF (250 ng/ml; 55 µl/well) as antigen. Immunized mice were given booster injections of recombinant MIF (10 µg/mouse) in Ribi Adjuvant at least four times before spleens were removed for fusion. Three days before spleen cell fusion with mouse myeloma cells (P3X63Ag8.653; American Type Culture Collection) using polyethylene glycol (Boerhinger Mannheim), mice were boosted i.p. with both murine and human MIF (10 µg in PBS). Hybridomas were expanded under HAT (hypoxanthine, aminopterin, and thymidine; GIBCO) selection medium (DMEM containing HAT, 10% Condimed (Boerhinger Mannheim), 20% FBS (Hyclone), and antibiotics (penicillin, streptomycin; GIBCO) for two to three weeks. Culture supernatants from growing hybridomas were screened for anti-MIF antibodies by direct ELISA methods with immobilized recombinant MIF.

Immunoreactivity of antibodies from anti-MIF positive clones was further analyzed by Western immunoblotting techniques, and high-titer producing hybridomas were chosen for re-cloning by limiting dilution. Anti-MIF monoclonals were isotyped using Screentype ELISA (Boehringer Mannheim). Hybridomas secreting desired monoclonal antibodies (IgG-type) were grown as ascites in BALB/c mice, and MAb's were purified using T-gel chromatography (Pierce). Several IgM-type anti-MIF monoclonal antibodies were identified but not further characterized. Several IgG-secreting hybridomas were isolated and characterized (Table VII).

TABLE VII

| | Reactivity with | | |
|---|---|---|---|
| | Human MIF | Murine MIF | IgG Subtype |
| VIIG3 | − | + | IgG2b |
| IXD11 | − | + | IgG2a |
| XB2 | − | + | IgG3 |
| XID5 | − | + | IgG2b |
| XIG2 | − | + | IgG3 |
| VD8 | − | + | IgG2b |
| IID9 | + | + | IgG1 |
| IIID9 | + | + | IgG1 |
| XIF7 | + | + | IgG2b |
| I31 | + | + | IgG1 |
| IV2.2 | + | + | IgG1 |
| XI7 | + | + | n.d. |
| XII15.6 | + | + | IgG1 |
| XIV15.4 | + | + | IgG1 |

17.1 Test for Anti-MIF Neutralization Activity

Purified anti-MIF monoclonal antibodies were first tested for neutralization activity in a macrophage killing assay. Thioglycollate-elicited mouse peritoneal macrophages were obtained from BALB/c mice, allowed to adhere for 4 hours, and then infected with the intracellular parasite *Leishmania major* at a parasite:macrophage ratio of 8:1. After washing, infected macrophage cultures were treated with recombinant human MIF (which enhances macrophage-killing of intracellular parasites in a dose-dependent fashion when compared to culture medium controls) with or without added VIIG3 or XID5 monoclonal anti-MIF antibodies (25 µg/ml). Both antibodies were found to neutralize the MIF-enhanced killing of *L. major* by about 50%.

In separate experiments, purified monoclonal anti-MIF antibodies were tested for MIF neutralizing activity in a

[³H]-thymidine incorporation assay with primary murine T cells cultured on anti-CD3 IgG-coated (Pharmingen) tissue culture plates. Briefly described, this assay employed BALB/c spleen cells that were isolated using murine T cell enrichment columns (R&D) and grown on anti-CD3 IgG-coated 96 well micro-titer plates in RPMI containing 10% FBS, antibiotics (penicillin, streptomycin) and L-glutamine together with anti-MIF or control mouse monoclonals antibodies. After 48 hours, T cells were pulsed with [³H]-thymidine for 16 to 18 hours, harvested and counted by beta-scintillation counting methods. As a positive control, anti-IL-2 monoclonal antibodies (Genzyme) were added to inhibit proliferation and associated [³H]-thymidine incorporation. Both the VIIG3 and the XID5 antibodies decreased thymidine incorporation by about 20%; anti-IL-2 treatment reduced [³H]-thymidine incorporation by about 75%.

17.2. Development of Quantitative Sandwich Elisa for MIF

A MIF-specific "sandwich" ELISA technique was developed, based on the trapping of MIF by immobilized VIIG3 antibody followed by detection with a rabbit polyclonal anti-MIF antiserum. This assay was performed as follows:

Immulon II (Dynatech) ELISA plate wells were coated with 10–15 μg/ml MAb (VIIG3) in PBS (65 μl/well); the MAb had been purified from ascites using T-gel absorbant (Pierce). Plates were sealed and incubated overnight at room temperature. Wells were then blocked with Superblock (Pierce) containing 2% goat serum (140–150 μl/well) for 1–2 hours at room temperature. Plates were washed using an automated ELISA plate washer (twice with TBS 0.05% Tween20 using 200 μl/well). MIF samples and standards were prepared in 0.5 ml or 1.5 ml eppendorf tubes by adding Tween20 to culture supernatants to a final concentration of 0.2%. Cell lysates were likewise diluted in TBS buffer with Tween20 at a final concentration of 0.2%. Standards were prepared similarly by diluting purified recombinant murine or human MIF in DMEM/1% FBS/0.2% Tween20. Samples and standards were applied to the plate (60 μl/well) and the plate sealed and incubated overnight at 4° C. with gentle shaking. The plate was then washed five times with TBS/ 0.05% Tween20, and second antibody (e.g. Rabbit 102 anti-murMIF serum, 1:220 in TBS/0.2% Tween20/2% goat serum) added at 60 μl/well. The plate was sealed and incubated 2 hours at room temperature with gentle shaking. All wells were then washed five times with TBS/0.05% Tween20 and tertiary antibody-enzyme conjugate (commercially available goat anti-rabbit IgG-alkaline phosphatase, diluted 1:4000 in TBS/0.2% Tween20/2% goat serum as recommended by the manufacturer, Boehringer Mannheim) was added at 60 μl/well. The plate was covered, incubated for 35 minutes at room temperature, and then washed 5 times with TBS/0.05% Tween20. The assay was then developed with p-nitrophenyl phosphate (pNPP) solution as recommended by the manufacturer (5 mg Sigma 104 tablet in 5 ml AP buffer: 10 mM diethanolamine/0.5 mM $MgCl_2$, pH 9.5). Reaction product was allowed to develop in the dark at room temperature, and read at 405 nm within 15–30 minutes. This assay gives range of sensitivity of about 100 pg/ml-250 ng/ml. It should be noted that for the practice of this "sandwich" technique, various combinations of two or more MIF-specific antibodies may be used to capture and detect MIF in a sample. The immobilized antibody is not restricted to VIIG3 antibody, and the second antibody is not limited to a rabbit antiserum.

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A pharmaceutical composition comprising an anti-Migration Inhibitory Factor (MIF) antibody in a suitable pharmaceutical carrier, wherein the MIF has a molecular weight of approximately 12.5 kDa as determined by SDS PAGE, and wherein the anti-MIF antibody is a monoclonal antibody that binds to and neutralizes biological activity of the 12.5 kDa MIF and the anti-MIF antibody is present in an amount suitable for administration to a patient in a dosage range that is therapeutically effective for treating a condition or disease caused by cytokine-mediated toxicity.

2. The pharmaceutical composition of claim 1 wherein the anti-MIF antibody is a chimeric monoclonal antibody.

3. The pharmaceutical composition of claim 1 wherein the anti-MIF antibody is present in an amount suitable for administering the antibody in a dosage range from about 0.1 mg/kg body weight to about 20 mg/kg body weight.

4. The pharmaceutical composition of claim 1 wherein said condition or disease caused by cytokine-mediated toxicity is selected from the group consisting of endotoxin-induced septic shock, endotoxin-induced toxic shock, shock, inflammatory diseases, graft versus host disease, autoimmune diseases, acute respiratory distress syndrome, granulomatous diseases, chronic infections, transplant rejection, cachexia, asthma, viral infections, parasitic infections, malaria, and bacterial infections.

5. The pharmaceutical composition of claim 1 wherein said monoclonal antibody is a humanized monoclonal antibody.

6. An article of manufacture comprising packaging material and a pharmaceutical composition contained within the packaging material, said pharmaceutical composition comprising an anti-Migration Inhibitory Factor (MIF) antibody wherein:

the MIF has a molecular weight of approximately 12.5 kDa as determined by SDS PAGE and the anti-MIF antibody is a monoclonal antibody that binds to and neutralizes biological activity of the 12.5 kDa MIF;

the anti-MIF antibody is present in an amount that is therapeutically effective for treating a condition or disease caused by cytokine-mediated toxicity; and said packaging material includes a label that indicates that the anti-MIF antibody is therapeutically effective for treating a condition or disease caused by cytokine-mediated toxicity.

7. The article of manufacture of claim 6 wherein said condition or disease caused by cytokine-mediated toxicity is selected from the group consisting of endotoxin-induced septic shock, endotoxin-induced toxic shock, shock, inflammatory diseases, graft versus host disease, autoimmune diseases, acute respiratory distress syndrome, granulomatous diseases, chronic infections, transplant rejection, cachexia, asthma, viral infections, parasitic infections, malaria, and bacterial infections.

8. The article of manufacture of claim 6 wherein said monoclonal antibody is a humanized monoclonal antibody.

9. The article of manufacture of claim 6 wherein the anti-MIF antibody is a chimeric monoclonal antibody.

* * * * *